US012565532B2

(12) United States Patent
FitzGerald et al.

(10) Patent No.: US 12,565,532 B2
(45) Date of Patent: Mar. 3, 2026

(54) MONOCLONAL ANTIBODIES THAT BIND EGFRvIII AND THEIR USE

(71) Applicant: THE UNITED STATES OF AMERICA, as represented by the Secretary, Department of Health and Human Services, Bethesda, MD (US)

(72) Inventors: David Joseph FitzGerald, Rockville, MD (US); Eric Chun Hei Ho, Rockville, MD (US); Antonella Antignani, Potomac, MD (US); Robert Joseph Sarnovsky, Phoenix, MD (US)

(73) Assignee: The United States of America as represented by the Secretary, Department of Health and Human Services, Bethesda, MS (US)

( * ) Notice: Subject to any disclaimer, the term of this patent is extended or adjusted under 35 U.S.C. 154(b) by 1100 days.

(21) Appl. No.: 17/623,370

(22) PCT Filed: Jul. 1, 2020

(86) PCT No.: PCT/US2020/040544

§ 371 (c)(1),
(2) Date: Dec. 28, 2021

(87) PCT Pub. No.: WO2021/003297

PCT Pub. Date: Jan. 7, 2021

(65) Prior Publication Data

US 2022/0380474 A1 Dec. 1, 2022

Related U.S. Application Data

(60) Provisional application No. 62/869,956, filed on Jul. 2, 2019.

(51) Int. Cl.

| | |
|---|---|
| ***C07K 16/28*** | (2006.01) |
| ***A61K 47/68*** | (2017.01) |
| ***C07K 14/21*** | (2006.01) |

(52) U.S. Cl.

CPC ...... *C07K 16/2863* (2013.01); *A61K 47/6803* (2017.08); *A61K 47/68031* (2023.08); *A61K 47/68033* (2023.08); *C07K 14/21* (2013.01); *C07K 16/2809* (2013.01); *C07K 2317/24* (2013.01); *C07K 2317/51* (2013.01); *C07K 2317/515* (2013.01); *C07K 2317/55* (2013.01); *C07K 2317/565* (2013.01); *C07K 2317/94* (2013.01)

(58) Field of Classification Search

CPC .......................... C07K 16/2863; C07K 14/21; C07K 16/2809; C07K 2317/24; C07K 2317/51; C07K 2317/515; C07K 2317/55; C07K 2317/565; C07K 2317/94; A61K 47/6803; A61K 47/68031; A61K 47/68033; A61K 47/6849; A61K 2039/505; A61P 35/00

See application file for complete search history.

(56) References Cited

U.S. PATENT DOCUMENTS

| | | | | |
|---|---|---|---|---|
| 2010/0111979 | A1* | 5/2010 | Weber .................... | A61P 35/00 435/375 |
| 2015/0259423 | A1* | 9/2015 | Kirshner ................ | A61K 45/06 |
| 2018/0215811 | A1 | 8/2018 | Spellberg et al. | |

FOREIGN PATENT DOCUMENTS

| | | | |
|---|---|---|---|
| CN | 105873612 | A | 8/2016 |
| CN | 108699124 | A | 10/2018 |
| WO | WO-2015/031693 | A1 | 3/2015 |
| WO | WO 2017/125830 | A1 | 7/2017 |

OTHER PUBLICATIONS

Gan et al., Targeting of a Conformationally Exposed, Tumor-Specific Epitope of EGFR as a Strategy for Cancer Therapy, *Cancer Res.* 71(12): 2924-2930 (Jun. 15, 2012).

Chistiakov et al., "The EGFR variant III mutant as a target for immunotherapy of glioblastoma multiforme," *European Journal of Pharmacology* 810: 70-82 (Sep. 5, 2017).

GenBank Accession No. NC_000007, "*Homo sapiens* chromosome 7, GRCh38.p13 Primary Assembly," 49 pages (Jun. 14, 2019).

GenBank Accession No. NM_005228, "*Homo sapiens* epidermal growth factor receptor (EGFR), transcript variant 1, MRNA," 12 pages (Jun. 18, 2019).

GeneCards GCID No. GC07P055019, "Epidermal Growth Factor Receptor," 24 pages (Jul. 2020).

International Search Report and Written Opinion from parent PCT Application No. PCT/US2020/040544, 8 pages (mailed Sep. 21, 2020).

Padfield et al., "Current therapeutic advances targeting EGFR and EGFRvIII in glioblastoma," *Frontiers in Oncology* 5(1): 1-8 (Jan. 2015).

* cited by examiner

*Primary Examiner* — Nelson B Moseley, II

(74) *Attorney, Agent, or Firm* — Klarquist Sparkman, LLP

(57) ABSTRACT

Disclosed are monoclonal antibodies and antigen binding fragments that specifically bind epidermal growth factor receptor (EGFR) variant (v) III, conjugates thereof, and chimeric antigen receptors. Nucleic acid molecules encoding the heavy and light chain domains of the antibodies, and the chimeric antigen receptors (CARs), are also disclosed, as are host cells expressing the nucleic acid molecules. In addition, disclosed is the use of these monoclonal antibodies, antigen binding fragments, conjugates, and T cells expressing the CARs, such as for the treatment of a tumor expressing EGFRvIII. Also disclosed are methods for detecting a tumor that expresses EGFRvIII.

38 Claims, 32 Drawing Sheets

Specification includes a Sequence Listing.

FIG. 6A
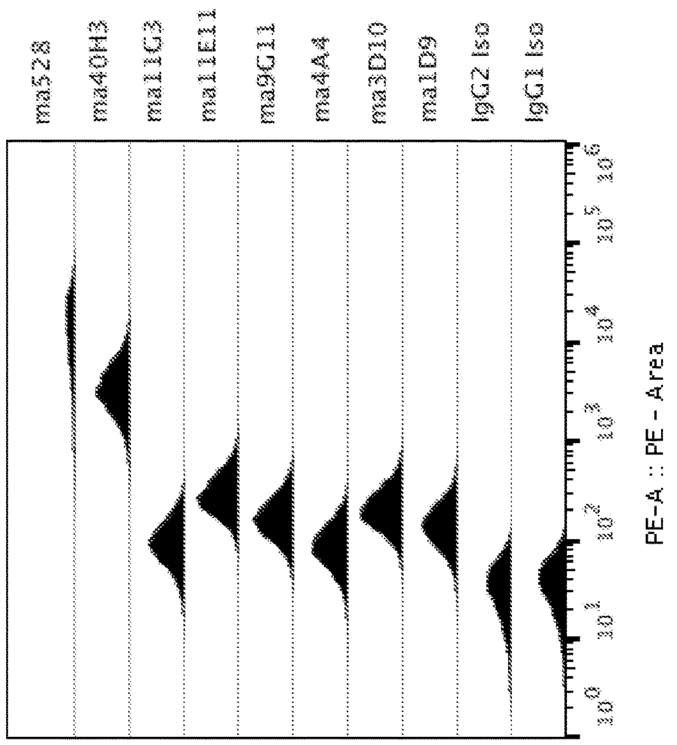
| | Sample Name | Median : PE-A | Count |
|---|---|---|---|
| ■ | ma528 | 10674 | 4763 |
| ■ | ma40H3 | 3159 | 9901 |
| ■ | ma11G3 | 90.3 | 9491 |
| ■ | ma11E11 | 274 | 9882 |
| ■ | ma9G11 | 160 | 9615 |
| ■ | ma4A4 | 83.3 | 9835 |
| ■ | ma3D10 | 196 | 10303 |
| ■ | ma1D9 | 136 | 9183 |
| ■ | IgG2 Iso Con | 31.2 | 8343 |
| ■ | IgG1 Iso Con | 34.3 | 9028 |
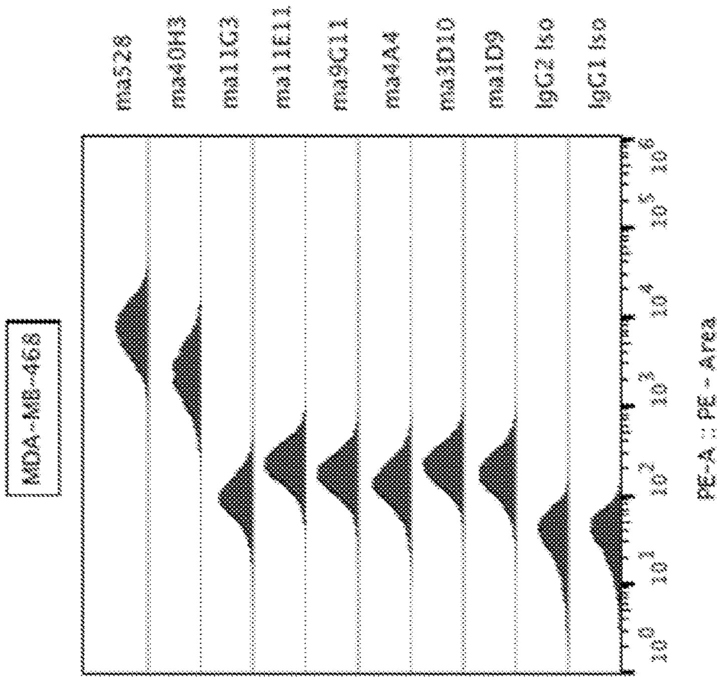
| | Sample Name | Median : PE-A | Count |
|---|---|---|---|
| ■ | ma528 | 6862 | 11216 |
| ■ | ma40H3 | 2143 | 11080 |
| ■ | ma11G3 | 90.3 | 9431 |
| ■ | ma11E11 | 216 | 11062 |
| ■ | ma9G11 | 166 | 11036 |
| ■ | ma4A4 | 130 | 11049 |
| ■ | ma3D10 | 205 | 11031 |
| ■ | ma1D9 | 166 | 11064 |
| ■ | IgG2 Iso Con | 34.1 | 9823 |
| ■ | IgG1 Iso Con | 34.9 | 9813 |

FIG. 6B
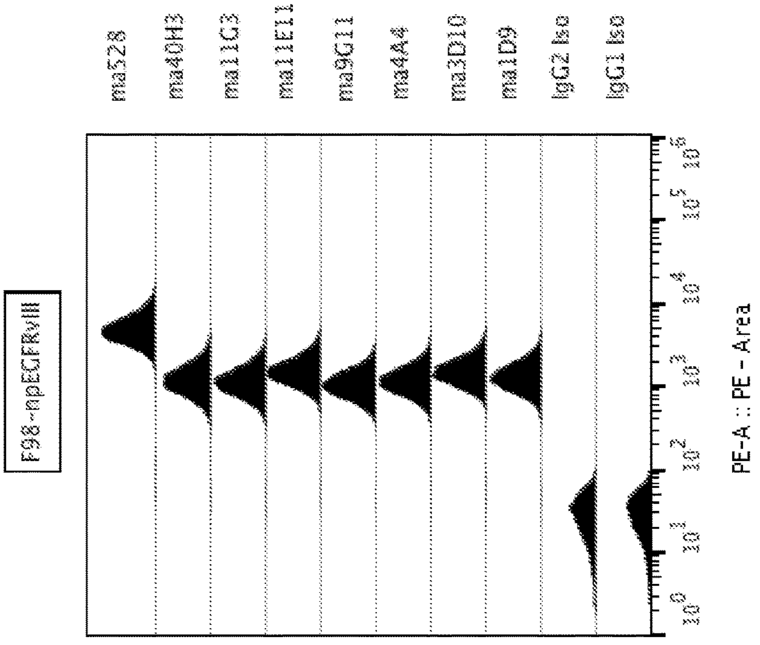
| Sample Name | Median : PE-A | Count |
|---|---|---|
| ma528 | 4471 | 10725 |
| ma40H3 | 1122 | 10506 |
| ma11G3 | 1084 | 10529 |
| ma11E11 | 1435 | 10478 |
| ma9G11 | 1010 | 10558 |
| ma4A4 | 1110 | 10554 |
| ma3D10 | 1425 | 10382 |
| ma1D9 | 1228 | 10423 |
| IgG1 Iso Con | 26.2 | 8304 |
| IgG2 Iso Con | 26.9 | 8249 |
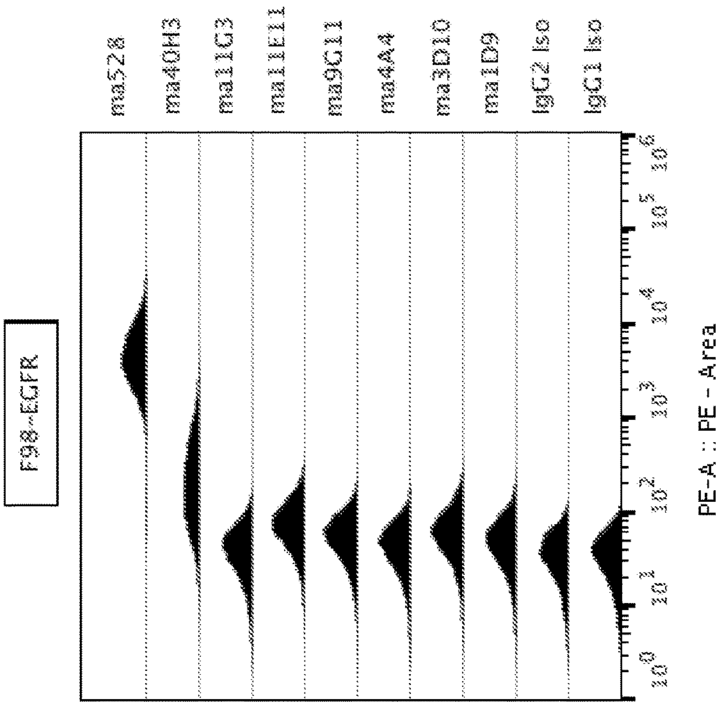
| Sample Name | Median : PE-A | Count |
|---|---|---|
| ma528 | 4041 | 10381 |
| ma40H3 | 187 | 10156 |
| ma11G3 | 37.9 | 9650 |
| ma11E11 | 69.4 | 10197 |
| ma9G11 | 51.7 | 9941 |
| ma4A4 | 41.7 | 9545 |
| ma3D10 | 56.9 | 10044 |
| ma1D9 | 45.5 | 9697 |
| IgG2 Iso Con | 33.5 | 9377 |
| IgG1 Iso Con | 32.6 | 9333 |

| | Sample Name | Median : PE-A | Count |
|---|---|---|---|
| ■ | ma528 | 2723 | 9166 |
| ■ | ma40H3 | 96.9 | 11193 |
| ■ | ma11G3 | 39.6 | 10181 |
| ■ | ma11E11 | 96.2 | 10564 |
| ■ | ma9G11 | 90.6 | 10511 |
| ■ | ma4A4 | 48.0 | 10041 |
| ■ | ma3D10 | 51.2 | 9944 |
| ■ | ma1D9 | 41.4 | 9309 |
| ■ | IgG2 Iso Con | 47.6 | 9983 |
| ■ | IgG1 Iso Con | 48.0 | 9883 |

FIG. 8A

```
                            FR1                CDR1           FR2       CDR2      FR3
                 <------------------------><----------><---------------><-><-----------
                          10        20        30        40        50        60
40H3-1-Light     DIQMTQSPASQSASLGESVTITCLASQT------IGTWVAWYQQKPGRSPQLLIYGATNLADGVPSRFSG 70
3D10-1-Light     DIVMSQSPSSLGVSVGEKVTMSCKSSQSLLDSRNQKNYLAWYQQKPGQSPKLLIYWASTRESGVPDRFTG 70
9G11-1-Light     DIVMSQSPSSLGVSVGEKVTMSCKSSQSLLDSRNQKNYLAWYQQKPGQSPKLLIYWASTRESGVPDRFTG 70
1D9-1-Light      DIVMSQSPSSLAVSVGEKVTMRCRSSQSLLDSYHQKNYLAWYLQKPGQSPKLLIYWASTRESGVPDRFTG 70
4A4-1-Light      DIVMSQSPSSLAVSVGEKVTMRCRSSQSLLDSYHQKNYLAWYLQKPGQSPKLLIYWASTRESGVPDRFTG 70
11E11-1-Light    DIVMSQSPSSLAVSVGEKVSLTCKSSQSLLDN--QKHYLAWYQQKPGQSPKLLIYWASTRESGVPDRFTG 70
11G3-1-Light     DIVMSQSPSSLPVSVGEKVSLTCKSSRSLLDN--QKHYLAWYQQKPGQSPKLLIYWASTRESGVPDRFTG 70
                 ** * *** *   * ** *   *   *            *** **** ** **** *     *** ** *

                                          CDR3       FR4
                 ----------------------->.<-------><-------->
                          80        90       100       110
40H3-1-Light     SGSGTKFSFKISSLQAEDFVSYYCQQLYSNPYTFGGGTKLEIK 113
3D10-1-Light     SGSGTEFTLTISSVKAEDLAIYYCQQYYNYPYTFGGGTKLEIT 113
9G11-1-Light     SGSGTEFTLTISSVKAEDLAIYYCQQYYNYPYTFGGGTKLEIT 113
1D9-1-Light      SGSGTDFTLTISSVKAEDLAVYYCQEYYRYPYTFGGGTKLEIK 113
4A4-1-Light      SGSGTDFTLTISSVKAEDLAAYYCQEYYRYPYTFGGGTKLEIK 113
11E11-1-Light    SGSGTEFTLTISSVKAEDLAVYYCQQFYNYPYTFGGGTKLEIK 113
11G3-1-Light     SGSGTEFTLTISSVKAEDLAVYYCQQFYNYPYTFGGGTKLEIK 113
                 ***** *   ***  ***   ****  *  ************
```

FIG. 8B

```
                     FR1                      CDR1          FR2          CDR2         FR3
              <----------------------><------><--------------><-----><------------
                         10        20        30        40        50        60
40H3-1-Heavy  QVQLKQSGPGLVQPSQSLSITCTVSGFSLTNYGIHWLRQSPGKGLEWLGMMWRGGGTDYNAAFISRLTIT 70
3D10-1-Heavy  QVQLKQSGPGLVQPSQSLSIICTVSGFSLTRNGVHWVRQSPGKGLEWVGVIWRSGRTDYDAAFMSRLSIT 70
9G11-1-Heavy  QVQLKQSGPGLVQPSQSLSITCTVSGFSLTRNGVHWVRQSPGKGLEWVGVIWRGGRTDYDAAFMSRLSIT 70
1D9-1-Heavy   QVQLKQSGRSLVQPSQSLSITCTVSGFSLTDYGVHWIRQSPGKGLEWLGVIWRSGRTDYNAVFMSRLSIT 70
4A4-1-Heavy   QVQLKQSGRSLVQPSQSLSITCTVSGFSLTDYGVHWIRQSPGKGLEWLGVIWRSGRTDYNAVFMSRLSIT 70
11E11-1-Heavy QVQLKQSGPSLVQPSQSLSITCTVSGFSLTNYGVHWIRQSPGKGLEWLGVKWRGGRTDYNAAFMSRLSIT 70
11G3-1-Heavy  QVQLKQSGPSLVQPSQSLSITCTVSGFSLTNYGVHWVRQSPGKGLEWLGVMWRGGRTDYNAAFMSRLSIT 70
              ********  ********** ********* * **  ********** *  ** * *** * * *** **

                                        CDR3         FR4
              ------------------------><----------><--------->
                         80        90        100       110
40H3-1-Heavy  KDTSKSQVFFRMNNLQTNDTAIYYCARKGV-GMGLGYWGQGTSVTVSS 118
3D10-1-Heavy  KDNSKSQVFFKMNSLQADDTAIYYCVKNGDDGNYGTYWGQGTLVTVSA 118
9G11-1-Heavy  KDNSKSQVFFKMNSLQADDTAIYYCVKNGDDGNYGTYWGQGTLVTVSA 118
1D9-1-Heavy   KDNSKSQVFFKMNGLQTDDTAIYYCAKNGPFGNFAGYWGQGTPVAVSA 118
4A4-1-Heavy   KDNSKSQVFFKMNGLLIEDTAIYYCAKNGPFGNFAGYWGQGTPVAVSA 118
11E11-1-Heavy RDNSRSQVFFKMNSLQTDDTAIYYCAKNGPFGNFAGYWGQGTLVTVSA 118
11G3-1-Heavy  KDNSRSQVFFKMNSLQTDDAAIYYCAKNGPFGNFAGYWGQGTLVTVST 118
              * * ***** ** *   * *****   *  *    ****** * **
```

40H3 Association and Dissocation against $EGFR_{287\text{-}302}$

40H3 Association and Dissocation against EGFRwt ECD

```
                         SEQUENCE LISTING


<160> NUMBER OF SEQ ID NOS: 69

<210> SEQ ID NO 1
<211> LENGTH: 117
<212> TYPE: PRT
<213> ORGANISM: Artificial Sequence
<220> FEATURE:
<223> OTHER INFORMATION: 40H3 heavy chain variable domain

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Ile His Trp Leu Arg Gln Ser Pro Gly Lys Gly Leu Glu Trp Leu
        35                  40                  45

Gly Met Met Trp Arg Gly Gly Gly Thr Asp Tyr Asn Ala Ala Phe Ile
    50                  55                  60

Ser Arg Leu Thr Ile Thr Lys Asp Thr Ser Lys Ser Gln Val Phe Phe
65                  70                  75                  80

Arg Met Asn Asn Leu Gln Thr Asn Asp Thr Ala Ile Tyr Tyr Cys Ala
                85                  90                  95

Arg Lys Gly Val Gly Met Gly Leu Gly Tyr Trp Gly Gln Gly Thr Ser
            100                 105                 110

Val Thr Val Ser Ser
        115


<210> SEQ ID NO 2
<211> LENGTH: 107
<212> TYPE: PRT
<213> ORGANISM: Artificial Sequence
<220> FEATURE:
<223> OTHER INFORMATION: 40H3 light chain variable domain

<400> SEQUENCE: 2

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Val Ala Trp Tyr Gln Gln Lys Pro Gly Arg Ser Pro Gln Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80
```

```
Glu Asp Phe Val Ser Tyr Tyr Cys Gln Gln Leu Tyr Ser Asn Pro Tyr
                85                  90                  95

Thr Phe Gly Gly Gly Thr Lys Leu Glu Ile Lys
            100                 105


<210> SEQ ID NO 3
<211> LENGTH: 351
<212> TYPE: DNA
<213> ORGANISM: Artificial Sequence
<220> FEATURE:
<223> OTHER INFORMATION: 40H3 heavy chain variable domain nucleotide

<400> SEQUENCE: 3

caggtgcagc tgaagcagtc aggacctggc ctagtgcagc cctcacagag cctgtccatc     60

acctgcacag tctctggctt ctcattgact aactatggta ttcactggct tcgccagtct    120

ccaggaaagg gtctggagtg gctgggaatg atgtggcgtg gtggaggcac agactataat    180

gcagctttca tctccagact gactatcacc aaggacactt ccaagagcca agttttcttt    240

agaatgaaca atctgcaaac taatgacaca gccatatatt actgtgccag aaaaggggtg    300

ggaatgggtt tgggttattg gggccaagga acctcagtca ccgtctcctc a             351


<210> SEQ ID NO 4
<211> LENGTH: 321
<212> TYPE: DNA
<213> ORGANISM: Artificial Sequence
<220> FEATURE:
<223> OTHER INFORMATION: 40H3 light chain variable domain nucleotide

<400> SEQUENCE: 4

gacattcaga tgacccagtc tcctgcctcc cagtctgcat ctctgggaga aagtgtcacc     60

atcacatgcc tggcaagtca gaccattggt acatgggtag catggtatca acagaaacca    120

gggagatctc ctcagctcct gatctatggt gcaaccaact tggcagatgg ggtcccatca    180

agattcagtg gtagtggatc tggcacaaaa ttttctttca agatcagcag cctacaggct    240

gaagattttg taagctatta ctgtcaacaa ctttacagta atccgtacac gttcggaggg    300

gggaccaaac tggaaataaa g                                              321


<210> SEQ ID NO 5
<211> LENGTH: 8
<212> TYPE: PRT
<213> ORGANISM: Artificial Sequence
<220> FEATURE:
<223> OTHER INFORMATION: 40H3-1-Heavy-CDR1

<400> SEQUENCE: 5

Gly Phe Ser Leu Thr Asn Tyr Gly
1               5


<210> SEQ ID NO 6
<211> LENGTH: 7
<212> TYPE: PRT
<213> ORGANISM: Artificial Sequence
<220> FEATURE:
<223> OTHER INFORMATION: 40H3-1-Heavy-CDR2

<400> SEQUENCE: 6

Met Trp Arg Gly Gly Gly Thr
1               5


<210> SEQ ID NO 7
<211> LENGTH: 11
```

<212> TYPE: PRT
<213> ORGANISM: Artificial Sequence
<220> FEATURE:
<223> OTHER INFORMATION: 40H3-1-Heavy-CDR3

<400> SEQUENCE: 7

```
Ala Arg Lys Gly Val Gly Met Gly Leu Gly Tyr
1               5                   10
```

<210> SEQ ID NO 8
<211> LENGTH: 6
<212> TYPE: PRT
<213> ORGANISM: Artificial Sequence
<220> FEATURE:
<223> OTHER INFORMATION: 40H3-1-Light-CDR1

<400> SEQUENCE: 8

```
Gln Thr Ile Gly Thr Trp
1               5
```

<210> SEQ ID NO 9
<211> LENGTH: 3
<212> TYPE: PRT
<213> ORGANISM: Artificial Sequence
<220> FEATURE:
<223> OTHER INFORMATION: 40H3-1-Light-CDR2

<400> SEQUENCE: 9

```
Gly Ala Thr
1
```

<210> SEQ ID NO 10
<211> LENGTH: 9
<212> TYPE: PRT
<213> ORGANISM: Artificial Sequence
<220> FEATURE:
<223> OTHER INFORMATION: 40H3-1-Light-CDR3

<400> SEQUENCE: 10

```
Gln Gln Leu Tyr Ser Asn Pro Tyr Thr
1               5
```

<210> SEQ ID NO 11
<211> LENGTH: 118
<212> TYPE: PRT
<213> ORGANISM: Artificial Sequence
<220> FEATURE:
<223> OTHER INFORMATION: heavy chain variable domain for 3D10/9G11
<220> FEATURE:
<221> NAME/KEY: x
<222> LOCATION: (21)..(21)
<223> OTHER INFORMATION: I or T
<220> FEATURE:
<221> NAME/KEY: x
<222> LOCATION: (54)..(54)
<223> OTHER INFORMATION: S or G

<400> SEQUENCE: 11

```
Gln Val Gln Leu Lys Gln Ser Gly Pro Gly Leu Val Gln Pro Ser Gln
1               5                   10                  15

Ser Leu Ser Ile Xaa Cys Thr Val Ser Gly Phe Ser Leu Thr Arg Asn
            20                  25                  30

Gly Val His Trp Val Arg Gln Ser Pro Gly Lys Gly Leu Glu Trp Val
        35                  40                  45

Gly Val Ile Trp Arg Xaa Gly Arg Thr Asp Tyr Asp Ala Ala Phe Met
    50                  55                  60
```

-continued

Ser Arg Leu Ser Ile Thr Lys Asp Asn Ser Lys Ser Gln Val Phe Phe
65 70 75 80

Lys Met Asn Ser Leu Gln Ala Asp Asp Thr Ala Ile Tyr Tyr Cys Val
85 90 95

Lys Asn Gly Asp Asp Gly Asn Tyr Gly Thr Tyr Trp Gly Gln Gly Thr
100 105 110

Leu Val Thr Val Ser Ala
115

<210> SEQ ID NO 12
<211> LENGTH: 113
<212> TYPE: PRT
<213> ORGANISM: Artificial Sequence
<220> FEATURE:
<223> OTHER INFORMATION: light chain variable domain for 3D10 and 9G11

<400> SEQUENCE: 12

Asp Ile Val Met Ser Gln Ser Pro Ser Ser Leu Gly Val Ser Val Gly
1 5 10 15

Glu Lys Val Thr Met Ser Cys Lys Ser Ser Gln Ser Leu Leu Asp Ser
20 25 30

Arg Asn Gln Lys Asn Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Thr Gly Ser Gly Ser Gly Thr Glu Phe Thr Leu Thr
65 70 75 80

Ile Ser Ser Val Lys Ala Glu Asp Leu Ala Ile Tyr Tyr Cys Gln Gln
85 90 95

Tyr Tyr Asn Tyr Pro Tyr Thr Phe Gly Gly Gly Thr Lys Leu Glu Ile
100 105 110

Thr

<210> SEQ ID NO 13
<211> LENGTH: 118
<212> TYPE: PRT
<213> ORGANISM: Artificial Sequence
<220> FEATURE:
<223> OTHER INFORMATION: consensus heavy chain variable domain for 1D9/4A4
<220> FEATURE:
<221> NAME/KEY: X
<222> LOCATION: (86)..(86)
<223> OTHER INFORMATION: L or Q
<220> FEATURE:
<221> NAME/KEY: X
<222> LOCATION: (87)..(87)
<223> OTHER INFORMATION: T or I
<220> FEATURE:
<221> NAME/KEY: X
<222> LOCATION: (88)..(88)
<223> OTHER INFORMATION: D or E

<400> SEQUENCE: 13

Gln Val Gln Leu Lys Gln Ser Gly Arg Ser Leu Val Gln Pro Ser Gln
1 5 10 15

Ser Leu Ser Ile Thr Cys Thr Val Ser Gly Phe Ser Leu Thr Asp Tyr
20 25 30

Gly Val His Trp Ile Arg Gln Ser Pro Gly Lys Gly Leu Glu Trp Leu
35 40 45

Gly Val Ile Trp Arg Ser Gly Arg Thr Asp Tyr Asn Ala Val Phe Met
50 55 60

```
Ser Arg Leu Ser Ile Thr Lys Asp Asn Ser Lys Ser Gln Val Phe Phe
65                  70                  75                  80

Lys Met Asn Gly Leu Xaa Xaa Xaa Asp Thr Ala Ile Tyr Tyr Cys Ala
                85                  90                  95

Lys Asn Gly Pro Phe Gly Asn Phe Ala Gly Tyr Trp Gly Gln Gly Thr
            100                 105                 110

Pro Val Ala Val Ser Ala
        115


<210> SEQ ID NO 14
<211> LENGTH: 113
<212> TYPE: PRT
<213> ORGANISM: Artificial Sequence
<220> FEATURE:
<223> OTHER INFORMATION: consensus light chain variable domain for
      1D9/4A4
<220> FEATURE:
<221> NAME/KEY: X
<222> LOCATION: (91)..(91)
<223> OTHER INFORMATION: V or A

<400> SEQUENCE: 14

Asp Ile Val Met Ser Gln Ser Pro Ser Ser Leu Ala Val Ser Val Gly
1               5                   10                  15

Glu Lys Val Thr Met Arg Cys Arg Ser Ser Gln Ser Leu Leu Asp Ser
            20                  25                  30

Tyr His Gln Lys Asn Tyr Leu Ala Trp Tyr Leu Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Xaa Tyr Tyr Cys Gln Glu
                85                  90                  95

Tyr Tyr Arg Tyr Pro Tyr Thr Phe Gly Gly Gly Thr Lys Leu Glu Ile
            100                 105                 110

Lys


<210> SEQ ID NO 15
<211> LENGTH: 118
<212> TYPE: PRT
<213> ORGANISM: Artificial Sequence
<220> FEATURE:
<223> OTHER INFORMATION: consensus heavy chain variable domain for
      11E11/11G3
<220> FEATURE:
<221> NAME/KEY: X
<222> LOCATION: (37)..(37)
<223> OTHER INFORMATION: L or V
<220> FEATURE:
<221> NAME/KEY: X
<222> LOCATION: (51)..(51)
<223> OTHER INFORMATION: K or M
<220> FEATURE:
<221> NAME/KEY: X
<222> LOCATION: (71)..(71)
<223> OTHER INFORMATION: R or K
<220> FEATURE:
<221> NAME/KEY: X
<222> LOCATION: (90)..(90)
<223> OTHER INFORMATION: T or A
<220> FEATURE:
<221> NAME/KEY: X
<222> LOCATION: (118)..(118)
<223> OTHER INFORMATION: A or T
```

<400> SEQUENCE: 15

Gln Val Gln Leu Lys Gln Ser Gly Pro Ser Leu Val Gln Pro Ser Gln
1 5 10 15

Ser Leu Ser Ile Thr Cys Thr Val Ser Gly Phe Ser Leu Thr Asn Tyr
20 25 30

Gly Val His Trp Xaa Arg Gln Ser Pro Gly Lys Gly Leu Glu Trp Leu
35 40 45

Gly Val Xaa Trp Arg Gly Gly Arg Thr Asp Tyr Asn Ala Ala Phe Met
50 55 60

Ser Arg Leu Ser Ile Thr Xaa Asp Asn Ser Arg Ser Gln Val Phe Phe
65 70 75 80

Lys Met Asn Ser Leu Gln Thr Asp Asp Xaa Ala Ile Tyr Tyr Cys Ala
85 90 95

Lys Asn Gly Pro Phe Gly Asn Phe Ala Gly Tyr Trp Gly Gln Gly Thr
100 105 110

Leu Val Thr Val Ser Xaa
115

<210> SEQ ID NO 16
<211> LENGTH: 111
<212> TYPE: PRT
<213> ORGANISM: Artificial Sequence
<220> FEATURE:
<223> OTHER INFORMATION: consensus light chain variable domain for 11E11/11G3
<220> FEATURE:
<221> NAME/KEY: x
<222> LOCATION: (12)..(12)
<223> OTHER INFORMATION: A or P
<220> FEATURE:
<221> NAME/KEY: x
<222> LOCATION: (27)..(27)
<223> OTHER INFORMATION: Q or R

<400> SEQUENCE: 16

Asp Ile Val Met Ser Gln Ser Pro Ser Ser Leu Xaa Val Ser Val Gly
1 5 10 15

Glu Lys Val Ser Leu Thr Cys Lys Ser Ser Xaa Ser Leu Leu Asp Asn
20 25 30

Gln Lys His Tyr Leu Ala Trp Tyr Gln Gln Lys Pro Gly Gln Ser Pro
35 40 45

Lys Leu Leu Ile Tyr Trp Ala Ser Thr Arg Glu Ser Gly Val Pro Asp
50 55 60

Arg Phe Thr Gly Ser Gly Ser Gly Thr Glu Phe Thr Leu Thr Ile Ser
65 70 75 80

Ser Val Lys Ala Glu Asp Leu Ala Val Tyr Tyr Cys Gln Gln Phe Tyr
85 90 95

Asn Tyr Pro Tyr Thr Phe Gly Gly Gly Thr Lys Leu Glu Ile Lys
100 105 110

<210> SEQ ID NO 17
<211> LENGTH: 118
<212> TYPE: PRT
<213> ORGANISM: Artificial Sequence
<220> FEATURE:
<223> OTHER INFORMATION: 3D10 heavy chain variable domain

<400> SEQUENCE: 17

Gln Val Gln Leu Lys Gln Ser Gly Pro Gly Leu Val Gln Pro Ser Gln
1 5 10 15

```
Ser Leu Ser Ile Ile Cys Thr Val Ser Gly Phe Ser Leu Thr Arg Asn
            20                  25                  30

Gly Val His Trp Val Arg Gln Ser Pro Gly Lys Gly Leu Glu Trp Val
        35                  40                  45

Gly Val Ile Trp Arg Ser Gly Arg Thr Asp Tyr Asp Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Val
                85                  90                  95

Lys Asn Gly Asp Asp Gly Asn Tyr Gly Thr Tyr Trp Gly Gln Gly Thr
            100                 105                 110

Leu Val Thr Val Ser Ala
        115


<210> SEQ ID NO 18
<211> LENGTH: 354
<212> TYPE: DNA
<213> ORGANISM: Artificial Sequence
<220> FEATURE:
<223> OTHER INFORMATION: nucleic acid encoding a 3D10 heavy chain
      variable domain

<400> SEQUENCE: 18

caggtgcagc tgaagcagtc aggacctggc ctagtgcagc cctcacagag cctgtccata     60

atctgcacag tctcgggttt ctcattaact cgcaacggtg tacattgggt tcgtcagtcc    120

ccaggaaagg gtctggagtg ggtgggagtg atatggagaa gtggaaggac agactacgat    180

gcagctttca tgtccagact gagcatcacc aaggacaact ccaagagcca agttttcttt    240

aaaatgaaca gtctgcaggc tgatgacact gccatttact actgtgtcaa aaatggggac    300

gatggtaact acgggactta ctggggccaa gggactctgg tcactgtctc tgca          354


<210> SEQ ID NO 19
<211> LENGTH: 339
<212> TYPE: DNA
<213> ORGANISM: Artificial Sequence
<220> FEATURE:
<223> OTHER INFORMATION: nucleic acid encoding a 3D10 and 9G11 light
      chain variable domain

<400> SEQUENCE: 19

gacattgtga tgtcacagtc tccatcctcc ctaggtgtgt cagttggaga gaaggtgact     60

atgagctgca agtccagtca gagcctttta gatagtagga atcaaaagaa ctacttggcc    120

tggtaccagc agaaaccagg gcagtctcct aaactgctga tttactgggc atccactagg    180

gaatctgggg tccctgatcg cttcacaggc agtggatctg ggacagaatt cactctcacc    240

atcagcagtg tgaaggctga agacctggca atttattact gtcaacaata ttataactat    300

ccgtacacgt tcggaggggg gaccaagctg gaaataaca                           339


<210> SEQ ID NO 20
<211> LENGTH: 8
<212> TYPE: PRT
<213> ORGANISM: Artificial Sequence
<220> FEATURE:
<223> OTHER INFORMATION: 3D10-1-Heavy-CDR1

<400> SEQUENCE: 20

Gly Phe Ser Leu Thr Arg Asn Gly
```

1 5

<210> SEQ ID NO 21
<211> LENGTH: 7
<212> TYPE: PRT
<213> ORGANISM: Artificial Sequence
<220> FEATURE:
<223> OTHER INFORMATION: 3D10-1-Heavy-CDR2

<400> SEQUENCE: 21

Ile Trp Arg Ser Gly Arg Thr
1 5

<210> SEQ ID NO 22
<211> LENGTH: 12
<212> TYPE: PRT
<213> ORGANISM: Artificial Sequence
<220> FEATURE:
<223> OTHER INFORMATION: 3D10-1-Heavy-CDR3

<400> SEQUENCE: 22

Val Lys Asn Gly Asp Asp Gly Asn Tyr Gly Thr Tyr
1 5 10

<210> SEQ ID NO 23
<211> LENGTH: 12
<212> TYPE: PRT
<213> ORGANISM: Artificial Sequence
<220> FEATURE:
<223> OTHER INFORMATION: 3D10-1-Light-CDR1

<400> SEQUENCE: 23

Gln Ser Leu Leu Asp Ser Arg Asn Gln Lys Asn Tyr
1 5 10

<210> SEQ ID NO 24
<211> LENGTH: 3
<212> TYPE: PRT
<213> ORGANISM: Artificial Sequence
<220> FEATURE:
<223> OTHER INFORMATION: 3D10-1-Light-CDR2

<400> SEQUENCE: 24

Trp Ala Ser
1

<210> SEQ ID NO 25
<211> LENGTH: 9
<212> TYPE: PRT
<213> ORGANISM: Artificial Sequence
<220> FEATURE:
<223> OTHER INFORMATION: 3D10-1-Light-CDR3

<400> SEQUENCE: 25

Gln Gln Tyr Tyr Asn Tyr Pro Tyr Thr
1 5

<210> SEQ ID NO 26
<211> LENGTH: 118
<212> TYPE: PRT
<213> ORGANISM: Artificial Sequence
<220> FEATURE:
<223> OTHER INFORMATION: 9G11-1 heavy chain variable domain

<400> SEQUENCE: 26

Gln Val Gln Leu Lys Gln Ser Gly Pro Gly Leu Val Gln Pro Ser Gln
1 5 10 15

-continued

```
Ser Leu Ser Ile Thr Cys Thr Val Ser Gly Phe Ser Leu Thr Arg Asn
            20                  25                  30

Gly Val His Trp Val Arg Gln Ser Pro Gly Lys Gly Leu Glu Trp Val
        35                  40                  45

Gly Val Ile Trp Arg Gly Gly Arg Thr Asp Tyr Asp Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Val
                85                  90                  95

Lys Asn Gly Asp Asp Gly Asn Tyr Gly Thr Tyr Trp Gly Gln Gly Thr
            100                 105                 110

Leu Val Thr Val Ser Ala
        115


<210> SEQ ID NO 27
<211> LENGTH: 354
<212> TYPE: DNA
<213> ORGANISM: Artificial Sequence
<220> FEATURE:
<223> OTHER INFORMATION: nucleic acid sequence encoding the 9G11 heavy
      chain variable domain

<400> SEQUENCE: 27

caggtgcagc tgaagcagtc aggacctggc ctagtgcagc cctcacagag cctgtccata      60

acctgcacag tctcgggttt ctcattaact cgcaatggtg tccattgggt tcgtcagtcc     120

ccaggaaagg gtctggagtg ggtgggagtg atatggagag gtggaaggac agactacgat     180

gcagctttca tgtccagact gagcatcacc aaggacaact ccaagagcca agttttcttt     240

aaaatgaaca gtctgcaggc tgatgacact gccatttact actgtgtcaa aaatggggac     300

gatggtaatt acgggactta ctggggccaa gggactctgg tcactgtctc tgca           354


<210> SEQ ID NO 28
<211> LENGTH: 7
<212> TYPE: PRT
<213> ORGANISM: Artificial Sequence
<220> FEATURE:
<223> OTHER INFORMATION: 9G11-1-Heavy-CDR2

<400> SEQUENCE: 28

Ile Trp Arg Gly Gly Arg Thr
1               5


<210> SEQ ID NO 29
<211> LENGTH: 118
<212> TYPE: PRT
<213> ORGANISM: Artificial Sequence
<220> FEATURE:
<223> OTHER INFORMATION: 1D9 heavy chain variable domain

<400> SEQUENCE: 29

Gln Val Gln Leu Lys Gln Ser Gly Arg Ser Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Ile Arg Gln Ser Pro Gly Lys Gly Leu Glu Trp Leu
        35                  40                  45

Gly Val Ile Trp Arg Ser Gly Arg Thr Asp Tyr Asn Ala Val Phe Met
    50                  55                  60
```

```
Ser Arg Leu Ser Ile Thr Lys Asp Asn Ser Lys Ser Gln Val Phe Phe
65                  70                  75                  80

Lys Met Asn Gly Leu Gln Thr Asp Asp Thr Ala Ile Tyr Tyr Cys Ala
                85                  90                  95

Lys Asn Gly Pro Phe Gly Asn Phe Ala Gly Tyr Trp Gly Gln Gly Thr
            100                 105                 110

Pro Val Ala Val Ser Ala
        115
```

<210> SEQ ID NO 30
<211> LENGTH: 113
<212> TYPE: PRT
<213> ORGANISM: Artificial Sequence
<220> FEATURE:
<223> OTHER INFORMATION: 1D9 light chain variable domain

<400> SEQUENCE: 30

```
Asp Ile Val Met Ser Gln Ser Pro Ser Ser Leu Ala Val Ser Val Gly
1               5                   10                  15

Glu Lys Val Thr Met Arg Cys Arg Ser Ser Gln Ser Leu Leu Asp Ser
            20                  25                  30

Tyr His Gln Lys Asn Tyr Leu Ala Trp Tyr Leu Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Glu
                85                  90                  95

Tyr Tyr Arg Tyr Pro Tyr Thr Phe Gly Gly Gly Thr Lys Leu Glu Ile
            100                 105                 110

Lys
```

<210> SEQ ID NO 31
<211> LENGTH: 354
<212> TYPE: DNA
<213> ORGANISM: Artificial Sequence
<220> FEATURE:
<223> OTHER INFORMATION: nucleic acid sequence encoding a 1D9-1 heavy chain variable domain

<400> SEQUENCE: 31

```
caggtgcagc tgaagcagtc aggacgtagc ctagtgcagc cctcacagag cctgtccatc     60

acctgcacag tctctggttt ctcattaact gactatggtg tacactggat tcgtcagtct    120

ccaggaaagg gtctggagtg gctgggagtg atatggagaa gtggaagaac agactacaat    180

gcagttttca tgtccagact gagcatcacc aaggacaact ccaagagcca agttttcttt    240

aaaatgaacg gtctgcaaac tgatgacact gccatatact actgtgccaa aaatggcccc    300

tttggtaact tcgctggtta ctggggccaa ggaactccgg tcgctgtctc tgca          354
```

<210> SEQ ID NO 32
<211> LENGTH: 339
<212> TYPE: DNA
<213> ORGANISM: Artificial Sequence
<220> FEATURE:
<223> OTHER INFORMATION: nucleic acid sequence encoding the 1D9 light chain variable domain

<400> SEQUENCE: 32

```
gacattgtga tgtcccagtc tccatcctcc ctagctgtgt cagttggaga gaaggtaact     60

atgcgctgca ggtccagtca gagcctttta gatagttacc atcaaaaaaa ctacttggcc    120

tggtacctgc agaaaccagg gcagtctcct aaactgctga tttactgggc atccactagg    180

gaatctgggg tccctgatcg cttcacaggc agtggatctg ggacagattt cactctcacc    240

atcagcagtg tgaaggctga agacctggca gtttattact gtcaggaata ttataggtat    300

ccgtacacgt tcggaggggg gaccaaactg gaaataaaa                           339
```

```
<210> SEQ ID NO 33
<211> LENGTH: 8
<212> TYPE: PRT
<213> ORGANISM: Artificial Sequence
<220> FEATURE:
<223> OTHER INFORMATION: 1D9-1-Heavy-CDR1

<400> SEQUENCE: 33

Gly Phe Ser Leu Thr Asp Tyr Gly
1               5


<210> SEQ ID NO 34
<211> LENGTH: 7
<212> TYPE: PRT
<213> ORGANISM: Artificial Sequence
<220> FEATURE:
<223> OTHER INFORMATION: 1D9-1-Heavy-CDR2

<400> SEQUENCE: 34

Ile Trp Arg Ser Gly Arg Thr
1               5


<210> SEQ ID NO 35
<211> LENGTH: 12
<212> TYPE: PRT
<213> ORGANISM: Artificial Sequence
<220> FEATURE:
<223> OTHER INFORMATION: 1D9-1-Heavy-CDR3

<400> SEQUENCE: 35

Ala Lys Asn Gly Pro Phe Gly Asn Phe Ala Gly Tyr
1               5                   10


<210> SEQ ID NO 36
<211> LENGTH: 12
<212> TYPE: PRT
<213> ORGANISM: Artificial Sequence
<220> FEATURE:
<223> OTHER INFORMATION: 1D9-1-Light-CDR1

<400> SEQUENCE: 36

Gln Ser Leu Leu Asp Ser Tyr His Gln Lys Asn Tyr
1               5                   10


<210> SEQ ID NO 37
<211> LENGTH: 3
<212> TYPE: PRT
<213> ORGANISM: Artificial Sequence
<220> FEATURE:
<223> OTHER INFORMATION: 1D9-1-Light-CDR2

<400> SEQUENCE: 37

Trp Ala Ser
1
```

<210> SEQ ID NO 38
<211> LENGTH: 9
<212> TYPE: PRT
<213> ORGANISM: Artificial Sequence
<220> FEATURE:
<223> OTHER INFORMATION: 1D9-1-Light-CDR3

<400> SEQUENCE: 38

```
Gln Glu Tyr Tyr Arg Tyr Pro Tyr Thr
1               5
```

<210> SEQ ID NO 39
<211> LENGTH: 118
<212> TYPE: PRT
<213> ORGANISM: Artificial Sequence
<220> FEATURE:
<223> OTHER INFORMATION: 4A4 heavy chain variable domain

<400> SEQUENCE: 39

```
Gln Val Gln Leu Lys Gln Ser Gly Arg Ser Leu Val Gln Pro Ser Gln
1               5                   10                  15

Ser Leu Ser Ile Thr Cys Thr Val Ser Gly Phe Ser Leu Thr Asp Tyr
            20                  25                  30

Gly Val His Trp Ile Arg Gln Ser Pro Gly Lys Gly Leu Glu Trp Leu
        35                  40                  45

Gly Val Ile Trp Arg Ser Gly Arg Thr Asp Tyr Asn Ala Val Phe Met
    50                  55                  60

Ser Arg Leu Ser Ile Thr Lys Asp Asn Ser Lys Ser Gln Val Phe Phe
65                  70                  75                  80

Lys Met Asn Gly Leu Leu Ile Glu Asp Thr Ala Ile Tyr Tyr Cys Ala
                85                  90                  95

Lys Asn Gly Pro Phe Gly Asn Phe Ala Gly Tyr Trp Gly Gln Gly Thr
            100                 105                 110

Pro Val Ala Val Ser Ala
        115
```

<210> SEQ ID NO 40
<211> LENGTH: 113
<212> TYPE: PRT
<213> ORGANISM: Artificial Sequence
<220> FEATURE:
<223> OTHER INFORMATION: 4A4 light chain variable domain

<400> SEQUENCE: 40

```
Asp Ile Val Met Ser Gln Ser Pro Ser Ser Leu Ala Val Ser Val Gly
1               5                   10                  15

Glu Lys Val Thr Met Arg Cys Arg Ser Ser Gln Ser Leu Leu Asp Ser
            20                  25                  30

Tyr His Gln Lys Asn Tyr Leu Ala Trp Tyr Leu Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Ala Tyr Tyr Cys Gln Glu
                85                  90                  95

Tyr Tyr Arg Tyr Pro Tyr Thr Phe Gly Gly Gly Thr Lys Leu Glu Ile
            100                 105                 110

Lys
```

<210> SEQ ID NO 41
<211> LENGTH: 354
<212> TYPE: DNA
<213> ORGANISM: Artificial Sequence
<220> FEATURE:
<223> OTHER INFORMATION: 4A4 heavy chain variable domain

<400> SEQUENCE: 41
caggtgcagc tgaagcagtc aggacgtagc ctagtgcagc cctcacagag cctgtccatc 60
acctgcacag tctctggttt ctcattaact gactatggtg tacactggat tcgtcagtct 120
ccaggaaagg gtctggagtg gctgggagtg atatggagaa gtggaagaac agactacaat 180
gcagttttca tgtccagact gagcatcacc aaggacaact ccaagagcca agttttcttt 240
aaaatgaacg gtctgctaat tgaagacact gccatatact actgtgccaa aaatggcccc 300
tttggtaatt tcgctggtta ctggggccaa ggaactccgg tcgctgtctc tgca 354

<210> SEQ ID NO 42
<211> LENGTH: 339
<212> TYPE: DNA
<213> ORGANISM: Artificial Sequence
<220> FEATURE:
<223> OTHER INFORMATION: nucleic acid sequence encoding the 4A4 light
chain variable domain

<400> SEQUENCE: 42
gacattgtga tgtcccagtc tccatcctcc ctagctgtgt cagttggaga gaaggtaact 60
atgcgctgca ggtccagtca gagcctttta gatagttacc atcaaaagaa ctacttggcc 120
tggtacctgc agaaaccagg gcagtctcct aaactgctga tttactgggc atccactagg 180
gaatctgggg tccctgatcg cttcacaggc agtggatctg ggacagattt cactctcacc 240
atcagcagtg tgaaggctga agacctggca gcttattact gtcaggaata ttataggtat 300
ccgtacacgt tcggaggggg gaccaaactg gaaataaaa 339

<210> SEQ ID NO 43
<211> LENGTH: 118
<212> TYPE: PRT
<213> ORGANISM: Artificial Sequence
<220> FEATURE:
<223> OTHER INFORMATION: 11E11 heavy chain variable domain

<400> SEQUENCE: 43

Gln Val Gln Leu Lys Gln Ser Gly Pro Ser Leu Val Gln Pro Ser Gln
1 5 10 15

Ser Leu Ser Ile Thr Cys Thr Val Ser Gly Phe Ser Leu Thr Asn Tyr
20 25 30

Gly Val His Trp Ile Arg Gln Ser Pro Gly Lys Gly Leu Glu Trp Leu
35 40 45

Gly Val Lys Trp Arg Gly Gly Arg Thr Asp Tyr Asn Ala Ala Phe Met
50 55 60

Ser Arg Leu Ser Ile Thr Arg Asp Asn Ser Arg Ser Gln Val Phe Phe
65 70 75 80

Lys Met Asn Ser Leu Gln Thr Asp Asp Thr Ala Ile Tyr Tyr Cys Ala
85 90 95

Lys Asn Gly Pro Phe Gly Asn Phe Ala Gly Tyr Trp Gly Gln Gly Thr
100 105 110

Leu Val Thr Val Ser Ala
115

<210> SEQ ID NO 44
<211> LENGTH: 111
<212> TYPE: PRT
<213> ORGANISM: Artificial Sequence
<220> FEATURE:
<223> OTHER INFORMATION: 11E11 light chain variable domain.

<400> SEQUENCE: 44

```
Asp Ile Val Met Ser Gln Ser Pro Ser Ser Leu Ala Val Ser Val Gly
1               5                   10                  15

Glu Lys Val Ser Leu Thr Cys Lys Ser Ser Gln Ser Leu Leu Asp Asn
            20                  25                  30

Gln Lys His Tyr Leu Ala Trp Tyr Gln Gln Lys Pro Gly Gln Ser Pro
        35                  40                  45

Lys Leu Leu Ile Tyr Trp Ala Ser Thr Arg Glu Ser Gly Val Pro Asp
    50                  55                  60

Arg Phe Thr Gly Ser Gly Ser Gly Thr Glu Phe Thr Leu Thr Ile Ser
65                  70                  75                  80

Ser Val Lys Ala Glu Asp Leu Ala Val Tyr Tyr Cys Gln Gln Phe Tyr
                85                  90                  95

Asn Tyr Pro Tyr Thr Phe Gly Gly Gly Thr Lys Leu Glu Ile Lys
            100                 105                 110
```

<210> SEQ ID NO 45
<211> LENGTH: 354
<212> TYPE: DNA
<213> ORGANISM: Artificial Sequence
<220> FEATURE:
<223> OTHER INFORMATION: nucleic acid encoding the 11E11 heavy chain
      variable domain

<400> SEQUENCE: 45

```
caggtgcagc tgaagcagtc aggacctagc ctagtgcagc cctcacagag cctgtccata     60

acctgcacag tctctggttt ctcattaact aactatggtg tacactggat tcgccagtct    120

ccaggaaagg gtctggagtg gctgggagtg aagtggagag gtggacgcac agactacaat    180

gcagctttca tgtccagact gagcatcacc agggacaact ccaggagcca agttttcttt    240

aaaatgaaca gtctccaaac tgatgacact gccatatact actgtgccaa aaatggcccc    300

tttggtaact tcgctggtta ttggggccaa gggactctgg tcactgtctc tgca          354
```

<210> SEQ ID NO 46
<211> LENGTH: 333
<212> TYPE: DNA
<213> ORGANISM: Artificial Sequence
<220> FEATURE:
<223> OTHER INFORMATION: nucleic acid encoding the 11E11 light chain
      variable domain

<400> SEQUENCE: 46

```
gacattgtga tgtcacagtc tccatcctcc ctagctgtgt cagttggaga gaaggttagt     60

ctgacctgca agtccagtca gagcctttta gacaatcaaa agcactactt ggcctggtac    120

cagcagaaac cagggcagtc tcctaaactg ctgatttact gggcatccac tagggaatct    180

ggggtccctg atcgcttcac aggcagtgga tctgggacag aattcactct cactatcagc    240

agtgtgaagg ctgaagacct ggcagtttat tactgtcagc aattttataa ctatccgtac    300

acgttcggag gggggaccaa gctggaaata aaa                                 333
```

<210> SEQ ID NO 47

<211> LENGTH: 8
<212> TYPE: PRT
<213> ORGANISM: Artificial Sequence
<220> FEATURE:
<223> OTHER INFORMATION: 11E11-1-Heavy-CDR1

<400> SEQUENCE: 47

Gly Phe Ser Leu Thr Asn Tyr Gly
1 5

<210> SEQ ID NO 48
<211> LENGTH: 7
<212> TYPE: PRT
<213> ORGANISM: Artificial Sequence
<220> FEATURE:
<223> OTHER INFORMATION: 11E11-1-Heavy-CDR2

<400> SEQUENCE: 48

Lys Trp Arg Gly Gly Arg Thr
1 5

<210> SEQ ID NO 49
<211> LENGTH: 12
<212> TYPE: PRT
<213> ORGANISM: Artificial Sequence
<220> FEATURE:
<223> OTHER INFORMATION: 11E11-1-Heavy-CDR3

<400> SEQUENCE: 49

Ala Lys Asn Gly Pro Phe Gly Asn Phe Ala Gly Tyr
1 5 10

<210> SEQ ID NO 50
<211> LENGTH: 12
<212> TYPE: PRT
<213> ORGANISM: Artificial Sequence
<220> FEATURE:
<223> OTHER INFORMATION: 11E11-1-Light-CDR1

<400> SEQUENCE: 50

Ser Ser Gln Ser Leu Leu Asp Asn Gln Lys His Tyr
1 5 10

<210> SEQ ID NO 51
<211> LENGTH: 3
<212> TYPE: PRT
<213> ORGANISM: Artificial Sequence
<220> FEATURE:
<223> OTHER INFORMATION: 11E11-1-Light-CDR2

<400> SEQUENCE: 51

Trp Ala Ser
1

<210> SEQ ID NO 52
<211> LENGTH: 9
<212> TYPE: PRT
<213> ORGANISM: Artificial Sequence
<220> FEATURE:
<223> OTHER INFORMATION: 11E11-1-Light-CDR3

<400> SEQUENCE: 52

Gln Gln Phe Tyr Asn Tyr Pro Tyr Thr
1 5

<210> SEQ ID NO 53
<211> LENGTH: 118

<212> TYPE: PRT
<213> ORGANISM: Artificial Sequence
<220> FEATURE:
<223> OTHER INFORMATION: 11G3 heavy chain variable domain

<400> SEQUENCE: 53

```
Gln Val Gln Leu Lys Gln Ser Gly Pro Ser Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Met Trp Arg Gly Gly Arg Thr Asp Tyr Asn Ala Ala Phe Met
    50                  55                  60

Ser Arg Leu Ser Ile Thr Lys Asp Asn Ser Arg Ser Gln Val Phe Phe
65                  70                  75                  80

Lys Met Asn Ser Leu Gln Thr Asp Asp Ala Ala Ile Tyr Tyr Cys Ala
                85                  90                  95

Lys Asn Gly Pro Phe Gly Asn Phe Ala Gly Tyr Trp Gly Gln Gly Thr
            100                 105                 110

Leu Val Thr Val Ser Thr
        115
```

<210> SEQ ID NO 54
<211> LENGTH: 113
<212> TYPE: PRT
<213> ORGANISM: Artificial Sequence
<220> FEATURE:
<223> OTHER INFORMATION: 11G3 light chain variable domain

<400> SEQUENCE: 54

```
Cys Gly Asp Ile Val Met Ser Gln Ser Pro Ser Ser Leu Pro Val Ser
1               5                   10                  15

Val Gly Glu Lys Val Ser Leu Thr Cys Lys Ser Ser Arg Ser Leu Leu
            20                  25                  30

Asp Asn Gln Lys His Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Glu Phe Thr Leu Thr
65                  70                  75                  80

Ile Ser Ser Val Lys Ala Glu Asp Leu Ala Val Tyr Tyr Cys Gln Gln
                85                  90                  95

Phe Tyr Asn Tyr Pro Tyr Thr Phe Gly Gly Gly Thr Lys Leu Glu Ile
            100                 105                 110

Lys
```

<210> SEQ ID NO 55
<211> LENGTH: 354
<212> TYPE: DNA
<213> ORGANISM: Artificial Sequence
<220> FEATURE:
<223> OTHER INFORMATION: nucleic acid sequence encoding an 11G3 heavy chain variable domain

<400> SEQUENCE: 55

```
caggtgcagc tgaagcagtc aggacctagc ctagtgcagc cctcacagag cctgtccata     60

acctgcacag tctctggttt ctcattaact aactatggtg tacactgggt tcgccagtct    120
```

-continued

```
ccaggaaagg gtctggagtg gctgggagtc atgtggagag gtggacgcac agactacaat    180

gcagctttca tgtccagact gagcatcacc aaggacaact ccaggagcca agttttcttt    240

aaaatgaaca gtctgcaaac tgatgacgct gccatatact actgtgccaa aaatggcccc    300

tttggaaact tcgctggtta ttggggccaa gggactctgg tcactgtctc taca          354
```

<210> SEQ ID NO 56
<211> LENGTH: 339
<212> TYPE: DNA
<213> ORGANISM: Artificial Sequence
<220> FEATURE:
<223> OTHER INFORMATION: nucleic acid sequence encoding an 11G3 light chain variable domain

<400> SEQUENCE: 56

```
tgtggggaca ttgtgatgtc acagtctcca tcctccctac ctgtgtcagt tggagagaag     60

gttagtctga cctgcaagtc cagtcggagc cttttagaca atcagaagca ctacttggcc    120

tggtaccagc agaaaccagg gcagtctcct aaactgctga tttactgggc atccactagg    180

gaatctgggg tccctgatcg cttcacaggc agtggatctg ggacagaatt cactctcact    240

atcagcagtg tgaaggctga agacctggca gtttattact gtcagcaatt ttataactat    300

ccgtacacgt tcggaggggg gaccaagctg gaaataaaa                           339
```

<210> SEQ ID NO 57
<211> LENGTH: 7
<212> TYPE: PRT
<213> ORGANISM: Artificial Sequence
<220> FEATURE:
<223> OTHER INFORMATION: 11G3-1-Heavy-CDR2

<400> SEQUENCE: 57

```
Met Trp Arg Gly Gly Arg Thr
1               5
```

<210> SEQ ID NO 58
<211> LENGTH: 12
<212> TYPE: PRT
<213> ORGANISM: Artificial Sequence
<220> FEATURE:
<223> OTHER INFORMATION: 11G3-1-Light-CDR1

<400> SEQUENCE: 58

```
Ser Ser Arg Ser Leu Leu Asp Asn Gln Lys His Tyr
1               5                   10
```

<210> SEQ ID NO 59
<211> LENGTH: 14
<212> TYPE: PRT
<213> ORGANISM: Artificial Sequence
<220> FEATURE:
<223> OTHER INFORMATION: linker

<400> SEQUENCE: 59

```
Gly Gly Gly Gly Ser Gly Gly Gly Gly Ser Gly Gly Gly Gly
1               5                   10
```

<210> SEQ ID NO 60
<211> LENGTH: 22
<212> TYPE: PRT
<213> ORGANISM: Artificial Sequence
<220> FEATURE:
<223> OTHER INFORMATION: granulocyte-macrophage colony-stimulating factor signal peptide

<400> SEQUENCE: 60

Leu Leu Val Thr Ser Leu Leu Leu Cys Glu Leu Pro His Pro Ala Phe
1 5 10 15

Leu Leu Ile Pro Asp Thr
20

<210> SEQ ID NO 61
<211> LENGTH: 236
<212> TYPE: PRT
<213> ORGANISM: Homo sapiens

<400> SEQUENCE: 61

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys Lys Asp Pro Lys
225 230 235

<210> SEQ ID NO 62
<211> LENGTH: 69
<212> TYPE: PRT
<213> ORGANISM: Artificial Sequence
<220> FEATURE:
<223> OTHER INFORMATION: CD8 transmembrane domain

<400> SEQUENCE: 62

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp Ile Tyr Ile
35 40 45

```
Trp Ala Pro Leu Ala Gly Thr Cys Gly Val Leu Leu Leu Ser Leu Val
    50                  55                  60

Ile Thr Leu Tyr Cys
65


<210> SEQ ID NO 63
<211> LENGTH: 67
<212> TYPE: PRT
<213> ORGANISM: Artificial Sequence
<220> FEATURE:
<223> OTHER INFORMATION: CD28 transmembrane domain

<400> SEQUENCE: 63

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg
65


<210> SEQ ID NO 64
<211> LENGTH: 112
<212> TYPE: PRT
<213> ORGANISM: Artificial Sequence
<220> FEATURE:
<223> OTHER INFORMATION: CD3 zeta signaling domain

<400> SEQUENCE: 64

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 65
<211> LENGTH: 84
<212> TYPE: PRT
<213> ORGANISM: Artificial Sequence
<220> FEATURE:
<223> OTHER INFORMATION: signalling domain

<400> SEQUENCE: 65

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30
```

-continued

```
Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg


<210> SEQ ID NO 66
<211> LENGTH: 40
<212> TYPE: PRT
<213> ORGANISM: Artificial Sequence
<220> FEATURE:
<223> OTHER INFORMATION: signalling domain

<400> SEQUENCE: 66

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40


<210> SEQ ID NO 67
<211> LENGTH: 42
<212> TYPE: PRT
<213> ORGANISM: Artificial Sequence
<220> FEATURE:
<223> OTHER INFORMATION: signalling domain

<400> SEQUENCE: 67

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 68
<211> LENGTH: 47
<212> TYPE: PRT
<213> ORGANISM: Artificial Sequence
<220> FEATURE:
<223> OTHER INFORMATION: signaling domain.

<400> SEQUENCE: 68

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Glu Gly Gly Cys Glu Leu
        35                  40                  45


<210> SEQ ID NO 69
<211> LENGTH: 16
<212> TYPE: PRT
<213> ORGANISM: Homo sapiens

<400> SEQUENCE: 69

Cys Gly Ala Asp Ser Tyr Glu Met Glu Glu Asp Gly Val Arg Lys Cys
1               5                   10                  15
```

MONOCLONAL ANTIBODIES THAT BIND EGFRvIII AND THEIR USE

CROSS REFERENCE TO RELATED APPLICATION

This is a § 371 U.S. national stage of International Application No. PCT/US2020/040544, filed Jul. 1, 2020, which claims the benefit of U.S. Provisional Application No. 62/869,956, filed Jul. 2, 2019, which is incorporated by reference herein in its entirety.

STATEMENT OF GOVERNMENT SUPPORT

This invention was made with Government support under project number Z01 #: Z1A BC 008757 by the National Institutes of Health, National Cancer Institute. The United States Government has certain rights in the invention.

FIELD OF THE DISCLOSURE

This related to the field of cancer biology, specifically to monoclonal antibodies and antigen binding fragments thereof that specifically bind the human epidermal growth factor receptor (EGFR) variant III (vIII).

BACKGROUND

EGFR is frequently involved in the oncogenic progression of human cancer. Various alterations in expression including gene amplifications and activating mutations contribute to oncogenesis. This large receptor has an external domain (ECD) of 621 amino acids, a single pass transmembrane domain (TM) of 23 amino acids and an enzymatically active intracellular domain (ICD) of 542 amino acids. The EGFR is a member of the receptor tyrosine kinase family and was the first receptor shown to be associated positively with human cancer. Ligand binding leads to receptor dimer formation and the activation of the kinase domain which signals to one of several pathways that can promote the growth, survival and spread of mammalian cells. Activating mutations can occur in either the ECD or the ICD; there are also gene amplifications and large deletions exemplified by the loss of exons 2-7 to produce EGFR variant (v) III or the loss of exon 19 to generate a constitutively active enzyme mutant. The expression of EGFRvIII or the loss of exon 19 are reported for cancer cells only. A need remains for antibodies that can bind EGFRvIII, but not wild-type EGFR.

SUMMARY OF THE DISCLOSURE

Disclosed are isolated monoclonal antibodies and antigen binding fragments thereof, wherein the monoclonal antibody specifically binds to EGFRvIII. In some embodiments, the monoclonal antibody or antigen binding fragment include a) a heavy chain variable region ($V_H$) and a light chain variable region ($V_L$) comprising a heavy chain complementarity determining region (HCDR)1, a HCDR2, and a HCDR3, and a light chain complementarity determining region (LCDR)1, a LCDR2, and a LCDR3 of the $V_H$ and $V_L$ set forth as SEQ ID NOs: 1 and 2, respectively; b) a $V_H$ and an $V_L$ comprising a HCDR1, a HCDR2, and a HCDR3, and a LCDR1, a LCDR2, and a LCDR3 of the $V_H$ and $V_L$ set forth as SEQ ID NOs: 11 and 12, respectively; c) a $V_H$ and a $V_L$ comprising a HCDR1, a HCDR2, and a HCDR3, and a LCDR1, a LCDR2, and a LCDR3 of the $V_H$ and $V_L$ set forth as SEQ ID NOs: 13 and 14, respectively; or d) a $V_H$ and a $V_L$ comprising a HCDR1, a HCDR2, and a HCDR3, and a LCDR1, a LCDR2, and a LCDR3 of the $V_H$ and $V_L$ set forth as SEQ ID NOs: 15 and 16, respectively.

In some embodiments, the isolated monoclonal antibody or antigen binding fragment thereof of claim 1, includes: a) a $V_H$ and a $V_L$ comprising a HCDR1, a HCDR2, and a HCDR3, and a LCDR1, a LCDR2, and a LCDR3 of the $V_H$ and $V_L$ set forth as SEQ ID NOs: 17 and 12, respectively; b) a $V_H$ and a $V_L$ comprising a HCDR1, a HCDR2, and a HCDR3, and a LCDR1, a LCDR2, and a LCDR3 of the $V_H$ and $V_L$ set forth as SEQ ID NOs: 26 and 12, respectively; c) a $V_H$ and a $V_L$ comprising a HCDR1, a HCDR2, and a HCDR3, and a LCDR1, a LCDR2, and a LCDR3 of the $V_H$ and $V_L$ set forth as SEQ ID NOs: 29 and 30, respectively; d) a $V_H$ and an $V_L$ comprising a HCDR1, a HCDR2, and a HCDR3, and a LCDR1, a LCDR2, and a LCDR3 of the $V_H$ and $V_L$ set forth as set forth as SEQ ID NOs: 39 and 40, respectively; e) a $V_H$ and an $V_L$ comprising a HCDR1, a HCDR2, and a HCDR3, and a LCDR1, a LCDR2, and a LCDR3 of the $V_H$ and $V_L$ set forth as SEQ ID NOs: 43 and 44, respectively; or f) a $V_H$ and an $V_L$ comprising a HCDR1, a HCDR2, and a HCDR3, and a LCDR1, a LCDR2, and a LCDR3 of the $V_H$ and $V_L$ set forth as SEQ ID NOs: 53 and 54, respectively.

In other embodiments conjugates of these antibodies and antigen binding fragments are disclosed. In yet other embodiments, chimeric antigen receptors including these antibodies or antigen binding fragments are disclosed. In more embodiments, T cells expressing these chimeric antigen receptors are disclosed.

In some embodiments, disclosed are nucleic acid molecules encoding a $V_H$ and/or a $V_L$ of these monoclonal antibodies, vectors including these nucleic acids, and host cells transformed with these nucleic acid molecule and/or vectors.

In further embodiments, disclosed is the use of these monoclonal antibodies for inhibiting a tumor that expresses EGFRvIII in a subject. In other embodiments, disclosed is the use of these monoclonal antibodies for detecting EGFRvIII.

The foregoing and other features and advantages of the invention will become more apparent from the following detailed description of several embodiments which proceeds with reference to the accompanying figures.

BRIEF DESCRIPTION OF THE FIGURES

FIGS. 6A-6C. Reactivity of purified monoclonal antibodies on intact cells using flow cytometry. A. MDA-MB-468; A431 B. $F98_{EGFR}$; $F98_{npEGFRvIII}$; C. WI-38.

FIGS. 8A-8B. Alignment of the acid sequences of antibodies deduced from variable cDNA gene sequences. The $V_L$ for each antibody is listed as the antibody name followed by "1-light" in FIG. 8A (SEQ ID NOs: 2, 12, 30, 40, 44 and 54), and the $V_H$ for each antibody is listed as the antibody name followed by "1-heavy" in FIG. 8B (SEQ ID NOs: 1, 17, 26, 29, 39, 43 and 53). Shown are the following sequences:

40H3: $V_H$ and the $V_L$ are SEQ ID NOs: 1 and 2;
3D10: $V_H$ and the $V_L$ are SEQ ID NOs: 17 and 12;
9G11: $V_H$ and the $V_L$ are SEQ ID NOs: 26 and 12;
1D9: $V_H$ and the $V_L$ are SEQ ID NOs: 29 and 30;
4A4: $V_H$ and the $V_L$ are SEQ ID NOs: 39 and 40;
11E11: $V_H$ and the $V_L$ are SEQ ID NOs: 43 and 44; and
11G3: $V_H$ and the $V_L$ are SEQ ID NOs: 53 and 54.

Figure 9:
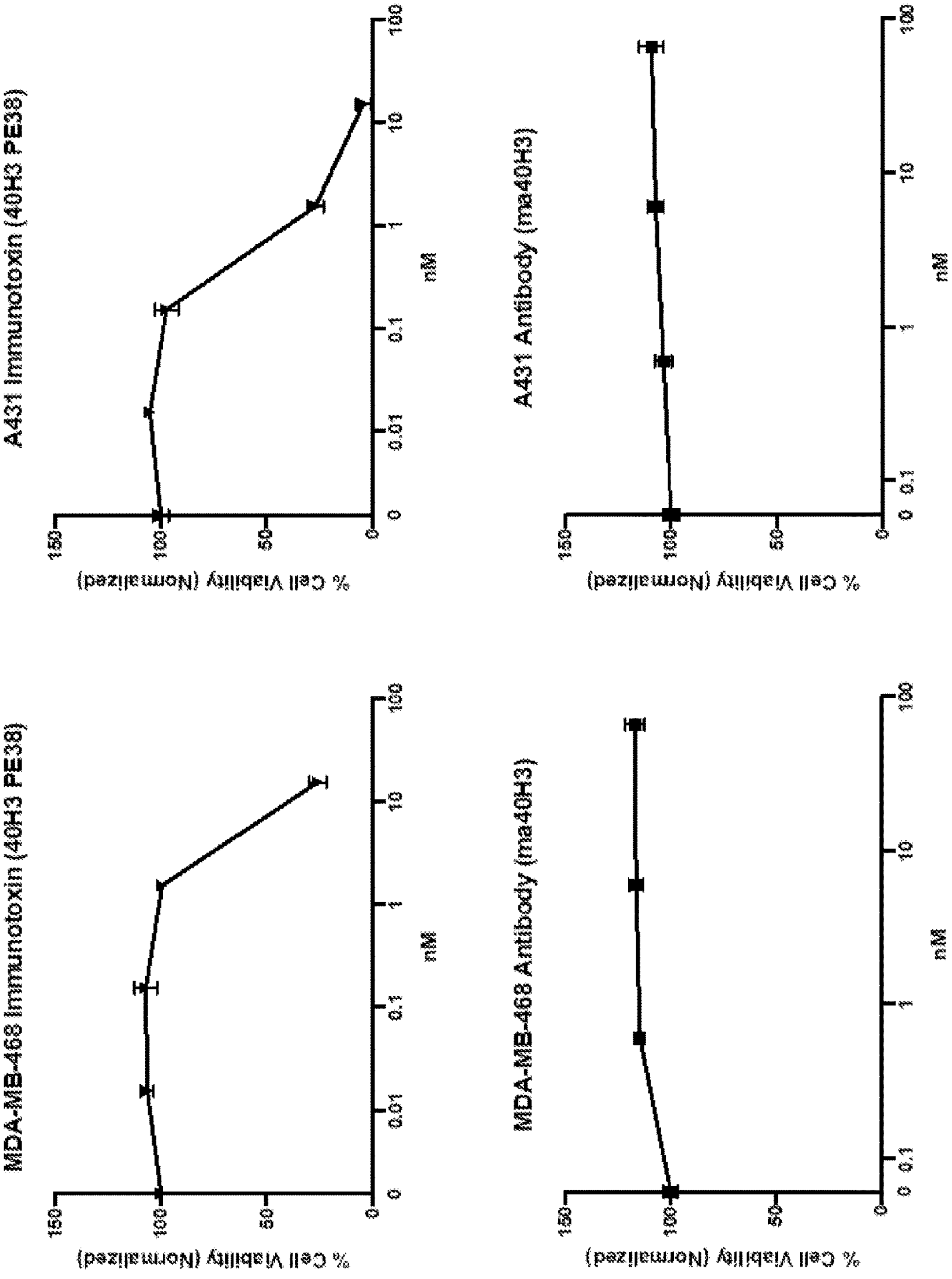

FIG. 9. Cytotoxicity of antibody and immunotoxin protein for cancer cell lines.

Figure 10A:
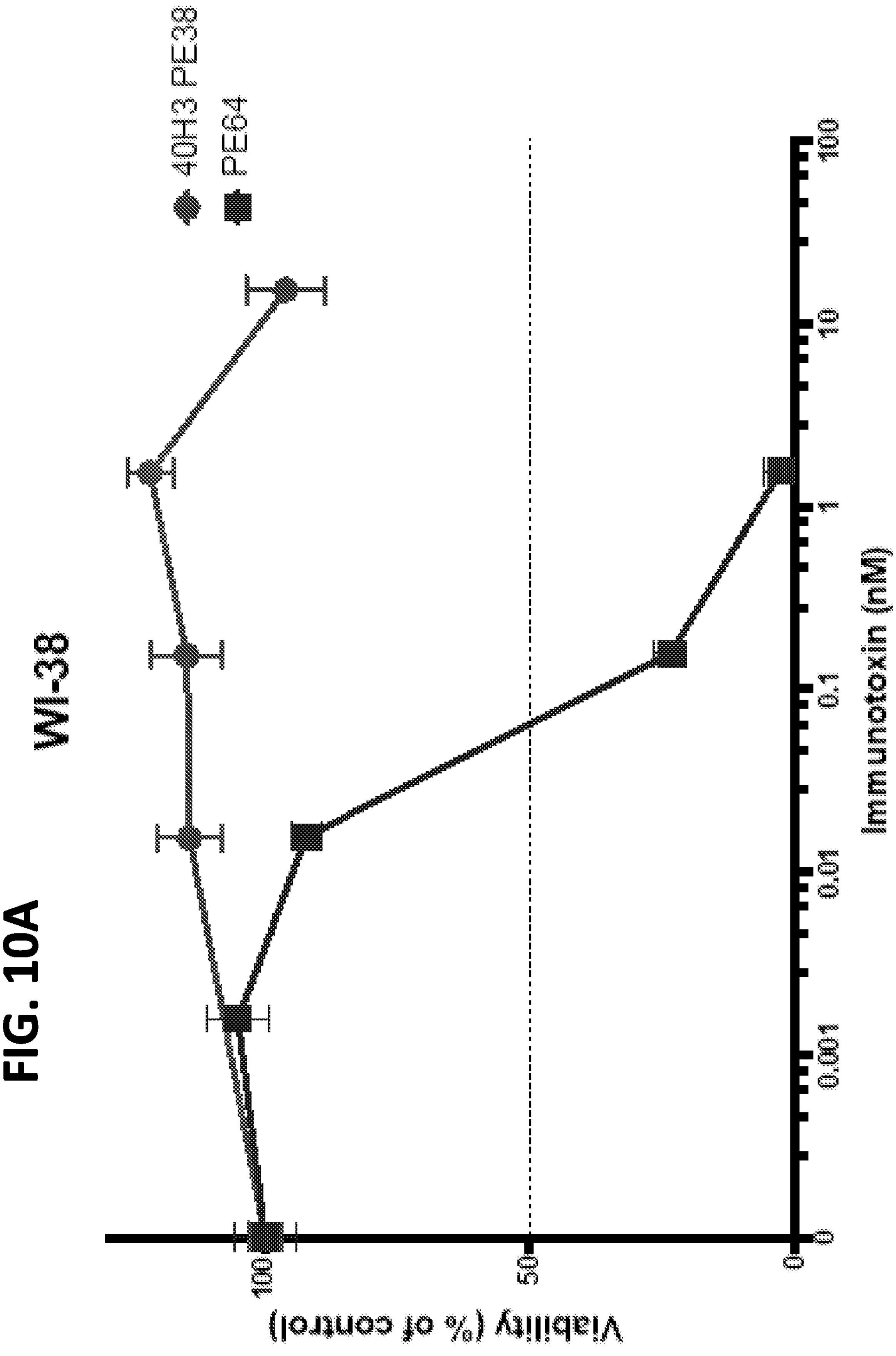
Figure 10B:
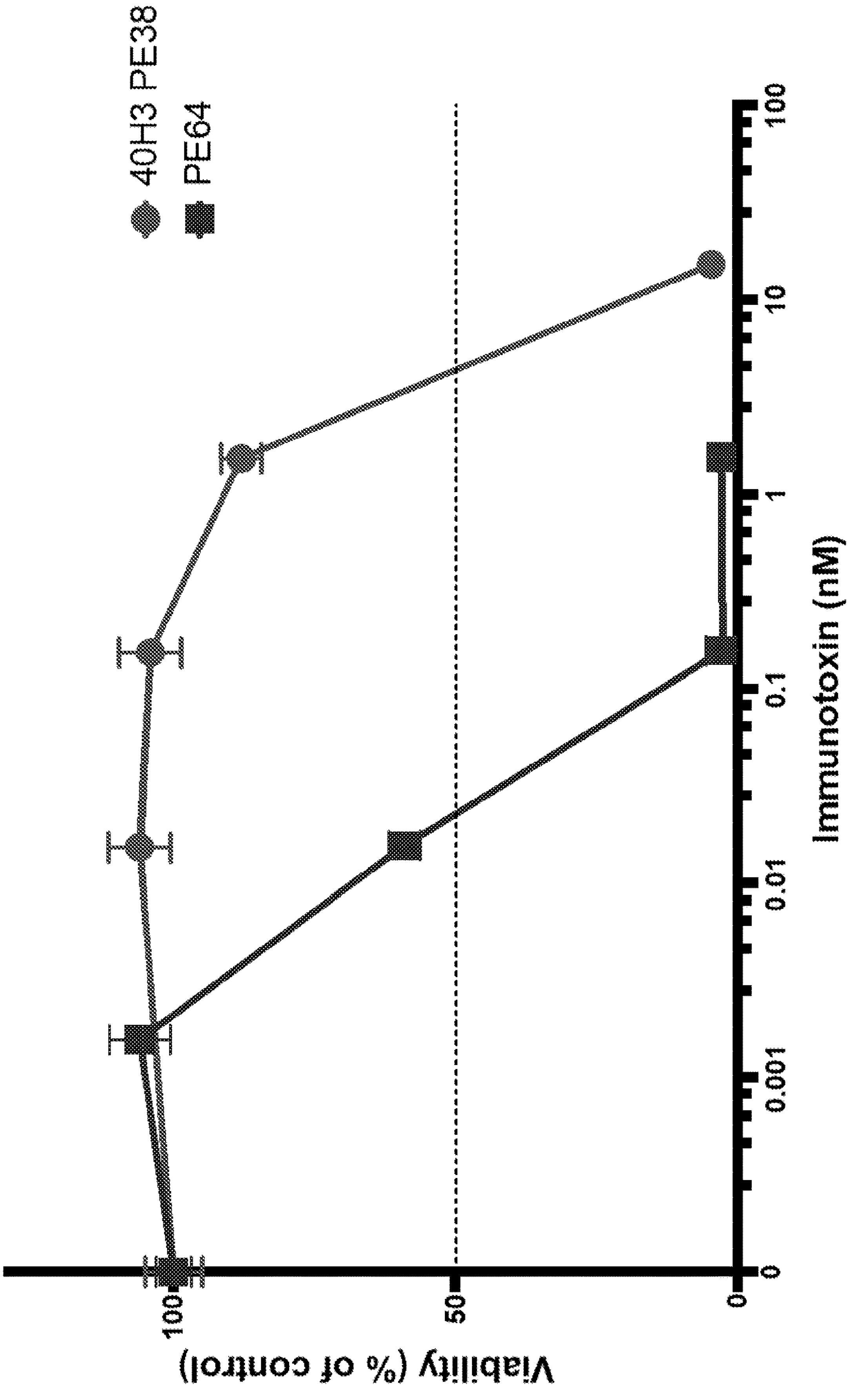
Figure 10C:
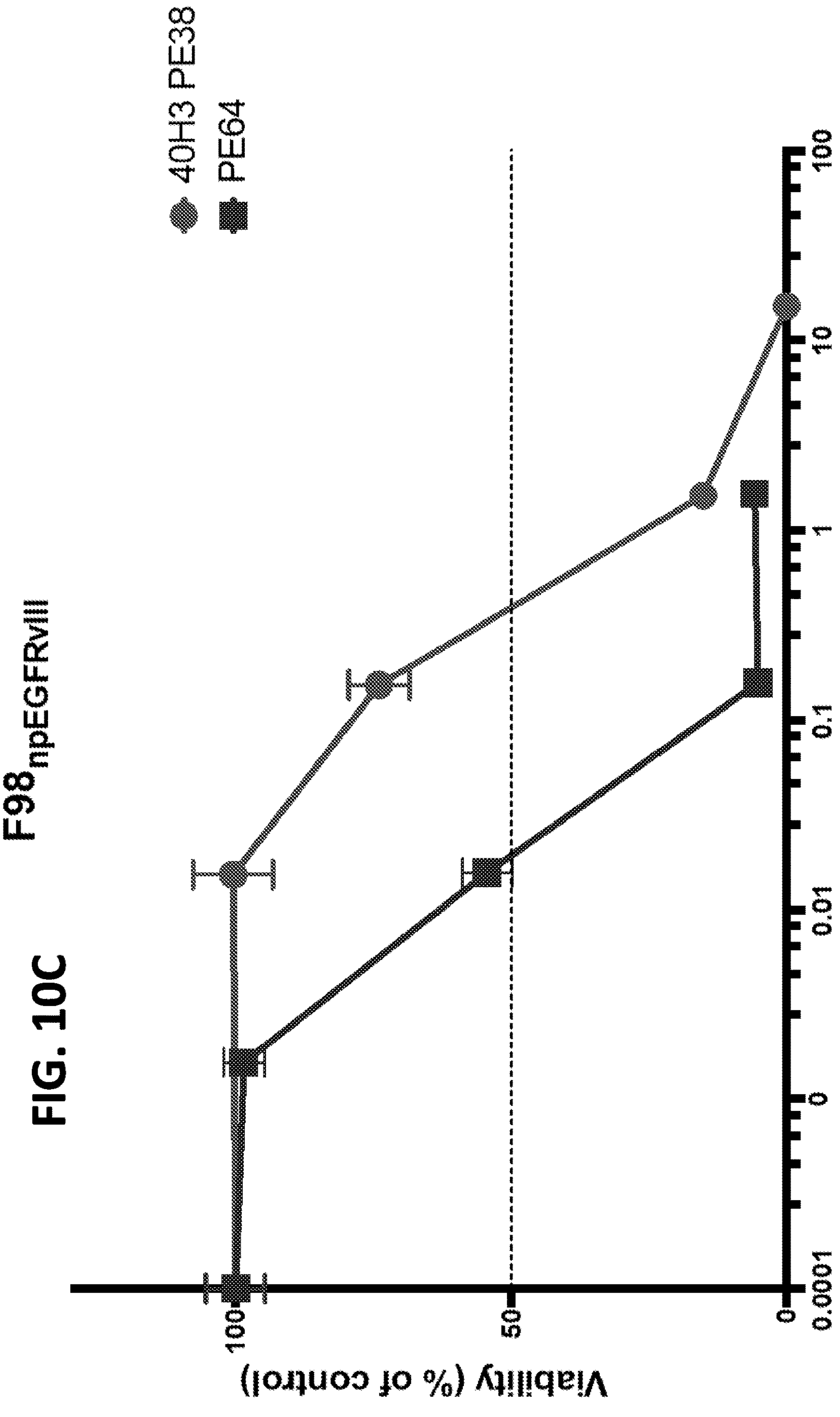

FIGS. 10A-10C. Dose response curves of cell viability following the addition of 40H3-PE38 (immunotoxin) or PE64 (native toxin) to WI-38 cells, $F98_{EGFR}$ cells or $F98_{npEGFRvIII}$ cells. WI-38 is a normal lung fibroblast cell line; '$F98_{EGFR}$' is a rat glioma cell line transfected with full-length EGFR and $F98_{npEGFRvIII}$ is a rat glioma cell line transfected with nonphosphorylated EGFRvIII.

Figure 11A:
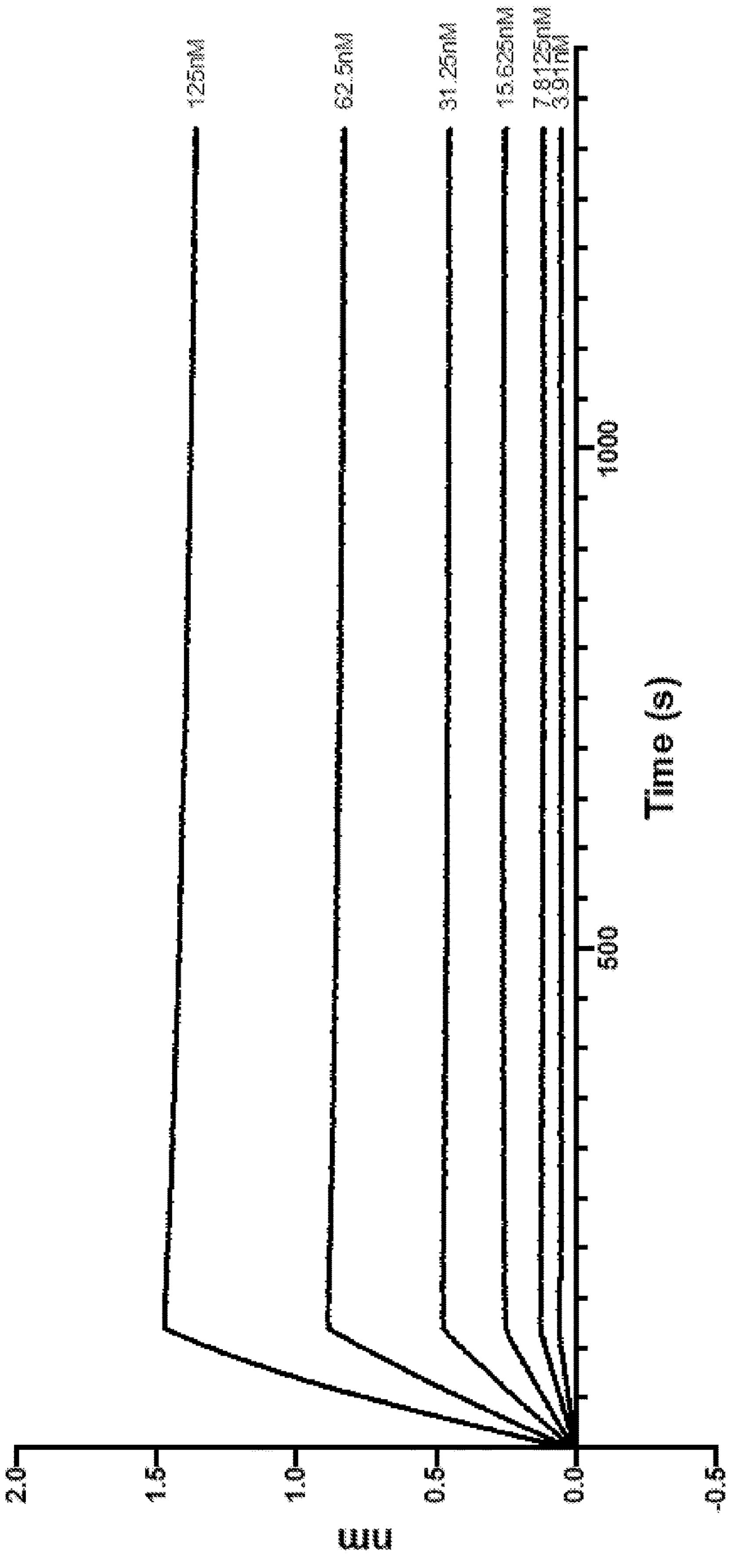
Figure 11B:
Figure 11C:
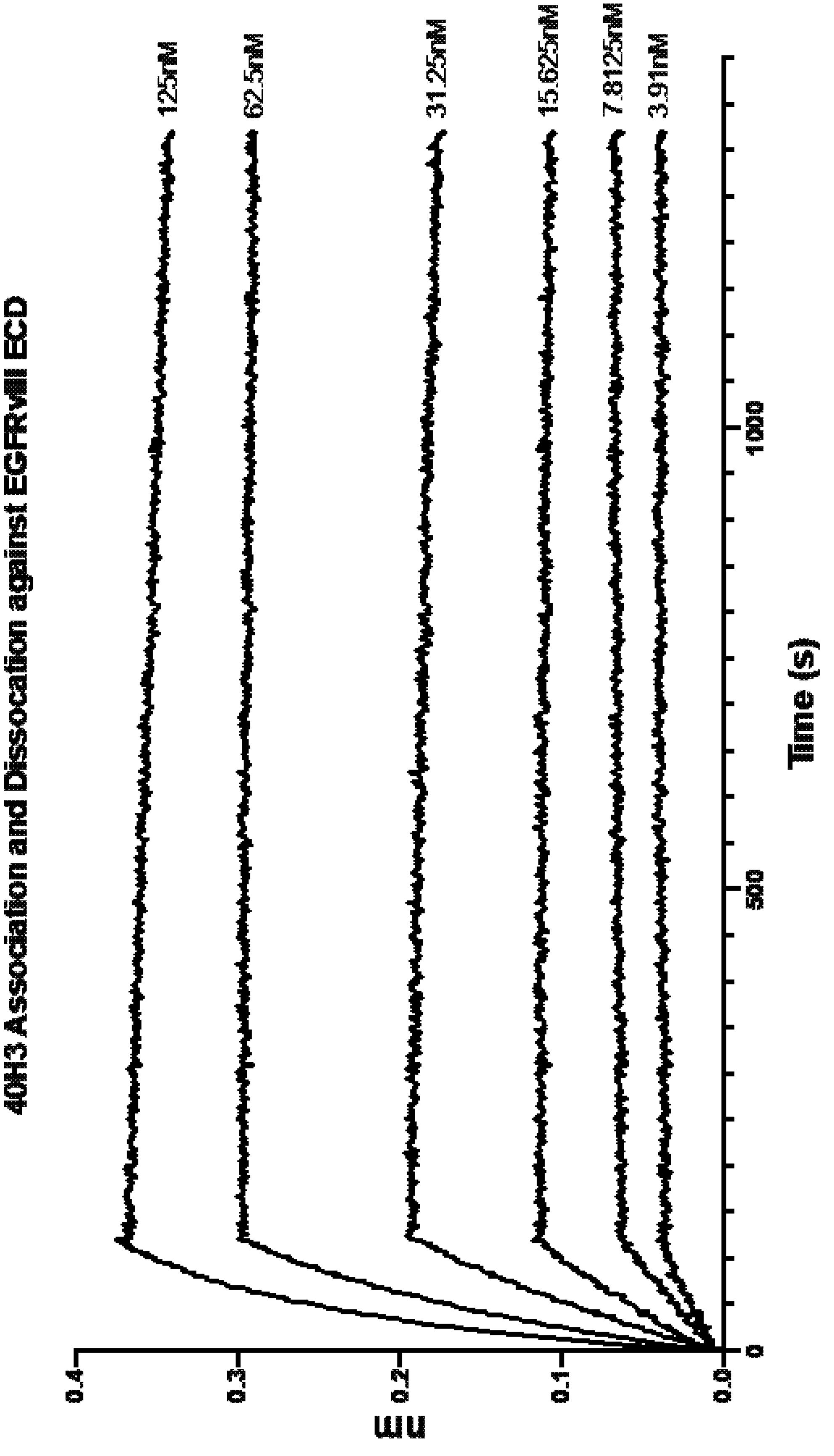

FIGS. 11A-11C. Binding data (using the Octet Biosensor) for 40H3 (full length antibody) against immobilized EGFR loop, EGFRvIII extracellular domain (ECD) or wtEGFR ECD.

Figure 12A:
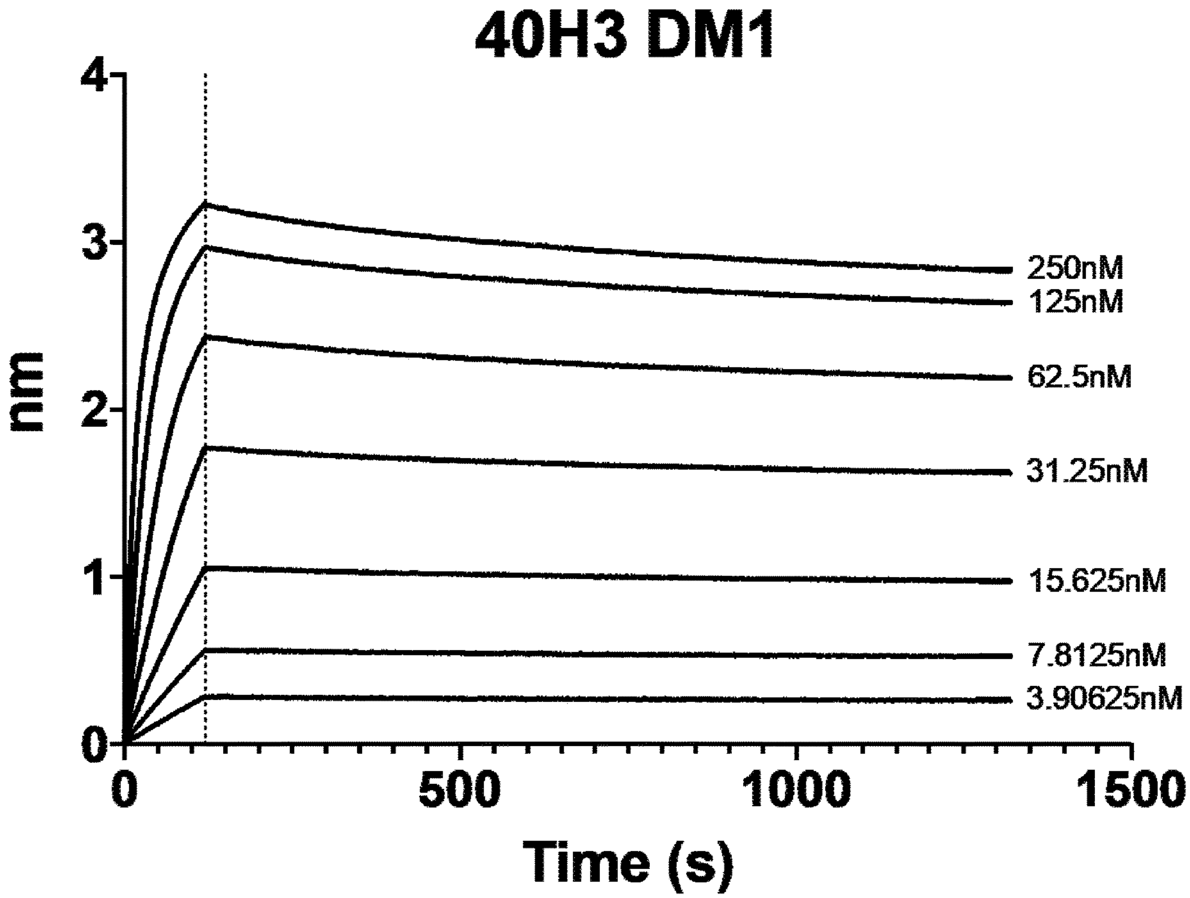
Figure 12B:
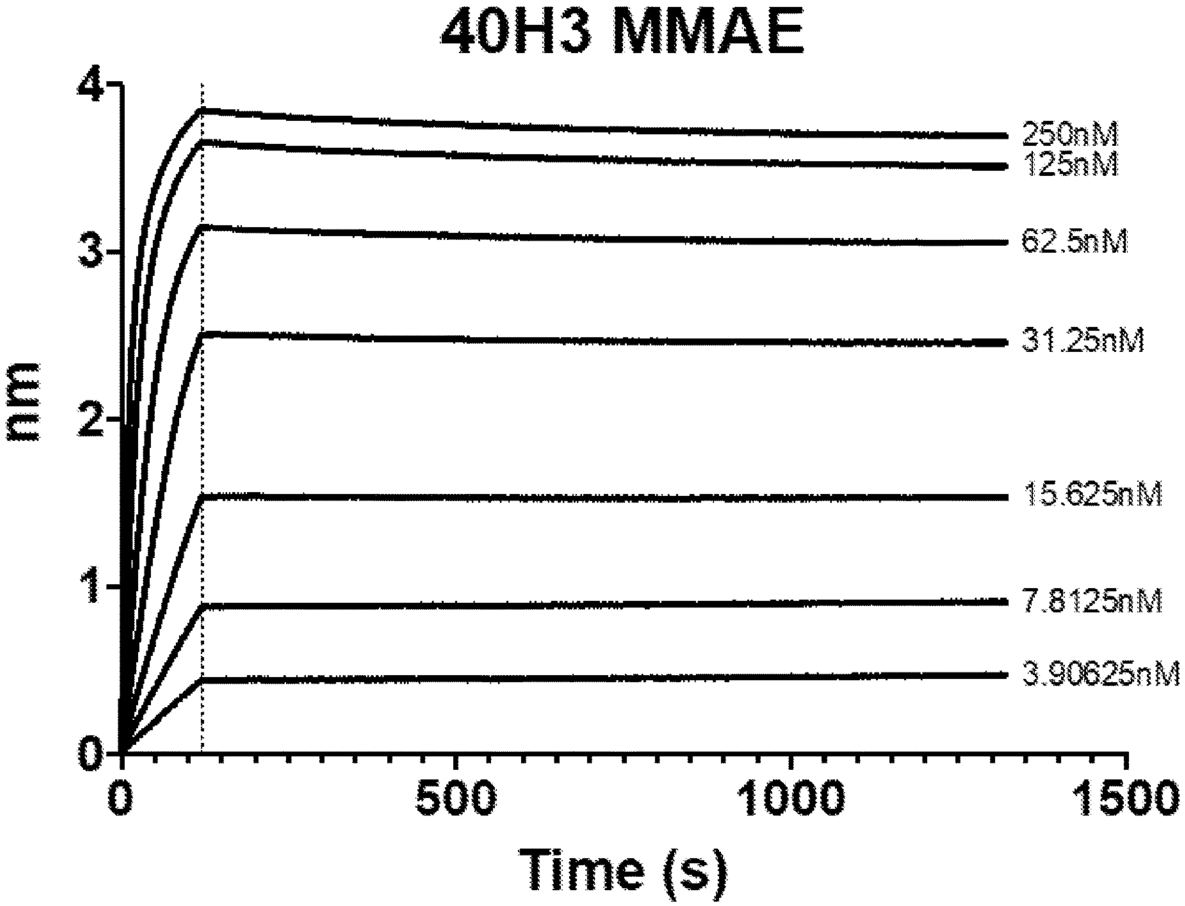
Figure 12C:
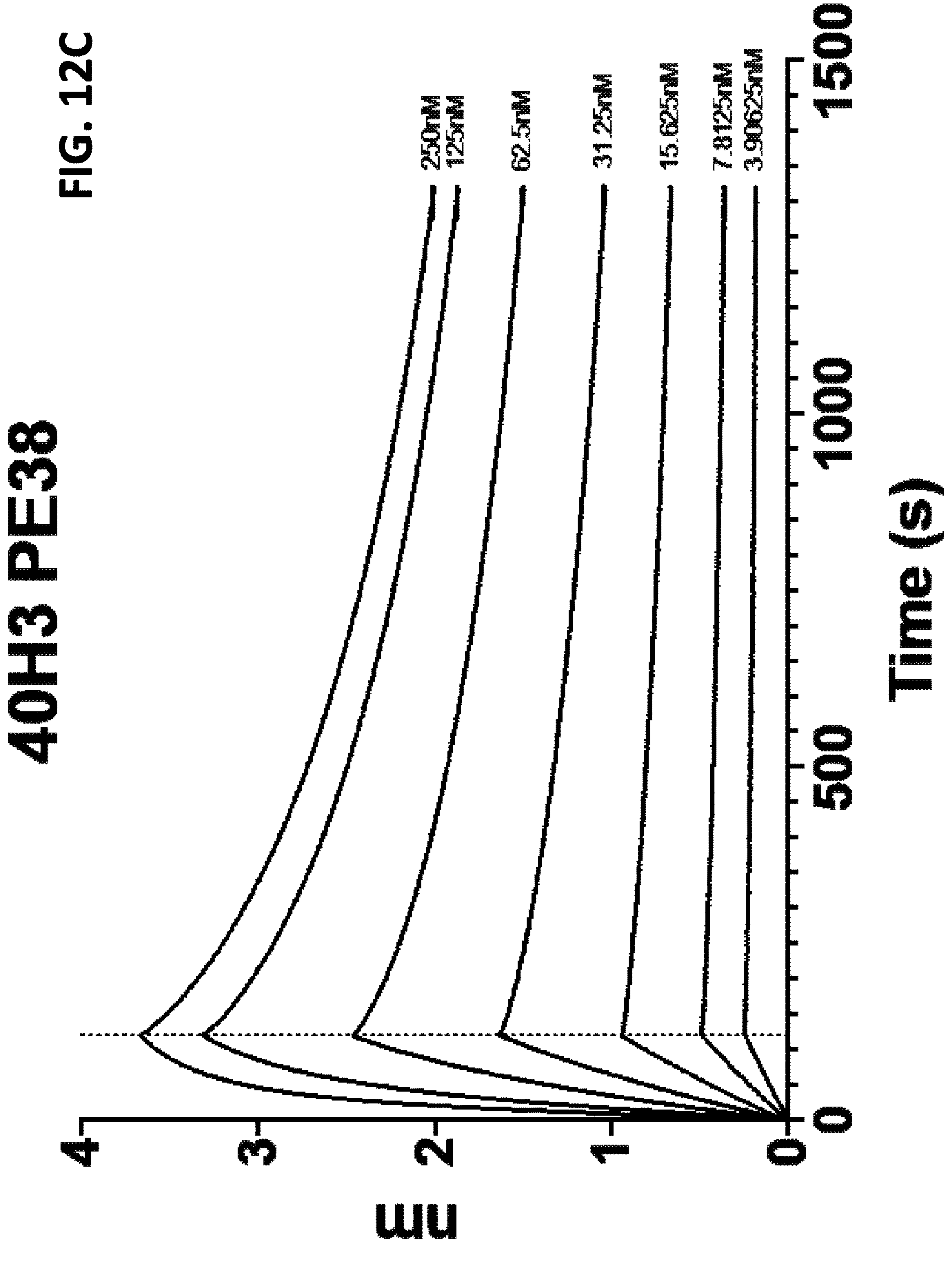

FIGS. 12A-12C. Octet Biosensor data for the interaction of 40H3-MMAE (antibody-drug conjugate ADC), 40H3-DM1 (ADC) or 40H3-PE38 immunotoxin against immobilized EGFR loop. The ADCs are constructed by the chemical attachment of cytotoxic drugs to full-length 40H3 antibody. The 40H3-PE38 immunotoxin is a single chain Fv (scFv) with a protein toxin fused to the scFv. Data confirms no loss of binding activity for either drug conjugate. Immunotoxin, which is monovalent, has a lower binding affinity, due to faster dissociation rate.

Figure 13A:
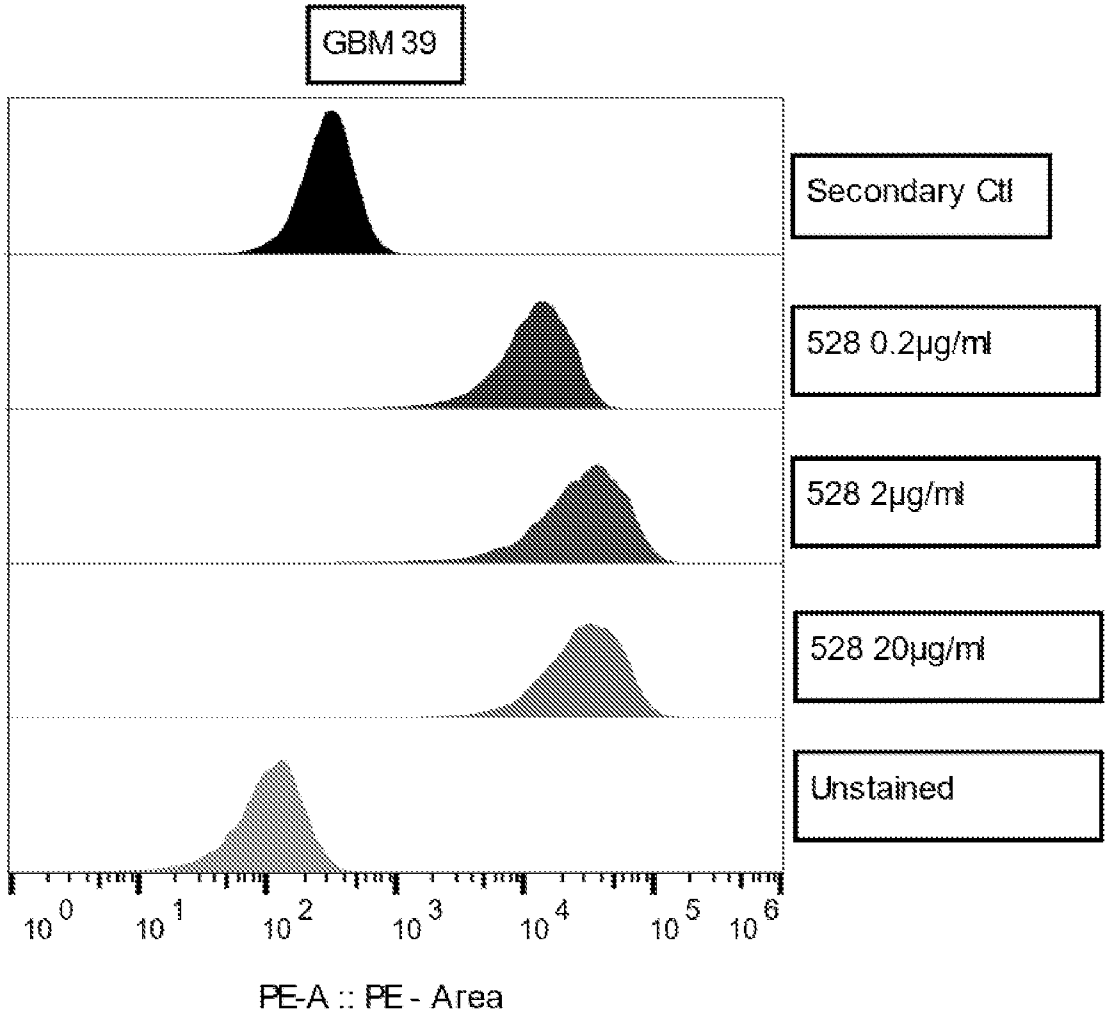
Figure 13B:
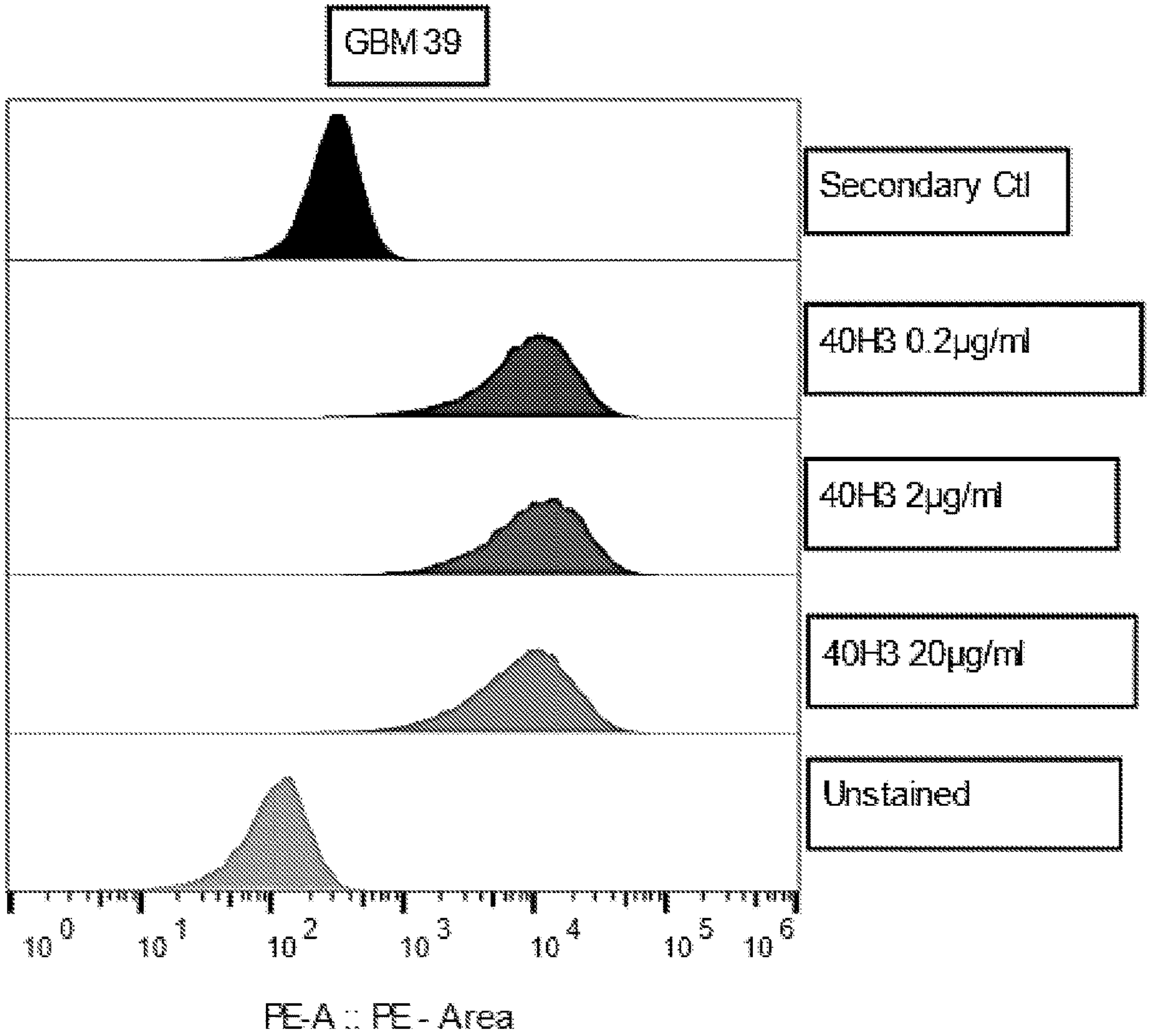
Figure 13C:
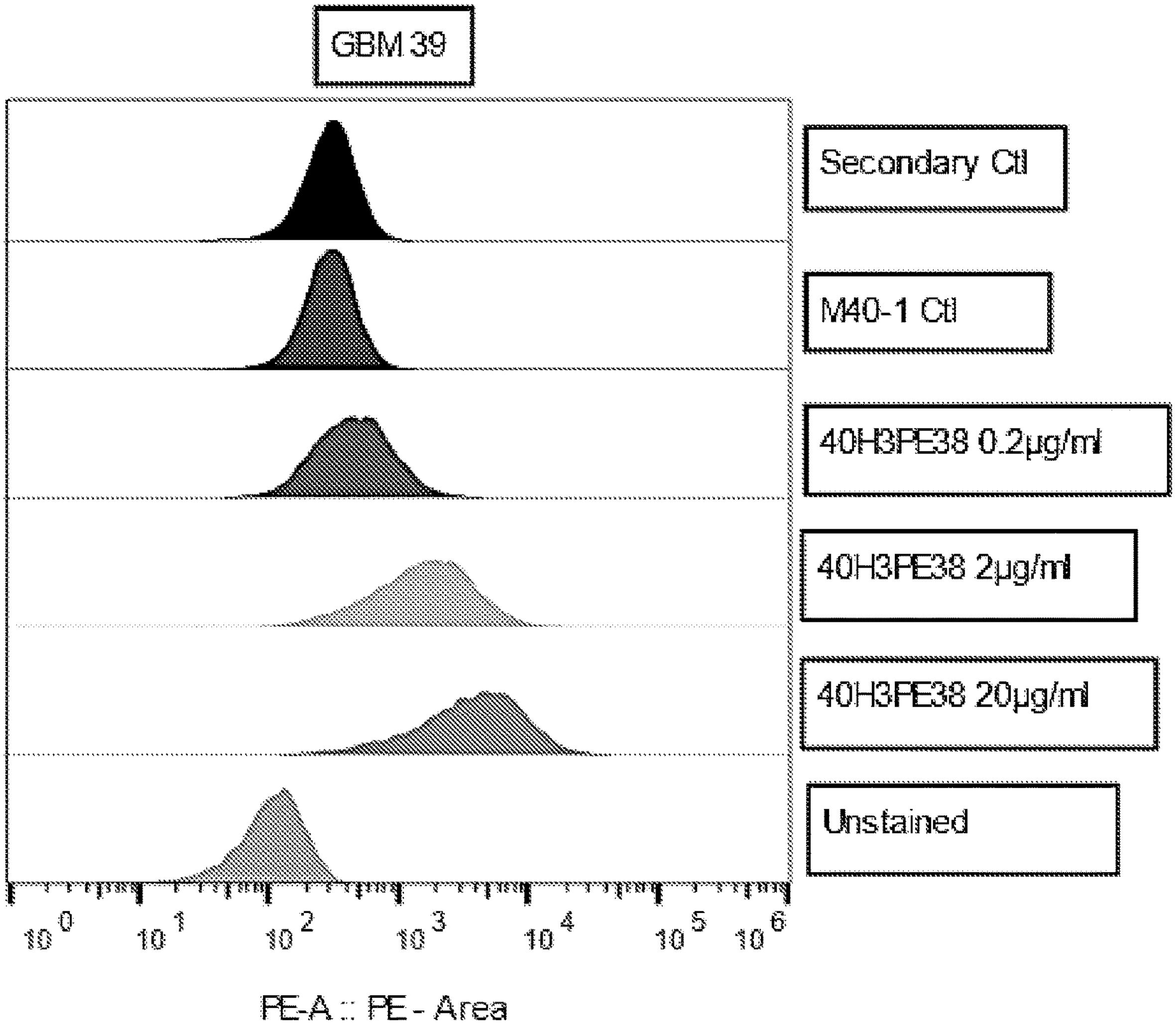

FIGS. 13A-13C. Flow cytometry data for 40H3 or 528 antibodies against PDX cell line, GBM39. 40H3 is the full-length antibody. The 528 antibody reacts with all species of EGFR. GBM39 is a PDX sample of a human glioblastoma.

Figure 14:
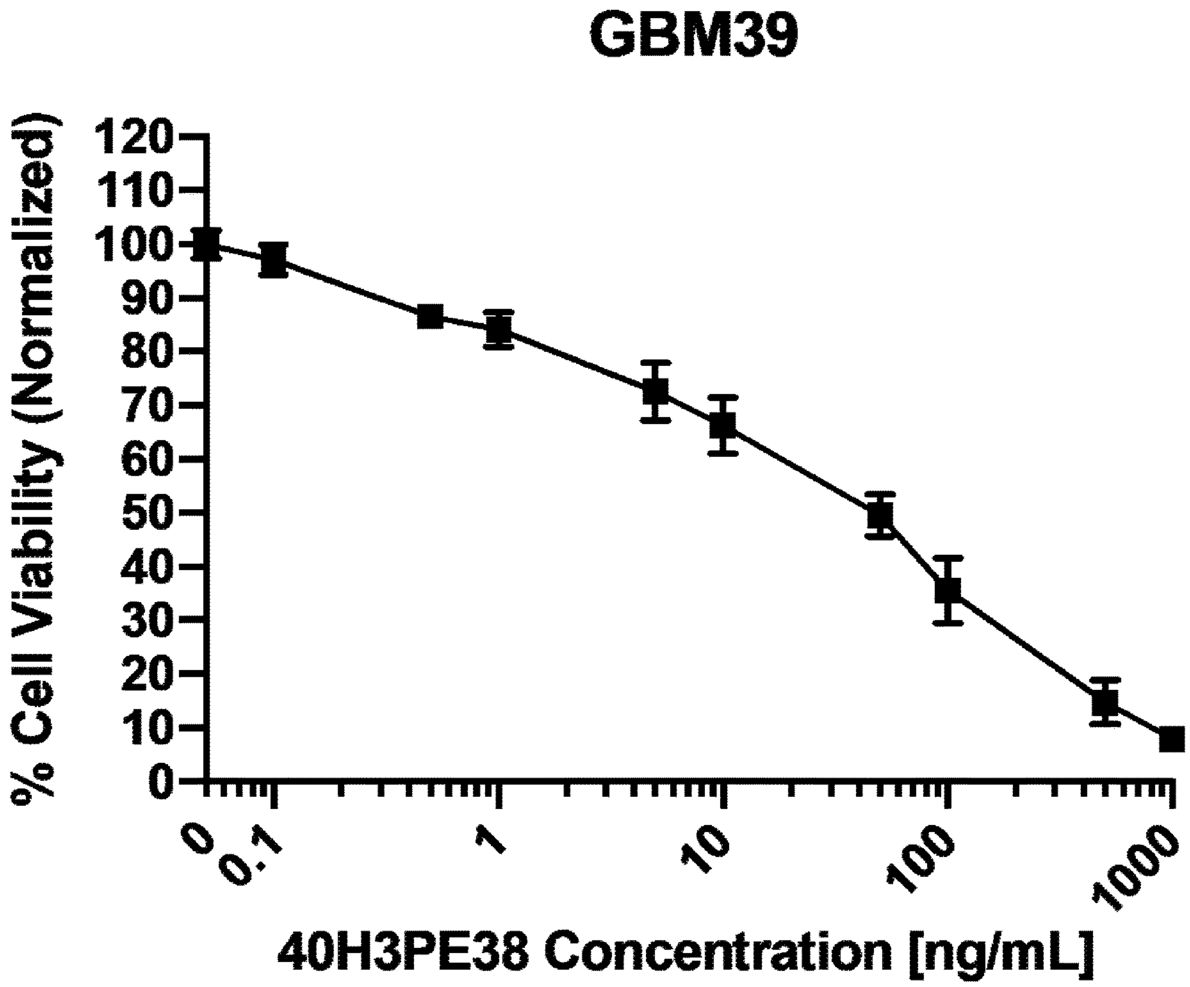

FIG. 14. Dose response curve of cell viability following the addition of 40H3-PE38 (immunotoxin) to GBM39 cells.

Figure 15A:
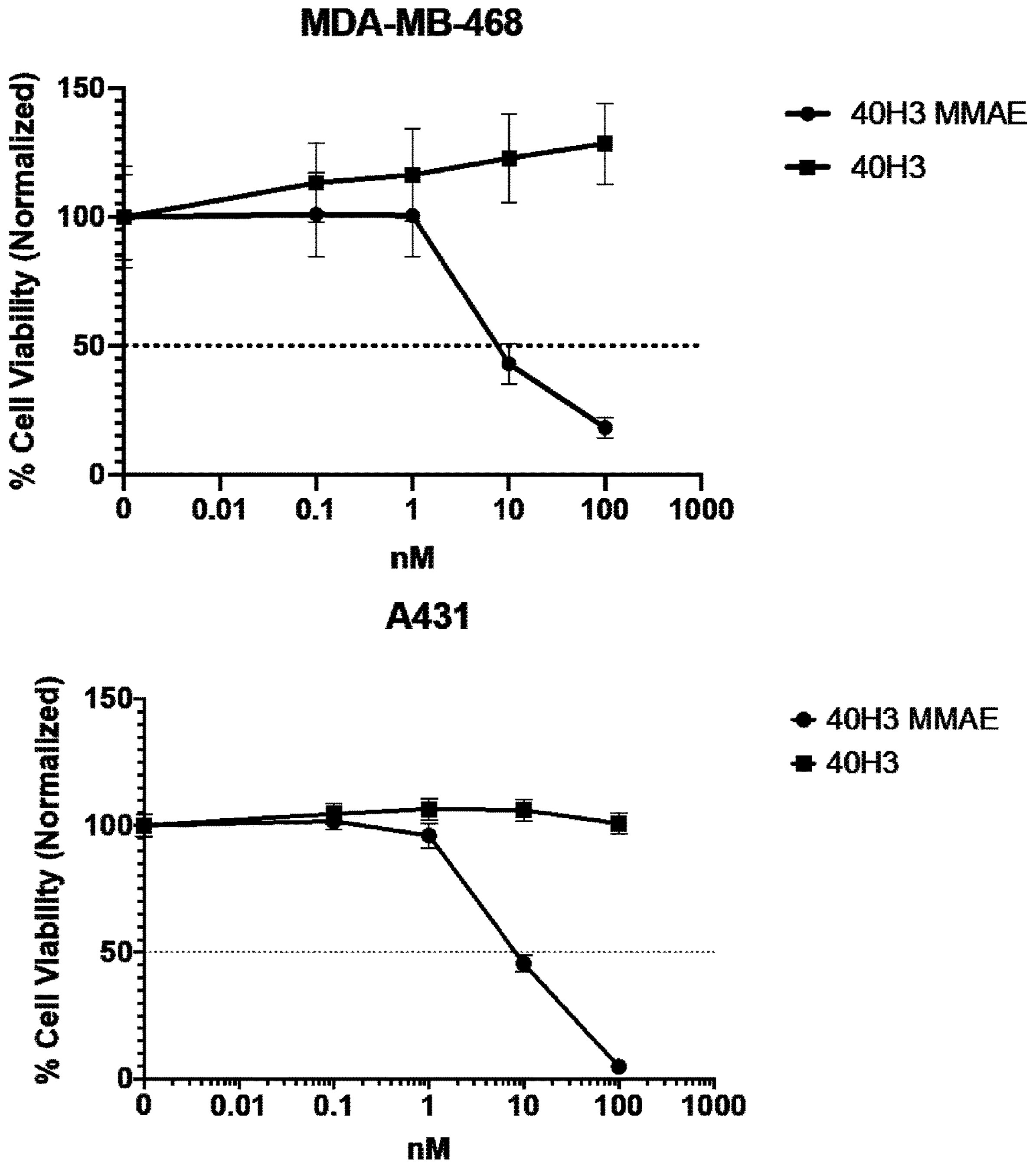
Figure 15B:
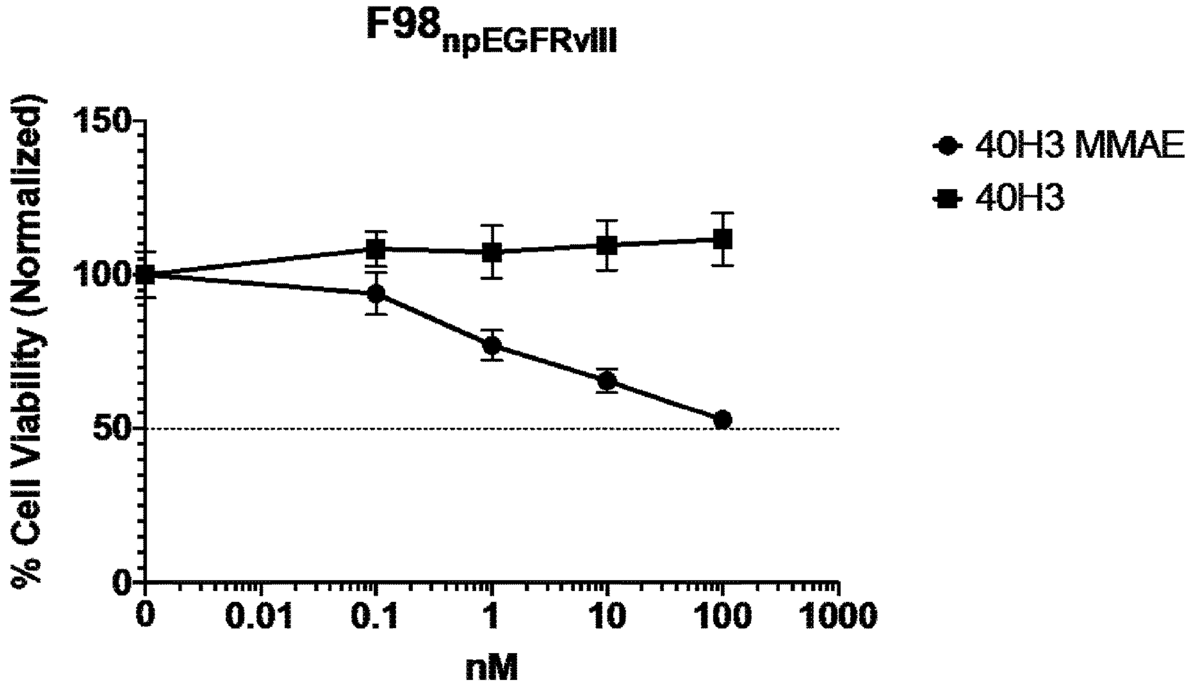

FIGS. 15A-15B. Dose response curves of cell viability following the addition 40H3-MMAE against MDA-MB-468, A431 or $F98_{npEGFRvIII}$ cells.

Figure 16A:
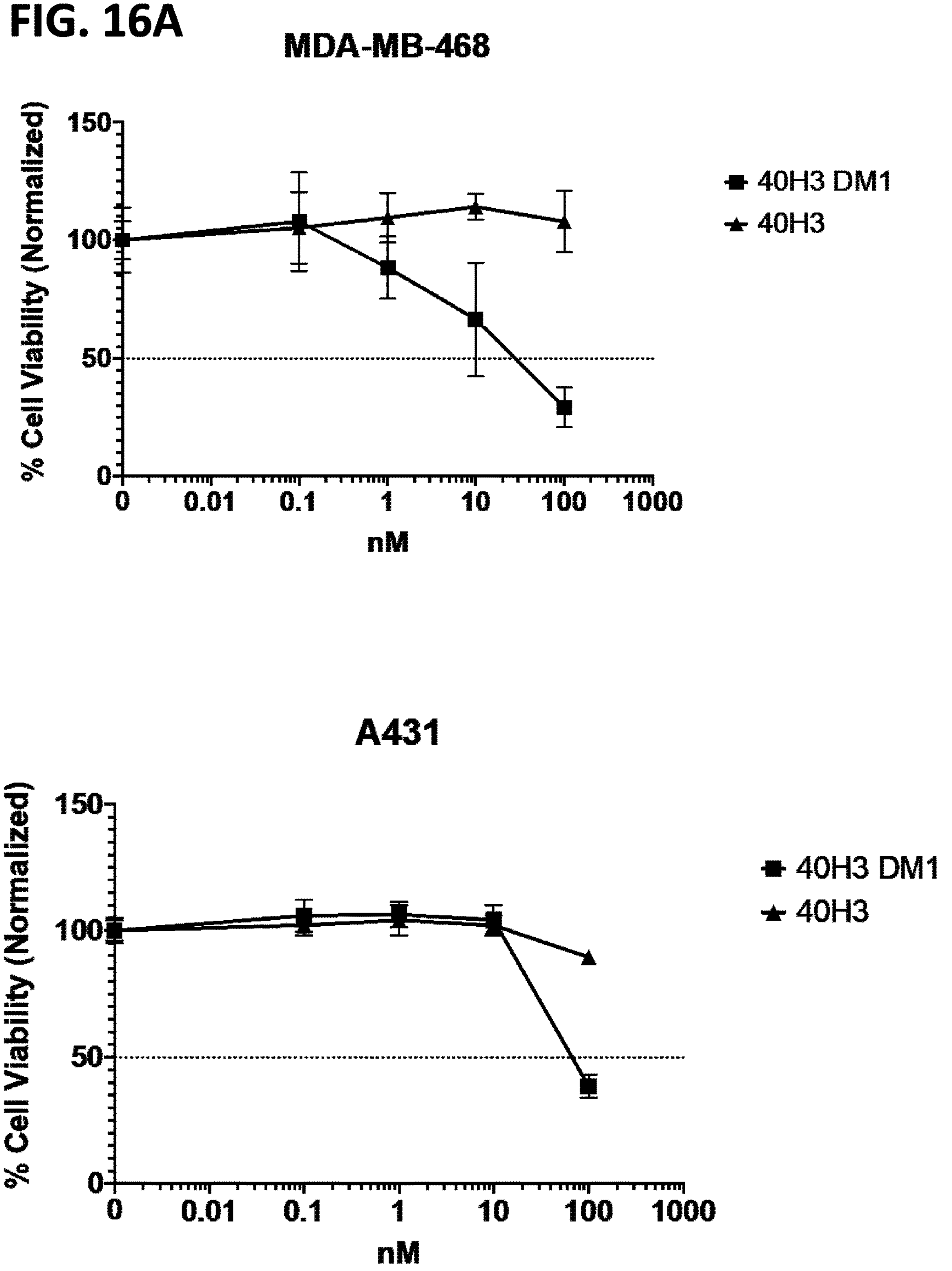
Figure 16B:
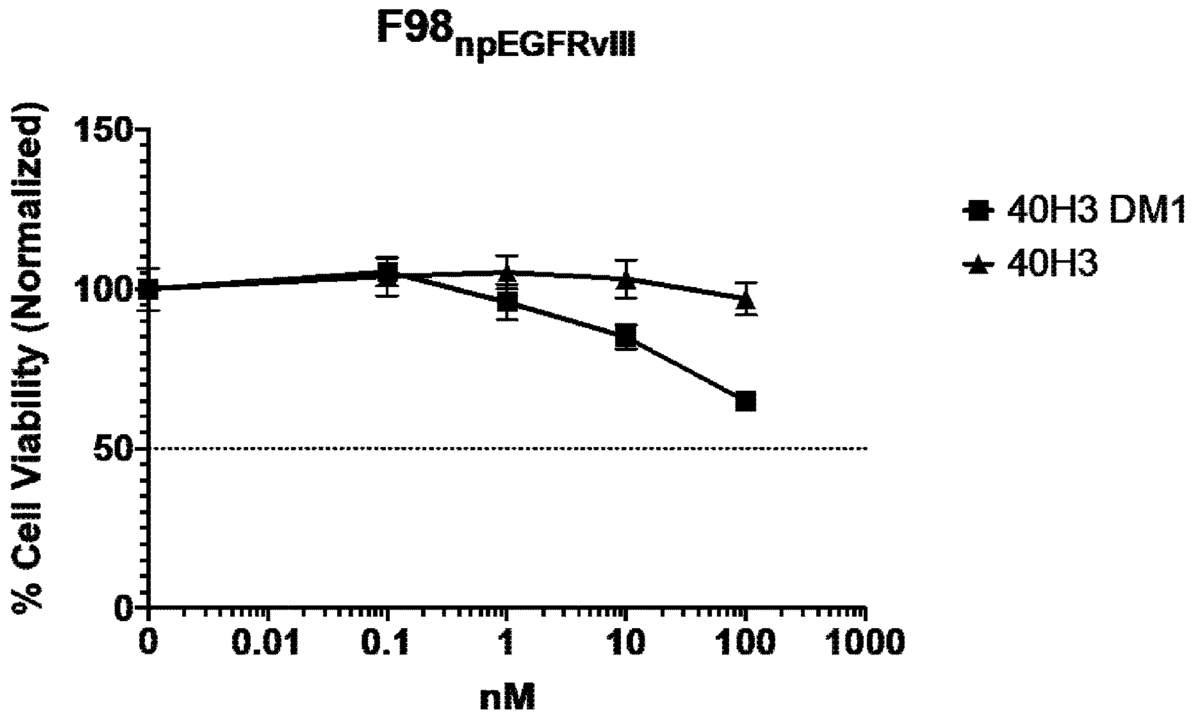

FIGS. 16A-16B. Dose response curves of cell viability following the addition 40H3-DM1 against MDA-MB-468, A431 or $F98_{npEGFRvIII}$ cells.

Figure 17:
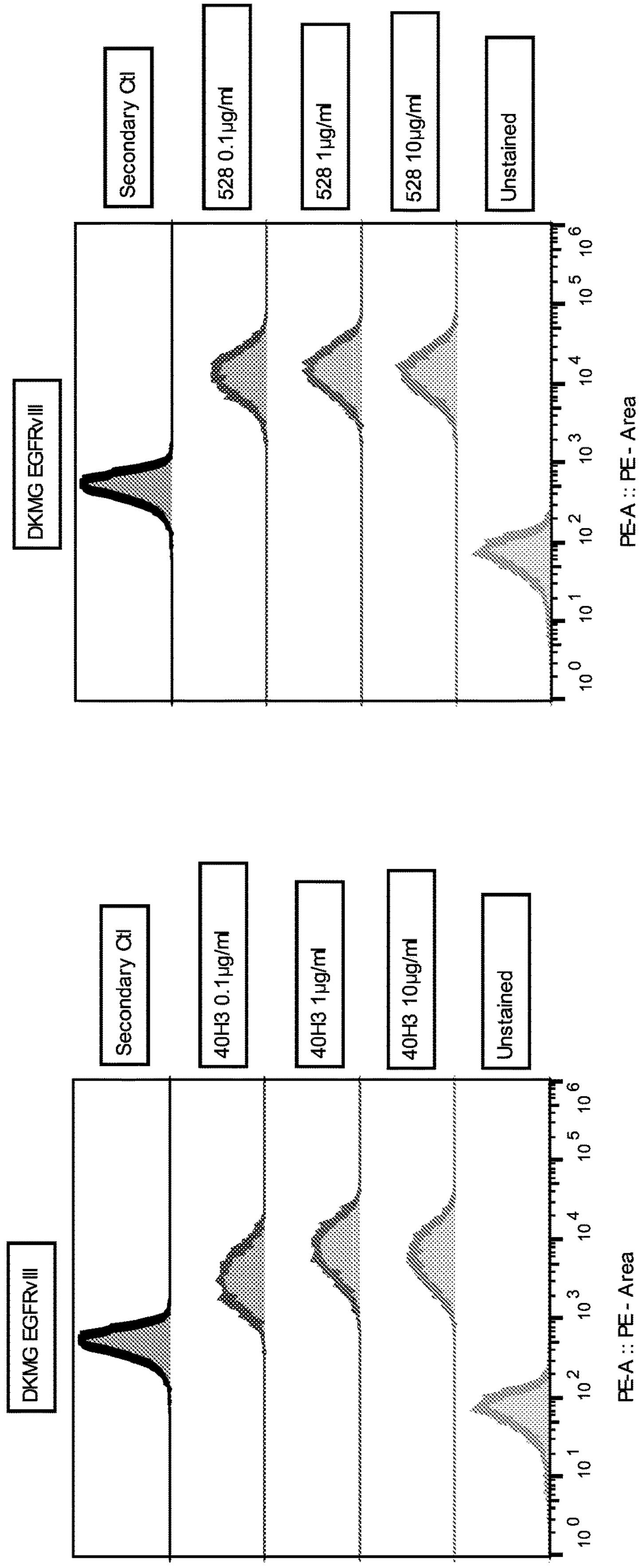

FIG. 17. Flow cytometry data for 40H3, 528 or 40H3-PE38 against DKMG EGFRvIII. The DKMG cell line is a permanent line established from cells derived from the glioblastoma. Cells were stably transduced with a viral vector coding for EGFRvIII that underwent genomic integration.

Figure 18:
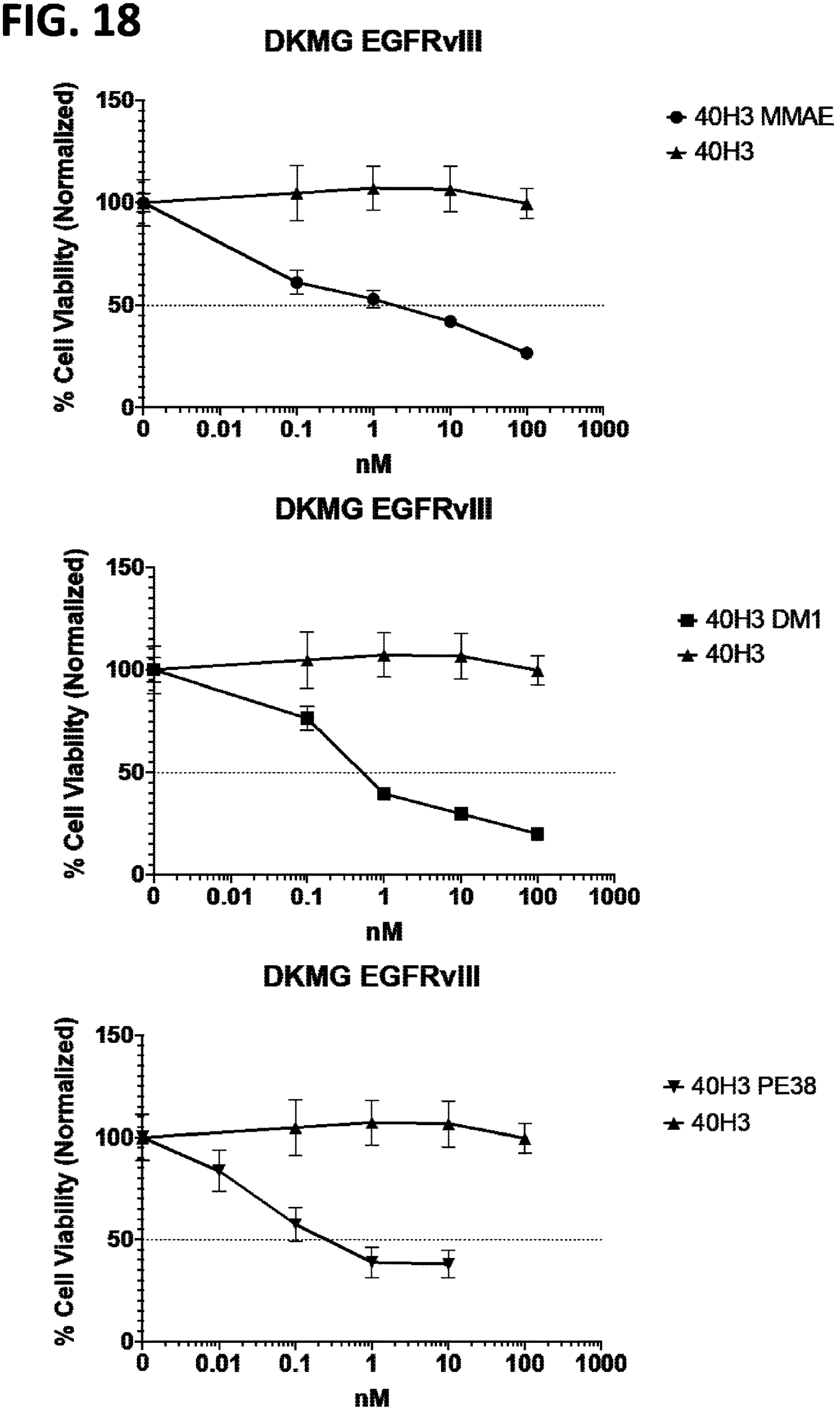

FIG. 18. Dose response curves of cell viability following the addition 40H3-MMAE, 40H3-DM1 or 40H3-PE38 against DKMG EGFRvIII.

Figure 19:
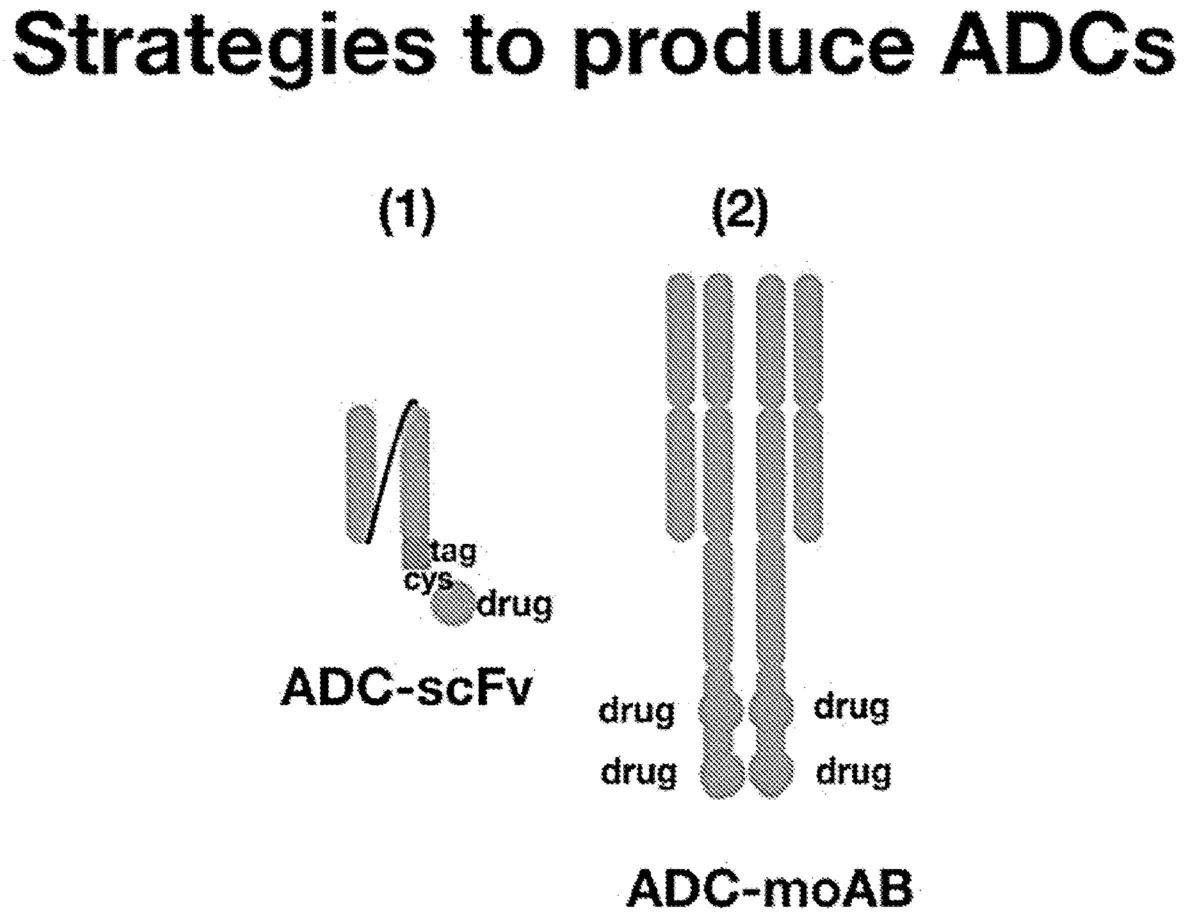

FIG. 19. scFv with a C-terminal cysteine for drug conjugation.

SEQUENCE LISTING

The nucleic and amino acid sequences listed are shown using standard letter abbreviations for nucleotide bases and amino acids, as defined in 37 C.F.R. 1.822. Only one strand of each nucleic acid sequence is shown, but the complementary strand is understood as included by any reference to the displayed strand. In the heavy and light chain variable domain sequences, the CDR sequences are underlined. The Sequence Listing is submitted as an ASCII text file [Sequence_Listing, Dec. 27, 2021, 41.0 KB], which is incorporated by reference herein. In the accompanying sequence listing:

SEQ ID NO: 1 is the amino acid sequence of the 40H3 heavy chain variable domain.
QVQLKQSGPGLVQPSQSLSITCTVSGFSLTNYGIHWLRQSPGKGLEWLGMMWRGGGTDYNAAFISRLTITKDTSKSQVFFRMNNLQTNDT

AIYYCARKGVGMGLGYWGQGTSVTVSS

SEQ ID NO: 2 is the amino acid sequence of the 40H3 light chain variable domain.
DIQMTQSPASQSASLGESVTITCLASQTIGTWVAWYQQKPGRSPQLLIYGATNLADGVPSRFSGSGSGTKFSFKISSLQAEDFVSYYCQQ

LYSNPYTFGGGTKLEIK

SEQ ID NO: 3 is an exemplary nucleic acid sequence encoding the 40H3 heavy chain variable domain.
CAGGTGCAGCTGAAGCAGTCAGGACCTGGCCTAGTGCAGCCCTCACAGAGCCTGTCCATCACCTGCACAGTCTCTGGCTTCTCATTGACT AACTATGGTATTCACTGGCTTCGCCAGTCTCCAGGAAAGGGTCTGGAGTGGCTGGGAATGATGTGGCGTGGTGGAGGCACAGACTATAAT GCAGCTTTCATCTCCAGACTGACTATCACCAAGGACACTTCCAAGAGCCAAGTTTTCTTTAGAATGAACAATCTGCAAACTAATGACACA GCCATATATTACTGTGCCAGAAAAGGGGTGGGAATGGGTTTGGGTTATTGGGGCCAAGGAACCTCAGTCACCGTCTCCTCA SEQ ID NO: 4 is an exemplary nucleic acid sequence encoding the 40H3 light chain variable domain.
GACATTCAGATGACCCAGTCTCCTGCCTCCCAGTCTGCATCTCTGGGAGAAAGTGTCACCATCACATGCCTGGCAAGTCAGACCATTGGT ACATGGGTAGCATGGTATCAACAGAAACCAGGGAGATCTCCTCAGCTCCTGATCTATGGTGCAACCAACTTGGCAGATGGGGTCCCATCA AGATTCAGTGGTAGTGGATCTGGCACAAAATTTTCTTTCAAGATCAGCAGCCTACAGGCTGAAGATTTTGTAAGCTATTACTGTCAACAA

CTTTACAGTAATCCGTACACGTTCGGAGGGGGGACCAAACTGGAAATAAAG

-continued

SEQ ID NOs: 5-10 are the amino acid sequences of 40H3 CDRs.

40H3-H-CDR1 (SEQ ID NO: 5)

GFSLTNYG

40H3-H-CDR2 (SEQ ID NO: 6)

MWRGGGT

40H3-H-CDR3 (SEQ ID NO: 7)

ARKGVGMGLGY

40H3-L-CDR1 (SEQ ID NO: 8)

QTIGTW

40H3-L-CDR2 (SEQ ID NO: 9)

GAT

40H3-L-CDR3 (SEQ ID NO: 10)

QQLYSNPYT

SEQ ID NO: 11 is the amino acid sequence of a consensus heavy chain variable domain for 3D10/9G11.

QVQLKQSGPGLVQPSQSLSI$X_1$CTVSGFSLTRNGVHWVRQSPGKGLEWVGVIWR$X_2$GRTDYDAAFMSRLSITKDNSKSQVFFKMNSLQADD

TAIYYCVKNGDDGNYGTYWGQGTLVTVSA $X_1$ is I or T $X_2$ is S or G.

SEQ ID NO: 12 is the amino acid sequence of a light chain variable domain for 3D10 and 9G11.

DIVMSQSPSSLGVSVGEKVTMSCKSSQSLLDSRNQKNYLAWYQQKPGQSPKLLIYWASTRESGVPDRFTGSGSGTEFTLTISSVKAEDLA
IYYCQQYYNYPYTFGGGTKLEIT

SEQ ID NO: 13 is the amino acid sequence of a consensus heavy chain variable domain for 1D9/4A4

QVQLKQSGRSLVQPSQSLSITCTVSGFSLTDYGVHWIRQSPGKGLEWLGVIWRSGRTDYNAVFMSRLSITKDNSKSQVFFKMNGL$X_1X_2X_3$

DTAIYYCAKNGPFGNFAGYWGQGTPVAVSA $X_1$ = Q or L $X_2$ = T or I $X_3$ = D or E

SEQ ID NO: 14 is the amino acid sequence of a consensus light chain variable domain for 1D9/4A4

(SEQ ID NO: 14)

DIVMSQSPSSLAVSVGEKVTMRCRSSQSLLDSYHQKNYLAWYLQKPGQSPKLLIYWASTRESGVPDRFTGSGSGTDFTLTISSVKAEDLA

XYYCQEYYRYPYTFGGGTKLEIK

Wherein X is V or A

SEQ ID NO: 15 is the amino acid sequence of a consensus heavy chain variable domain for 11E11/11G3

(SEQ ID NO: 15)

QVQLKQSGPSLVQPSQSLSITCTVSGFSLTNYGVHW$X_1$RQSPGKGLEWLGV$X_2$WRGGRTDYNAAFMSRLSIT$X_3$DNSRSQVFFKMNSLQTD

D$X_4$AIYYCAKNGPFGNFAGYWGQGTLVTVS$X_5$ $X_1$ = I or V $X_2$ = K or M $X_3$ = R or K $X_4$ = T or A $X_5$ = A or T

-continued

SEQ ID NO: 16 is the amino acid sequence of a consensus light chain variable domain for 11E11/11G3
DIVMSQSPSSL$X_1$VSVGEKVSLTCKSSX$_2$SLLDNQKHYLAWYQQKPGQSPKLLIYWASTRESGVPDRFTGSGSGTEFTLTISSVKAEDLAV

YYCQQFYNYPYTFGGGTKLEIK $X_1$ = A or P $X_2$ = Q or R

SEQ ID NO: 17 is the amino acid sequence of the 3D10 heavy chain variable domain.
QVQLKQSGPGLVQPSQSLSIICTVSGFSLTRNGVHWVRQSPGKGLEWVGVIWRSGRTDYDAAFMSRLSITKDNSKSQVFFKMNSLQADDT

AIYYCVKNGDDGNYGTYWGQGTLVTVSA

SEQ ID NO: 18 is an exemplary nucleic acid encoding a 3D10 heavy chain variable domain.
CAGGTGCAGCTGAAGCAGTCAGGACCTGGCCTAGTGCAGCCCTCACAGAGCCTGTCCATAATCTGCACAGTCTCGGGTTTCTCATTAACT CGCAACGGTGTACATTGGGTTCGTCAGTCCCCAGGAAAGGGTCTGGAGTGGGTGGGAGTGATATGGAGAAGTGGAAGGACAGACTACGAT GCAGCTTTCATGTCCAGACTGAGCATCACCAAGGACAACTCCAAGAGCCAAGTTTTCTTTAAAATGAACAGTCTGCAGGCTGATGACACT GCCATTTACTACTGTGTCAAAAATGGGGACGATGGTAACTACGGGACTTACTGGGGCCAAGGGACTCTGGTCACTGTCTCTGCA SEQ ID NO: 19 is an exemplary nucleic acid encoding the 3D10 and 9G11 light chain variable domain.
GACATTGTGATGTCACAGTCTCCATCCTCCCTAGGTGTGTCAGTTGGAGAGAAGGTGACTATGAGCTGCAAGTCCAGTCAGAGCCTTTTA GATAGTAGGAATCAAAAGAACTACTTGGCCTGGTACCAGCAGAAACCAGGGCAGTCTCCTAAACTGCTGATTTACTGGGCATCCACTAGG GAATCTGGGGTCCCTGATCGCTTCACAGGCAGTGGATCTGGGACAGAATTCACTCTCACCATCAGCAGTGTGAAGGCTGAAGACCTGGCA

ATTTATTACTGTCAACAATATTATAACTATCCGTACACGTTCGGAGGGGGGACCAAGCTGGAAATAACA.

Due to the degeneracy of the genetic code, postion 97 can be a C or an A, and position 291 can be a C or a T.

SEQ ID NOs: 20-25 are the amino acid sequences of 3D10 CDRs.

3D10-H-CDR1
(SEQ ID NO: 20

GFSLTRNG

3D10-H-CDR2
(SEQ ID NO: 21)

IWRSGRT

3D10-H-CDR3
(SEQ ID NO: 22)

VKNGDDGNYGTY

3D10-L-CDR1
(SEQ ID NO: 23)

QSLLDSRNQKNY

3D10-L-CDR2
(SEQ ID NO: 24)

WAS

3D10-L-CDR3
(SEQ ID NO: 25)

QQYYNYPYT

SEQ ID NO: 26 is the amino acid sequence of the 9G11 heavy chain variable domain.
QVQLKQSGPGLVQPSQSLSITCTVSGFSLTRNGVHWVRQSPGKGLEWVGVIWRGGRTDYDAAFMSRLSITKDNSKSQVFFKMNSLQADDT

AIYYCVKNGDDGNYGTYWGQGTLVTVSA

SEQ ID NO: 27 is an exemplary nucleic acid sequence encoding the 9G11 heavy chain variable domain.
CAGGTGCAGCTGAAGCAGTCAGGACCTGGCCTAGTGCAGCCCTCACAGAGCCTGTCCATAACCTGCACAGTCTCGGGTTTCTCATTAACT CGCAATGGTGTCCATTGGGTTCGTCAGTCCCCAGGAAAGGGTCTGGAGTGGGTGGGAGTGATATGGAGAGGTGGAAGGACAGACTACGAT GCAGCTTTCATGTCCAGACTGAGCATCACCAAGGACAACTCCAAGAGCCAAGTTTTCTTTAAAATGAACAGTCTGCAGGCTGATGACACT GCCATTTACTACTGTGTCAAAAATGGGGACGATGGTAATTACGGGACTTACTGGGGCCAAGGGACTCTGGTCACTGTCTCTGCA -continued SEQ ID NOs: 20, 28, 22, 23, 24 and 25 are the amino acid sequences of 9G11 CDRs. Five of the CDRs are the same as the CDRs of 3D10.

9G11-H-CDR1

(SEQ ID NO: 20)

GFSLTRNG

9G11-H-CDR2

(SEQ ID NO: 28)

IWRGGRT

9G11-H-CDR3

(SEQ ID NO: 22)

VKNGDDGNYGTY

9G11-L-CDR1

(SEQ ID NO: 23)

QSLLDSRNQKNY

9G11-L-CDR2

(SEQ ID NO: 24)

WAS

9G11-L-CDR3

(SEQ ID NO: 25)

QQYYNYPYT

SEQ ID NO: 29 is the amino acid sequence of the 1D9 heavy chain variable domain.

QVQLKQSGRSLVQPSQSLSITCTVSGFSLTDYGVHWIRQSPGKGLEWLGVIWRSGRTDYNAVFMSRLSITKDNSKSQVFFKMNGLQTDDT

AIYYCAKNGPFGNFAGYWGQGTPVAVSA

SEQ ID NO: 30 is the amino acid sequence of the 1D9 light chain variable domain.

DIVMSQSPSSLAVSVGEKVTMRCRSSQSLLDSYHQKNYLAWYLQKPGQSPKLLIYWASTRESGVPDRFTGSGSGTDFTLTISSVKAEDLA

VYYCQEYYRYPYTFGGGTKLEIK

SEQ ID NO: 31 is an exemplary nucleic acid sequence encoding a 1D9-1 heavy chain variable domain.

CAGGTGCAGCTGAAGCAGTCAGGACGTAGCCTAGTGCAGCCCTCACAGAGCCTGTCCATCACCTGCACAGTCTCTGGTTTCTCATTAACT

GACTATGGTGTACACTGGATTCGTCAGTCTCCAGGAAAGGGTCTGGAGTGGCTGGGAGTGATATGGAGAAGTGGAAGAACAGACTACAAT

GCAGTTTTCATGTCCAGACTGAGCATCACCAAGGACAACTCCAAGAGCCAAGTTTTCTTTAAAATGAACGGTCTGCAAACTGATGACACT

GCCATATACTACTGTGCCAAAAATGGCCCCTTTGGTAACTTCGCTGGTTACTGGGGCCAAGGAACTCCGGTCGCTGTCTCTGCA

SEQ ID NO: 32 is an exemplary nucleic acid sequence encoding the 1D9 light chain variable domain.

GACATTGTGATGTCCCAGTCTCCATCCTCCCTAGCTGTGTCAGTTGGAGAGAAGGTAACTATGCGCTGCAGGTCCAGTCAGAGCCTTTTA

GATAGTTACCATCAAAAAAACTACTTGGCCTGGTACCTGCAGAAACCAGGGCAGTCTCCTAAACTGCTGATTTACTGGGCATCCACTAGG

GAATCTGGGGTCCCTGATCGCTTCACAGGCAGTGGATCTGGGACAGATTTCACTCTCACCATCAGCAGTGTGAAGGCTGAAGACCTGGCA

GTTTATTACTGTCAGGAATATTATAGGTATCCGTACACGTTCGGAGGGGGGACCAAACTGGAAATAAAA

SEQ ID NOs: 33-38 are the amino acid sequences of the CDRs of 1D9.

1D9-H-CDR1

(SEQ ID NO: 33)

GFSLTDYG

1D9-H-CDR2

(SEQ ID NO: 34)

IWRSGRT

1D9-H-CDR3

(SEQ ID NO: 35)

AKNGPFGNFAGY

1D9-L-CDR1

(SEQ ID NO: 36)

QSLLDSYHQKNY

1D9-L-CDR2

(SEQ ID NO: 37)

WAS

1D9-L-CDR3

(SEQ ID NO: 38)

QEYYRYPYT

-continued

SEQ ID NO: 39 is the amino acid sequence of the 4A4 heavy chain variable domain.
QVQLKQSGRSLVQPSQSLSITCTVSGFSLTDYGVHWIRQSPGKGLEWLGVIWRSGRTDYNAVFMSRLSITKDNSKSQVFFKMNGLLIEDTAIYYCAKNGPFGNFAGYWGQGTPVAVSA SEQ ID NO: 40 is the amino acid sequence of the 4A4 light chain variable domain.
DIVMSQSPSSLAVSVGEKVTMRCRSSQSLLDSYHQKNYLAWYLQKPGQSPKLLIYWASTRESGVPDRFTGSGSGTDFTLTISSVKAEDLAAYYCQEYYRYPYTFGGGTKLEIK SEQ ID NO: 41 is an exemplary nucleic acid sequence encoding the 4A4 heavy chain variable domain.
CAGGTGCAGCTGAAGCAGTCAGGACGTAGCCTAGTGCAGCCCTCACAGAGCCTGTCCATCACCTGCACAGTCTCTGGTTTCTCATTAACTGACTATGGTGTACACTGGATTCGTCAGTCTCCAGGAAAGGGTCTGGAGTGGCTGGGAGTGATATGGAGAAGTGGAAGAACAGACTACAATGCAGTTTTCATGTCCAGACTGAGCATCACCAAGGACAACTCCAAGAGCCAAGTTTTCTTTAAAATGAACGGTCTGCTAATTGAAGACACTGCCATATACTACTGTGCCAAAAATGGCCCCTTTGGTAATTTCGCTGGTTACTGGGGCCAAGGAACTCCGGTCGCTGTCTCTGCA SEQ ID NO: 42 is an exemplary nucleic acid sequence encoding the 4A4 light chain variable domain.
GACATTGTGATGTCCCAGTCTCCATCCTCCCTAGCTGTGTCAGTTGGAGAGAAGGTAACTATGCGCTGCAGGTCCAGTCAGAGCCTTTTAGATAGTTACCATCAAAAGAACTACTTGGCCTGGTACCTGCAGAAACCAGGGCAGTCTCCTAAACTGCTGATTTACTGGGCATCCACTAGGGAATCTGGGGTCCCTGATCGCTTCACAGGCAGTGGATCTGGGACAGATTTCACTCTCACCATCAGCAGTGTGAAGGCTGAAGACCTGGCAGCTTATTACTGTCAGGAATATTATAGGTATCCGTACACGTTCGGAGGGGGGACCAAACTGGAAATAAAA SEQ ID NOs: 33-35 and 36-38 are the amino acid sequences of the CDRs for 4A4. Note that these are the same as the amino acid sequences of the CDRs of 1D9.

4A4-H-CDR1
(SEQ ID NO: 33)
GFSLTDYG

4A4-H-CDR2
(SEQ ID NO: 34)
IWRSGRT

4A4-H-CDR3
(SEQ ID NO: 35)
AKNGPFGNFAGY

4A4-L-CDR1
(SEQ ID NO: 36)
QSLLDSYHQKNY

4A4-L-CDR2
(SEQ ID NO: 37)
WAS

4A4-L-CDR3
(SEQ ID NO: 38)
QEYYRYPYT

SEQ ID NO: 43 is the amino acid sequence of the 11E11 heavy chain variable domain.
QVQLKQSGPSLVQPSQSLSITCTVSGFSLTNYGVHWIRQSPGKGLEWLGVKWRGGRTDYNAAFMSRLSITRDNSRSQVFFKMNSLQTDDTAIYYCAKNGPFGNFAGYWGQGTLVTVSA SEQ ID NO: 44 is the amino acid sequence of the 11E11 light chain variable domain.
DIVMSQSPSSLAVSVGEKVSLTCKSSQSLLDNQKHYLAWYQQKPGQSPKLLIYWASTRESGVPDRFTGSGSGTEFTLTISSVKAEDLAVYYCQQFYNYPYTFGGGTKLEIK SEQ ID NO: 45 is an exemplary nucleic acid encoding the 11E11 heavy chain variable domain.
CAGGTGCAGCTGAAGCAGTCAGGACCTAGCCTAGTGCAGCCCTCACAGAGCCTGTCCATAACCTGCACAGTCTCTGGTTTCTCATTAACTAACTATGGTGTACACTGGATTCGCCAGTCTCCAGGAAAGGGTCTGGAGTGGCTGGGAGTGAAGTGGAGAGGTGGACGCACAGACTACAATGCAGCTTTCATGTCCAGACTGAGCATCACCAGGGACAACTCCAGGAGCCAAGTTTTCTTTAAAATGAACAGTCTCCAAACTGATGACACTGCCATATACTACTGTGCCAAAAATGGCCCCTTTGGTAACTTCGCTGGTTATTGGGGCCAAGGGACTCTGGTCACTGTCTCTGCA -continued SEQ ID NO: 46 is an exemplary nucleic acid encoding the 11E11 light chain variable domain.

GACATTGTGATGTCACAGTCTCCATCCTCCCTAGCTGTGTCAGTTGGAGAGAAGGTTAGTCTGACCTGCAAGTCCAGTCAGAGCCTTTTA

GACAATCAAAAGCACTACTTGGCCTGGTACCAGCAGAAACCAGGGCAGTCTCCTAAACTGCTGATTTACTGGGCATCCACTAGGGAATCT

GGGGTCCCTGATCGCTTCACAGGCAGTGGATCTGGGACAGAATTCACTCTCACTATCAGCAGTGTGAAGGCTGAAGACCTGGCAGTTTAT

TACTGTCAGCAATTTTATAACTATCCGTACACGTTCGGAGGGGGGACCAAGCTGGAAATAAAA

SEQ ID NOs: 47-52 are the amino acid sequences of the 11E11 CDRs.

11E11-H-CDR1

(SEQ ID NO: 47)

GFSLTNYG

11E11-H-CDR2

(SEQ ID NO: 48)

KWRGGRT

11E11-H-CDR3

(SEQ ID NO: 49)

AKNGPFGNFAGY

11E11-L-CDR1

(SEQ ID NO: 50)

SSQSLLDNQKHY

11E11-L-CDR2

(SEQ ID NO: 51)

WAS

11E11-L-CDR3

(SEQ ID NO: 52)

QQFYNYPYT

SEQ ID NO: 53 is the amino acid sequence of the 11G3 heavy chain variable domain.

QVQLKQSGPSLVQPSQSLSITCTVSGFSLTNYGVHWVRQSPGKGLEWLGVMWRGGRTDYNAAFMSRLSITKDNSRSQVFFKMNSLQTDDA

AIYYCAKNGPFGNFAGYWGQGTLVTVST

SEQ ID NO: 54 is the amino acid sequence of the 11G3 light chain variable domain.

CGDIVMSQSPSSLPVSVGEKVSLTCKSSRSLLDNQKHYLAWYQQKPGQSPKLLIYWASTRESGVPDRFTGSGSGTEFTLTISSVKAEDLA

VYYCQQFYNYPYTFGGGTKLEIK

SEQ ID NO: 55 is an exemplary nucleic acid sequence encoding an 11G3 heavy chain variable domain.

CAGGTGCAGCTGAAGCAGTCAGGACCTAGCCTAGTGCAGCCCTCACAGAGCCTGTCCATAACCTGCACAGTCTCTGGTTTCTCATTAACT

AACTATGGTGTACACTGGGTTCGCCAGTCTCCAGGAAAGGGTCTGGAGTGGCTGGGAGTCATGTGGAGAGGTGGACGCACAGACTACAAT

GCAGCTTTCATGTCCAGACTGAGCATCACCAAGGACAACTCCAGGAGCCAAGTTTTCTTTAAAATGAACAGTCTGCAAACTGATGACGCT

GCCATATACTACTGTGCCAAAAATGGCCCCTTTGGAAACTTCGCTGGTTATTGGGGCCAAGGGACTCTGGTCACTGTCTCTACA

SEQ ID NO: 56 is an exemplary nucleic acid sequence encoding an 11G3 light chain variable domain.

TGTGGGGACATTGTGATGTCACAGTCTCCATCCTCCCTACCTGTGTCAGTTGGAGAGAAGGTTAGTCTGACCTGCAAGTCCAGTCGGAGC

CTTTTAGACAATCAGAAGCACTACTTGGCCTGGTACCAGCAGAAACCAGGGCAGTCTCCTAAACTGCTGATTTACTGGGCATCCACTAGG

GAATCTGGGGTCCCTGATCGCTTCACAGGCAGTGGATCTGGGACAGAATTCACTCTCACTATCAGCAGTGTGAAGGCTGAAGACCTGGCA

GTTTATTACTGTCAGCAATTTTATAACTATCCGTACACGTTCGGAGGGGGGACCAAGCTGGAAATAAAA

-continued

SEQ ID NOs: 47, 57, 49, 58, 51 and 52 are the amino acid sequence of the CDRs of 11G3. Note that some of the CDR sequences are the same as the CDRs of 11E11.

11G3-H-CDR1
(SEQ ID NO: 47)
GFSLTNYG

11G3-H-CDR2
(SEQ ID NO: 57)
MWRGGRT

11G3-H-CDR3
(SEQ ID NO: 49)
AKNGPFGNFAGY

11G3-L-CDR1
(SEQ ID NO: 58)
SSRSLLDNQKHY

11G3-L-CDR2
(SEQ ID NO: 51)
WAS

11G3-L-CDR3
(SEQ ID NO: 52)
QQFYNYPYT

SEQ ID NO: 59 is the amino acid sequence of a linker.

SEQ ID NO: 61 is the amino aid sequence of a signal peptide.

SEQ ID NO: 61 is the amino acid sequence of an immunoglobulin domain.

SEQ ID NO: 62 and 63 are the amino acid sequences of transmembrane domains.

SEQ ID NOs: 64-68 are the amino acid sequences of intracellular domains.

SEQ ID NO: 69 is amino acids 287-302 of EGFR.

DETAILED DESCRIPTION OF SEVERAL EMBODIMENTS

Disclosed herein are monoclonal antibodies and antigen binding fragments thereof that specifically bind EGFRvIII, but do not bind wild-type EGFR expressed on normal cells. Methods of using these antibodies are also disclosed, such as for detection of EGFRvIII, and for inhibiting tumor growth and metastases of tumors and/or decreasing tumor volume. Chimeric antigen receptors and conjugates are disclosed that include these monoclonal antibodies and antigen binding fragments.

Antibodies and antigen binding fragments including the CDRs from monoclonal antibody 40H3 bind EGFRvIII, and also bind mutant EGFR and overexpressed EGFR expressed on tumor cells, but do not bind EGFR expressed on wild-type (not cancerous cells). These antibodies all bind the $EGFR_{287-302}$ loop. Antibodies and antigen binding fragments that include the CDRs from the additional antibodies disclosed herein also specifically bind EGFRvIII, and do not bind wild-type EGFR expressed on wild-type (not cancerous) cells. These antibodies and antigen binding fragments also do not bind other types of EGFR expressed on tumor cells.

Activation of wild-type EGFR involves dimerization which requires ligand binding and a monomer to dimer transition with attendant changes in receptor conformation. There are several structures reported for the extracellular domain of EGFR both in monomer and dimer conformations. Analyses of these structures indicate the presence of residues that are not exposed in the wild type receptor. However, under oncogenic conditions, where receptors are highly expressed and may not be folded correctly or where mutant versions of the receptor are expressed, cryptic structures may become exposed. One structural element that is sterically unavailable under normal conditions is the 287-302 (numbering of mature receptor—or 301-326 of full-length receptor) disulfide-limited loop. This loop is exposed in EGFRvIII and may become exposed when receptor expression is very high or when ECD mutations alter wild type structure. In some embodiments, methods are provided to inhibit a tumor that has this loop exposed on cells.

In some embodiments, the antibody includes the heavy and light chain CDRs of antibody 40H3, and binds to tumor cells that over express EGFR. Thus, methods are provided for inhibiting a tumor over-expressing EGFR in a subject.

In some embodiments, D290 and E293 are required for the antibody or antigen binding fragment to bind the $EGFR_{287-302}$ loop. Exemplary antibodies (such as 1D9, 3D10, 4A4, 9G11 and 11E3) with this binding characteristic are provided. In other embodiments, E293 is required for the antibody or antigen binding fragment to bind the $EGFR_{287-302}$ loop. Exemplary antibodies (such as 11E11) with this binding characteristic are provided. In more embodiments, R300 is required for the antibody or antigen binding fragment to bind the $EGFR_{287-302}$ loop (SEQ ID NO: 69). Exemplary antibodies (such as 40H3) with this binding characteristic are provided.

I. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), The Encyclopedia of Cell Biology and Molecular Medicine, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

About: Unless context indicated otherwise, "about" refers to plus or minus 5% of a reference value. For example, "about" 100 refers to 95 to 105.

Administration: The introduction of a composition into a subject by a chosen route. Administration can be local or systemic. For example, if the chosen route is intravenous, the composition (such as a composition including a disclosed antibody or antigen binding fragment, etc.) is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Agent: Any substance or any combination of substances that is useful for achieving an end or result; for example, a substance or combination of substances useful for inhibiting tumor growth or metastasis in a subject. Agents include proteins, nucleic acid molecules, compounds, small molecules, organic compounds, inorganic compounds, or other molecules of interest. An agent can include a therapeutic agent (such as a chemotherapeutic agent), a diagnostic agent or a pharmaceutical agent. In some embodiments, the agent is an antibody that specifically binds EGFRvIII, an antigen binding fragment thereof, a conjugate thereof, or a chimeric antigen receptor (CAR) including the antibody or antigen binding fragment. The skilled artisan will understand that particular agents may be useful to achieve more than one result.

Amino acid substitutions: The replacement of one amino acid in a polypeptide with a different amino acid or with no amino acid (i.e., a deletion). In some examples, an amino acid in a polypeptide is substituted with an amino acid from a homologous polypeptide, for example, and amino acid in an antibody that specifically binds EGFRvIII or antigen binding fragment thereof can be substituted with the corresponding amino acid from another antibody that specifically binds EGFRvIII or antigen binding fragment thereof.

Antibody and Antigen Binding Fragment: An immunoglobulin, antigen-binding fragment, or derivative thereof, that specifically binds and recognizes an analyte (antigen) such as EGFRvIII. The term "antibody" is used herein in the broadest sense and encompasses various antibody structures, including but not limited to monoclonal antibodies, polyclonal antibodies, multispecific antibodies (e.g., bispecific antibodies), and antigen binding fragments, so long as they exhibit the desired antigen-binding activity.

Non-limiting examples of antibodies include, for example, intact immunoglobulins and variants and antigen binding fragments thereof that retain binding affinity for the antigen. Examples of antigen binding fragments include but are not limited to Fv, Fab, dsFv. Fab', Fab'-SH, $F(ab')_2$; diabodies; linear antibodies; single-chain antibody molecules (e.g. scFv and ds-scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Eds.), *Antibody Engineering*, Vols. 1-2, $2^{nd}$ ed., Springer-Verlag, 2010).

Antibodies also include genetically engineered forms such as chimeric antibodies (such as humanized murine antibodies) and heteroconjugate antibodies (such as bispecific antibodies).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Typically, a naturally occurring immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain). In combination, the heavy and the light chain variable regions specifically bind the antigen.

References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, ds-scFv or Fab.

The $V_H$ and $V_L$ contain a "framework" region interrupted by three hypervariable regions, also called "complementarity-determining regions" or "CDRs" (see, e.g., Kabat et al., *Sequences of Proteins of Immunological Interest,* $5^{th}$ ed., NIH Publication No. 91-3242, Public Health Service, National Institutes of Health, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. (*Sequences of Proteins of Immunological Interest,* $5^{th}$ ed., NIH Publication No. 91-3242, Public Health Service, National Institutes of Health, U.S. Department of Health and Human Services, 1991; "Kabat" numbering scheme), Al-Lazikani et al., ("Standard conformations for the canonical structures of immunoglobulins," *J. Mol. Bio.,* 273(4):927-948, 1997; "Chothia" numbering scheme), and Lefranc et al. ("IMGT unique numbering for immunoglobulin and T cell receptor variable domains and Ig superfamily V-like domains," *Dev. Comp. Immunol.*, 27(1):55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the $V_L$ of the antibody in which it is found. Light chain CDRs are sometimes referred to as LCDR1, LCDR2, and LCDR3. Heavy chain CDRs are sometimes referred to as HCDR1, HCDR2, and HCDR3.

In some embodiments, a disclosed antibody includes a heterologous constant domain. For example, the antibody includes a constant domain that is different from a native constant domain, such as a constant domain including one or more modifications (such as the "LS" mutations) to increase half-life.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject. Monoclonal antibodies can have conservative amino acid substitutions which have substantially no effect on antigen binding or other immunoglobulin functions. (See, for example, Greenfield (Ed.), *Antibodies: A Laboratory Manual*, 2nd ed. New York: Cold Spring Harbor Laboratory Press, 2014.)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel.* 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

Biological sample: A sample obtained from a subject. Biological samples include all clinical samples useful for detection of disease or a tumor (for example, an head and neck cancer, the breast cancer or the bladder cancer) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having a tumor, such as, but not limited to, head and neck cancer, breast cancer or bladder cancer.

Bispecific antibody: A recombinant molecule composed of two different antigen binding domains that consequently binds to two different antigenic epitopes. Bispecific antibodies include chemically or genetically linked molecules of two antigen-binding domains. The antigen binding domains can be linked using a linker. The antigen binding domains can be monoclonal antibodies, antigen-binding fragments (e.g., Fab, scFv, ds-scFv), or combinations thereof. A bispecific antibody can include one or more constant domains but does not necessarily include a constant domain.

Carcinoma: A malignant tumor including transformed epithelial cells. Non-limiting examples of carcinomas include adenocarcinoma, squamous cell carcinoma, anaplastic carcinoma and large and small cell carcinoma. In some examples, a carcinoma is a breast carcinoma, head and neck carcinoma, or bladder carcinoma.

Chemotherapeutic agent: Any chemical agent with therapeutic usefulness in the treatment of diseases characterized by abnormal cell growth. For example, chemotherapeutic agents are useful for the treatment of cancer, including head and neck cancer, breast cancer, and bladder cancer. In one embodiment, a chemotherapeutic agent is an agent of use in treating a carcinoma. Particular examples of additional therapeutic agents that can be used include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. In one embodiment, a chemotherapeutic agent is a radioactive compound. Other examples include the anti-neoplastic drugs 5-fluorouracil (5-FU) and IRT. One of skill in the art can readily identify a chemotherapeutic agent of use (see for example, Slapak and Kufe, *Principles of Cancer Therapy*, Chapter 86 in *Harrison's Principles of Internal Medicine*, 14th edition; Perry et al., *Chemotherapy*, Ch. 17 in Abeloff, Clinical Oncology 2nd ed., © 2000 Churchill Livingstone, Inc; Baltzer, L., Berkery, R. (eds): *Oncology Pocket Guide to Chemotherapy*, 2nd ed. St. Louis, Mosby-Year Book, 1995;

Fischer, D. S., Knobf, M. F., Durivage, H. J. (eds): *The Cancer Chemotherapy Handbook,* 4th ed. St. Louis, Mosby-Year Book, 1993; Chabner and Longo, *Cancer Chemotherapy and Biotherapy: Principles and Practice* (4th ed.). Philadelphia: Lippincott Willians & Wilkins, 2005; Skeel, *Handbook of Cancer Chemotherapy* (6th ed.). Lippincott Williams & Wilkins, 2003). Combination chemotherapy is the administration of more than one agent to treat cancer.

Chimeric antibody: An antibody which includes sequences derived from two different antibodies, such as from different species. In some examples, a chimeric antibody includes one or more CDRs and/or framework regions from one human antibody and CDRs and/or framework regions from another human antibody.

Chimeric Antigen Receptor (CAR): An engineered T cell receptor having an extracellular antibody-derived targeting domain (such as an scFv) joined to one or more intracellular signaling domains of a T cell receptor. A "chimeric antigen receptor T cell" is a T cell expressing a CAR, and has antigen specificity determined by the antibody-derived targeting domain of the CAR. Methods of making CARs (e.g., for treatment of cancer) are available (see, e.g., Park et al., *Trends Biotechnol.,* 29:550-557, 2011; Grupp et al., N Engl J Med., 368:1509-1518, 2013; Han et al., J. Hematol Oncol., 6:47, 2013; PCT Pubs. WO2012/079000, WO2013/059593; and U.S. Pub. 2012/0213783, each of which is incorporated by reference herein in its entirety.)

Conditions sufficient to form an immune complex: Conditions which allow an antibody or antigen binding fragment thereof to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, *Antibodies, A Laboratory Manual,* $2^{nd}$ ed. Cold Spring Harbor Publications, New York (2013) for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Conjugate: A complex of two molecules linked together, for example, linked together by a covalent bond. In one embodiment, an antibody is linked to an effector molecule; for example, an antibody that specifically binds to EGFRvIII covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially affect or decrease a function of a protein, such as the ability of the protein to interact with a target protein. For example, an EGFRvIII-specific antibody can include up to 1, 2, 3, 4, 5, 6, 7, 8, 9, or up to 10 conservative substitutions compared to a reference antibody sequence and retain specific binding activity for EGFRvIII. The term conservative variation also includes the use of a substituted amino acid in place of an unsubstituted parent amino acid.

Individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the EGFRvIII specific antibody, such as the ability to specifically bind to EGFRvIII or bind to a cancer cell expressing EGFRvIII. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as a peptide, that contacts another polypeptide. Contacting can also include contacting a cell for example by placing a polypeptide in direct physical association with a cell.

Control: A reference standard. In some embodiments, the control is a negative control sample obtained from a healthy patient. In other embodiments, the control is a positive control sample obtained from a patient diagnosed with a tumor that expresses EGFRvIII, or recombinantly produced purified EGFRvIII. In still other embodiments, the control is a historical control or standard reference value or range of values (such as a previously tested control sample, such as a group of patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%. In some embodiments, tumor growth, volume and/or metastasis is decreased.

Decrease or Reduce: To reduce the quality, amount, or strength of something; for example a reduction in tumor burden. In one example, a therapy reduces a tumor (such as the size of a tumor, the number of tumors, the metastasis of a tumor, or combinations thereof), or one or more symptoms associated with a tumor, for example as compared to the response in the absence of the therapy. In a particular example, a therapy decreases the size of a tumor, the number of tumors, the metastasis of a tumor, or combinations thereof, subsequent to the therapy, such as a decrease of at least 10%, at least 20%, at least 30%, at least 40%, at least 50%, at least 60%, at least 70%, at least 80%, or at least 90%. Such decreases can be measured using the methods disclosed herein.

Degenerate variant: In the context of the present disclosure, a "degenerate variant" refers to a polynucleotide encoding a polypeptide (such as an antibody) that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). Methods for using detectable markers and guidance in the choice of detectable markers appropriate for various purposes are discussed for example in Green and Sambrook (*Molecular Cloning: A Laboratory Manual,* $4^{th}$ ed., New York: Cold Spring Harbor Laboratory Press, 2012) and Ausubel et al. (Eds.) (*Current Protocols in Molecular Biology*, New York: John Wiley and Sons, including supplements, 2017).

Detecting: To identify the existence, presence, or fact of something.

Effective amount: A quantity of a specific substance sufficient to achieve a desired effect in a subject to whom the substance is administered, such as a therapeutically effective amount, for treatment. For instance, this can be the amount of an antibody necessary to inhibit tumor growth and/or metastasis, or to measurably alter outward symptoms of the tumor.

In some embodiments, administration of an effective amount of a disclosed antibody or antigen binding fragment that binds to EGFRvIII can reduce or inhibit an tumor growth, tumor metastasis, or tumor volume by a desired amount, for example by at least 10%, at least 20%, at least 50%, at least 60%, at least 70%, at least 80%, at least 90%, at least 95%, at least 98%, or even at least 100% (elimination of the tumor), as compared to a suitable control.

The effective amount of an antibody or antigen binding fragment that specifically binds to EGFRvIII that is administered to a subject will vary depending upon a number of factors associated with that subject, for example the overall health and/or weight of the subject. An effective amount can be determined by varying the dosage and measuring the resulting response, such as, for example, a reduction in tumor burden. Effective amounts also can be determined through various in vitro, in vivo or in situ immunoassays.

An effective amount encompasses a fractional dose that contributes in combination with previous or subsequent administrations to attaining an effective response. For example, an effective amount of an agent can be administered in a single dose, or in several doses, for example daily, during a course of treatment lasting several days or weeks. However, the effective amount can depend on the subject being treated, the severity and type of the condition being treated, and the manner of administration. A unit dosage form of the agent can be packaged in an amount, or in multiples of the effective amount, for example, in a vial (e.g., with a pierceable lid) or syringe having sterile components.

Effector molecule: A molecule intended to have or produce a desired effect; for example, a desired effect on a cell to which the effector molecule is targeted. Effector molecules include such molecules as chemical compounds, polypeptides, radioisotopes and small molecules. Non-limiting examples of effector molecules include toxins, chemotherapeutic agents and anti-angiogenic agents. The skilled artisan will understand that some effector molecules may have or produce more than one desired effect. In one example, an effector molecule is the portion of a chimeric molecule, for example a chimeric molecule that includes a disclosed antibody or fragment thereof, that is intended to have a desired effect on a cell to which the chimeric molecule is targeted.

Epidermal Growth Factor Receptor (EGFR): EGFR (also known as HER1 or ERBB1) is a receptor belonging to the ERBB family of the receptor thymidine kinases (RTKs). In vivo, ligand-binding by EGF results in the activation of the RTK/RAS/PI(3)K pathway via receptor phosphorylation, and results in cellular proliferation, angiogenesis, and increased local tissue invasion as well as resistance to apoptosis. A nucleic acid sequence for human EGFR can be found at GENBANK® Accession No. NM_005228.5, Jun. 18, 2019, and GENBANK® Accession No. NC_000007.14 (EGFR in the chromosome), Jun. 14, 2019, both incorporated herein by reference. EGFR has an external domain (ECD) of 621 amino acids, a single pass transmembrane domain (TM) of 23 amino acids and an enzymatically active intracellular domain (ICD) of 542 amino acids. Ligand binding leads to receptor dimer formation and the activation of the kinase domain which signals to one of several pathways that can promote the growth, survival and spread of mammalian cells. In tumors, the loss of exons 2-7 to produces EGFR variant III (EGFRvIII), which is constitutively active. A cDNA sequence for EGFRvIII can be found at GENBANK® Accession No. NM_001346941, Jun. 18, 2019, incorporated herein by reference, and an amino acid sequence can be found at NP_001333870.1, Jun. 14, 2019, incorporated herein by reference. Activation of wild-type EGFR involves dimerization which requires ligand binding and a monomer to dimer transition with attendant changes in receptor conformation. Activating mutations can occur in either the ECD or the ICD. The loss of exon 19 to generate a constitutively active enzyme mutant. EGFR can be overexpressed either by gene amplification of less of transcriptional control. High level expression (such as greater than about 50,000 receptors per cell) leads to either misfolding of the receptor or mutations in one of more of the gene copies. Overexpression can result in a two-fold or greater increase in EGFR present in the cell, as compared to a wild-type control. One structural element that is sterically unavailable under normal conditions is the 287-302 (numbering of mature receptor—or 301-326 of full-length receptor) disulfide-limited loop. This loop is exposed in EGFRvIII and may become exposed when receptor expression is very high or when ECD mutations alter wild type structure, see also FIGS. 1A and 1B and SEQ ID NO: 69.

Epitope: An antigenic determinant. These are particular chemical groups or peptide sequences on a molecule that are antigenic, such that they elicit a specific immune response, for example, an epitope is the region of an antigen to which B and/or T cells respond. An antibody can bind to a particular antigenic epitope, such as an epitope on EGFRvIII.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Fc region: The constant region of an antibody excluding the first heavy chain constant domain. Fc region generally refers to the last two heavy chain constant domains of IgA, IgD, and IgG, and the last three heavy chain constant domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region is typically understood to include immunoglobulin domains Cγ2 and Cγ3 and optionally the lower part of the hinge between Cγ1 and Cγ2. Although the boundaries of the Fc region may vary, the human IgG heavy chain Fc region is usually defined to include residues following C226 or P230 to the Fc carboxyl-terminus, wherein the numbering is according to Kabat. For IgA, the Fc region includes immunoglobulin domains Cα2 and Cα3 and optionally the lower part of the hinge between Cα1 and Cα2.

Framework Region: Amino acid sequences interposed between CDRs in a heavy or light variable region of an antibody. Includes variable light and variable heavy framework regions. The framework regions serve to hold the CDRs in an appropriate orientation.

Heterologous: Originating from a different genetic source. A nucleic acid molecule that is heterologous to a cell originated from a genetic source other than the cell in which it is expressed. In one specific, non-limiting example, a heterologous nucleic acid molecule encoding a protein, such as an scFv, is expressed in a cell, such as a mammalian cell. Methods for introducing a heterologous nucleic acid molecule in a cell or organism are well known in the art, for example transformation with a nucleic acid, including electroporation, lipofection, particle gun acceleration, and homologous recombination.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

IgG: A polypeptide belonging to the class or isotype of antibodies that are substantially encoded by a recognized immunoglobulin gamma gene. In humans, this class comprises $IgG_1$, $IgG_2$, $IgG_3$, and $IgG_4$.

Immune complex: The binding of antibody or antigen binding fragment (such as a scFv) to a soluble antigen forms an immune complex. The formation of an immune complex can be detected through conventional methods, for instance immunohistochemistry, immunoprecipitation, flow cytometry, immunofluorescence microscopy, ELISA, immunoblotting (for example, Western blot), magnetic resonance imaging, CT scans, radiography, and affinity chromatography.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of specific antibodies.

Immunogen: A compound, composition, or substance that can stimulate the production of antibodies or a T cell response in an animal, including compositions that are injected or absorbed into an animal, such as EGFRvIII coupled to a carrier. An immunogen can be used to produce antibodies, such as those disclosed herein.

Inhibiting or Treating a Tumor: A therapeutic intervention (for example, administration of a therapeutically effective amount of an antibody that specifically binds EGFRvIII or a conjugate thereof) that reduces a sign or symptom of a tumor. Treatment can also induce remission, such as reducing the size of a tumor. In particular examples, treatment includes inhibiting metastasis.

The term "reduces" is a relative term, such that an agent reduces a disease or condition if the disease or condition is quantitatively diminished following administration of the agent, or if it is diminished following administration of the agent, as compared to a reference agent. Reducing a sign or symptom refers to any observable beneficial effect of the treatment. Reducing a sign or symptom associated with a tumor can be evidenced, for example, by a delayed onset of clinical symptoms of the disease in a susceptible subject (such as a subject having a tumor which has not yet metastasized), a reduction in severity of some or all clinical symptoms of the disease, a slower progression of the disease (for example by prolonging the life of a subject having tumor), a reduction in the number of tumors or the time between removal of a tumor and the reappearance of the tumor, an improvement in the overall health or well-being of the subject, or by other parameters well known in the art that are specific to the particular tumor. A "prophylactic" treatment is a treatment administered to a subject who does not exhibit signs of a tumor, but has a genetic predisposition to the tumor, or exhibits only early signs, such as a precancerous lesion, for the purpose of decreasing the risk of developing the tumor. The term "prevents" does not necessarily mean that an agent completely eliminates the disease or condition, so long as at least one characteristic of the disease or condition is eliminated. Thus, a composition that reduces or prevents a tumor, can, but does not necessarily completely, prevent risk for developing a tumor.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. An isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Kabat position: A position of a residue in an amino acid sequence that follows the numbering convention delineated by Kabat et al. (*Sequences of Proteins of Immunological Interest,* $5^{th}$ Edition, Department of Health and Human Services, Public Health Service, National Institutes of Health, Bethesda, NIH Publication No. 91-3242, 1991).

Linker: A bi-functional molecule that can be used to link two molecules into one contiguous molecule, for example, to link an effector molecule to an antibody, or a detectable marker to an antibody. Non-limiting examples of peptide linkers include glycine-serine linkers.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. The linkage can be either by chemical or recombinant means. "Chemical means" refers to a reaction between the antibody moiety and the effector molecule such that there is a covalent bond formed between the two molecules to form one molecule.

Neoplasia, cancer, or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue or can metastasize (or both) is referred to as "malignant."

Tumors of the same tissue type are primary tumors originating in a particular organ (such as head and neck, breast, or bladder). Tumors of the same tissue type may be divided into tumors of different sub-types. For examples, lung carcinomas can be divided into adenocarcinomas, small cell, squamous cell, or non-small cell tumors.

Examples of solid tumors, such as sarcomas (connective tissue cancer) and carcinomas (epithelial cell cancer), include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colorectal carcinoma, lymphoid malignancy, pancreatic cancer, breast cancer, head and neck carcinoma, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A first sequence is an "antisense" with respect to a second sequence if a polynucleotide whose sequence is the first sequence specifically hybridizes with a polynucleotide whose sequence is the second sequence.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, PA, 19th Edition, 1995, describes compositions and formulations suitable for pharmaceutical delivery of the disclosed antibodies and antigen binding fragments thereof.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Polypeptide modifications: Polypeptides and peptides, such as the antibodies disclosed herein can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Sambrook et al. (Molecular Cloning: A Laboratory Manual, $4^{th}$ ed, Cold Spring Harbor, New York, 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

As used herein, reference to "at least 80% identity" refers to "at least 80%, at least 85%, at least 90%, at least 91%, at least 92%, at least 93%, at least 94%, at least 95%, at least 96%, at least 97%, at least 98%, at least 99%, or even 100% identity" to a specified reference sequence. As used herein, reference to "at least 90% identity" refers to "at least 90%, at least 91%, at least 92%, at least 93%, at least 94%, at least 95%, at least 96%, at least 97%, at least 98%, at least 99%, or even 100% identity" to a specified reference sequence.

Specifically bind: When referring to an antibody or antigen binding fragment, refers to a binding reaction which determines the presence of a target protein in the presence of a heterogeneous population of proteins and other biologics. Thus, under designated conditions, an antibody binds preferentially to a particular target protein, peptide or polysaccharide (such as an antigen present on the surface of a tumor cell, for example EGFRvIII) and does not bind in a significant amount to other proteins present in the sample or subject, including wild-type EGFR expressed on wild-type (non-tumor) cells from the same tissue. In other embodiments, an antibody can specifically bind EGFRvIII and forms of EGFR that are overexpressed on tumor cells, but does not bind wild-type EGFR expressed on wild-type (non-tumor) cells of the same tissue. Specific binding can be determined by standard methods. See Harlow & Lane, *Antibodies, A Laboratory Manual,* $2^{nd}$ ed., Cold Spring Harbor Publications, New York (2013), for a description of immunoassay formats and conditions that can be used to determine specific immunoreactivity.

With reference to an antibody-antigen complex, specific binding of the antigen and antibody has a $K_D$ of less than about $10^{-7}$ Molar, such as less than about $10^{-8}$ Molar, $10^{-9}$, or even less than about $10^{-10}$ Molar. $K_D$ refers to the dissociation constant for a given interaction, such as a polypeptide ligand interaction or an antibody antigen interaction. For example, for the bimolecular interaction of an antibody or antigen binding fragment and an antigen it is the concentration of the individual components of the bimolecular interaction divided by the concentration of the complex.

An antibody that specifically binds to an epitope on EGFRvIII is an antibody that binds substantially to EGFRvIII protein, including cells or tissue expressing EGFRvIII, substrate to which EGFRvIII is attached, or EGFRvIII in a biological specimen or isolated from a biological specimen. It is, of course, recognized that a certain degree of non-specific interaction may occur between an antibody and a non-target (such as a cell of the same tissue type that does not express wild-type EGFR). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein.

Subject: Living multi-cellular vertebrate organisms, a category that includes human and non-human mammals. In an example, a subject is a human. In a particular example, the subject has a cancer. In an additional example, a subject is selected that is in need of inhibiting of growth of a tumor or metastasis. For example, the subject has be diagnosed with a tumor that expresses EGFRvIII, such as a head and neck, breast or bladder carcinoma, and is in need of treatment.

T Cell: A white blood cell critical to the immune response. T cells include, but are not limited to, $CD4^+$ T cells and $CD8^+$ T cells. A $CD4^+$ T lymphocyte is an immune cell that expresses CD4 on its surface. These cells, also known as helper T cells, help orchestrate the immune response, including antibody responses as well as killer T cell responses. Th1 and Th2 cells are functional subsets of helper T cells. Th1 cells secrete a set of cytokines, including interferon-gamma, and whose principal function is to stimulate phagocyte-mediated defense against infections, especially related to intracellular microbes. Th2 cells secrete a set of cytokines, including interleukin (IL)-4 and IL-5, and whose principal functions are to stimulate IgE and eosinophil/mast cell-mediated immune reactions and to downregulate Th1 responses.

Therapeutic agent: Used in a generic sense, it includes treating agents, prophylactic agents, and replacement agents. A therapeutic agent is used to ameliorate a specific set of conditions in a subject with a disease or a disorder.

Treating or preventing a disease: Inhibiting the full development of a disease or condition, for example, in a subject who is at risk of or has a disease such as a tumor. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Toxin: An effector molecule that induces cytotoxicity when it contacts a cell. Specific, non-limiting examples of toxins include, but are not limited to, abrin, ricin, auristatins (such as monomethyl auristatin E (MMAE; see for example, Francisco et al., Blood, 102: 1458-1465, 2003)) and monomethyl auristatin F (MMAF; see, for example, Doronina et al., BioConjugate Chem., 17: 114-124, 2006), maytansinoids (such as DM1; see, for example, Phillips et al., Cancer Res., 68:9280-9290, 2008), *Pseudomonas* exotoxin (PE, such as PE35, PE37, PE38, and PE40), diphtheria toxin (DT), botulinum toxin, saporin, restrictocin or gelonin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody.

Transformed: A transformed cell is a cell into which a nucleic acid molecule has been introduced by molecular biology techniques. As used herein, the term transformed and the like (e.g., transformation, transfection, transduction, etc.) encompasses all techniques by which a nucleic acid molecule might be introduced into such a cell, including transduction with viral vectors, transformation with plasmid vectors, and introduction of DNA by electroporation, lipofection, and particle gun acceleration.

Vector: An entity containing a nucleic acid molecule (such as a DNA or RNA molecule) bearing a promoter(s) that is operationally linked to the coding sequence of a protein of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements. Viral vectors are recombinant nucleic acid vectors having at least some nucleic acid sequences derived from one or more viruses. In some embodiments, a viral vector comprises a nucleic acid molecule encoding a disclosed antibody or antigen binding fragment that specifically binds EGFRvIII.

Under conditions sufficient for: A phrase that is used to describe any environment that permits a desired activity.

II. Description of Several Embodiments

Isolated monoclonal antibodies and antigen binding fragments thereof that specifically EGFRvIII are provided. In several embodiments, the antibodies and antigen binding fragments can be used to treat a tumor that expresses EGFRvIII, such as, but not limited to a head and neck carcinoma, breast carcinoma, or bladder carcinoma. Also disclosed herein are compositions including the antibodies and antigen binding fragments and a pharmaceutically acceptable carrier. Nucleic acids encoding the antibodies or antigen binding fragments, expression vectors including these nucleic acids, and isolated host cells that express the nucleic acids are also provided.

Compositions comprising the monoclonal antibodies that specifically bind EGFRvIII, and antigen binding fragments thereof, can be used for research, diagnostic and therapeutic purposes. For example, the monoclonal antibodies can be used to diagnose or treat a subject that has a tumor that express EGFRvIII.

A. Antibodies and Antigen Binding Fragments

Isolated monoclonal antibodies and antigen binding fragments that specifically bind an epitope of EGFRvIII are provided. In several embodiments, the antibodies and antigen binding fragments can inhibit a biological function or property of EGFRvIII protein in vivo, including, but not limited to, a reduction and/or inhibition of tumor growth, or a reduction and/or inhibition of tumor metastasis. Several monoclonal antibodies are disclosed herein that bind EGFRvIII, and do not bind wild-type EGFR. In addition, monoclonal antibody 40H3 binds EGFR when overexpressed on tumor cells, but not on wild-type cells.

One structural element that is sterically unavailable under normal conditions is the 287-302 (numbering of mature receptor—or 301-326 of full-length receptor) disulfide-limited loop, which is exposed in EGFRvIII. In some embodiments, D290 and E293 are required for the antibody or antigen binding fragment to bind the $EGFR_{287-302}$ loop. Exemplary antibodies (such as 1D9, 3D10, 4A4, 9G11 and 11E3) with this binding characteristic are provided. In other embodiments, E293 is required for the antibody or antigen binding fragment to bind the $EGFR_{287-302}$ loop. Exemplary antibodies (such as 11E11) with this binding characteristic are provided. In more embodiments, R300 is required for the antibody or antigen binding fragment to bind the $EGFR_{287-302}$ loop. Exemplary antibodies (such as 40H3) with this binding characteristic are provided. The disclosed antibodies can be chimeric or humanized, and thus include one or more heterologous framework regions.

In some embodiments, the EGFRvIII specific antibodies include a variable heavy chain region ($V_H$) and a variable light chain region ($V_L$) and specifically bind EGFRvIII. In several embodiments, the monoclonal antibodies include a $V_H$ comprising a heavy chain complementarity determining region (HCDR)1, a HCDR2 and an HCDR3, and a $V_L$ comprising a light chain complementarity determining region (LCDR)1, LCDR2 and LCDR3.

In some embodiments, the antibody or antigen binding fragment can specifically bind to an epitope of EGFR, such as the $EGFR_{287-302}$ loop, and are neutralizing. In several embodiments, the antibody or antigen binding fragment thereof includes a $V_H$ and a $V_L$ including the HCDR1, HCDR2, and HCDR3, and LCDR1, LCDR2, and LCDR3, respectively, of one of the disclosed antibodies.

The discussion of monoclonal antibodies below refers to isolated monoclonal antibodies that include a $V_H$ and a $V_L$ that each include at least one CDR. The person of ordinary skill in the art will understand that various CDR numbering schemes (such as the Kabat, Chothia or IMGT numbering schemes) can be used to determine CDR positions. The amino acid sequence and the CDR positions of the heavy and light chain of the disclosed monoclonal antibodies are shown herein using IGMT numbering. However, the person of skill in the art will readily understand use of various CDR numbering schemes when referencing particular amino acids of the antibodies disclosed herein. Programs for the identification of CDRs using Chothia and Kabbat are available on the internet.

In some embodiments, the isolated monoclonal antibody or antigen binding fragment thereof includes one of: a) a $V_H$ and a $V_L$ including a HCDR1, a HCDR2, and a HCDR3, and a LCDR1, a LCDR2, and a LCDR3 of the $V_H$ and $V_L$ set forth as SEQ ID NOs: 1 and 2, respectively; [40H3] b) $V_H$ and an $V_L$ including a HCDR1, a HCDR2, and a HCDR3, and a LCDR1, a LCDR2, and a LCDR3 of the $V_H$ and $V_L$ set forth as SEQ ID NOs: 11 and 12, respectively; [3D10/9G11 consensus] c) a $V_H$ and a $V_L$ including a HCDR1, a HCDR2, and a HCDR3, and a LCDR1, a LCDR2, and a LCDR3 of the $V_H$ and $V_L$ set forth as SEQ ID NOs: 13 and 14, respectively[1D9/4A4 consensus]; or d) a $V_H$ and a $V_L$ including a HCDR1, a HCDR2, and a HCDR3, and a LCDR1, a LCDR2, and a LCDR3 of the $V_H$ and $V_L$ set forth as SEQ ID NOs: 15 and 16, respectively [11E11/11G3 consensus]. The CDRs can be identified, for example, using IMGT, Kabat or Chothia. In other embodiments, the isolated monoclonal antibody or antigen binding fragment thereof includes one of: a) a $V_H$ and a $V_L$ including a HCDR1, a HCDR2, and a HCDR3, and a LCDR1, a LCDR2, and a LCDR3 of the $V_H$ and $V_L$ set forth as SEQ ID NOs: 17 and 12, respectively; [3D10] b) a $V_H$ and a $V_L$ including a HCDR1, a HCDR2, and a HCDR3, and a LCDR1, a LCDR2, and a LCDR3 of the $V_H$ and $V_L$ set forth as SEQ ID NOs: 26 and 12, respectively; [9G11] c) a $V_H$ and a $V_L$ including a HCDR1, a HCDR2, and a HCDR3, and a LCDR1, a LCDR2, and a LCDR3 of the $V_H$ and $V_L$ set forth as SEQ ID NOs: 29 and 30, respectively; [1D9] d) $V_H$ and an $V_L$ including a HCDR1, a HCDR2, and a HCDR3, and a LCDR1, a LCDR2, and a LCDR3 of the $V_H$ and $V_L$ set forth as set forth as SEQ ID NOs: 39 and 40, respectively; [4A4] e) $V_H$ and an $V_L$ including a HCDR1, a HCDR2, and a HCDR3, and a LCDR1, a LCDR2, and a LCDR3 of the $V_H$ and $V_L$ set forth as SEQ ID NOs: 43 and 44, respectively; [11E11] or f) $V_H$ and an $V_L$ including a HCDR1, a HCDR2, and a HCDR3, and a LCDR1, a LCDR2, and a LCDR3 of the $V_H$ and $V_L$ set forth as SEQ ID NOs: 53 and 54, respectively; [11G3]. The CDRs can be identified, for example, using IMGT, Kabat or Chothia.

In some non-limiting examples, a) the HCDR1, the HCDR2, the HCDR3, the LCDR1, the LCDR2, and the LCDR3 include the amino acids sequences set forth as SEQ ID NOs: 5, 6, 7, 8, 9 and 10, respectively [40H3]; b) the HCDR1, the HCDR2, the HCDR3, the LCDR1, the LCDR2, and the LCDR3 include the amino acids sequences set forth as SEQ ID NOs: 20, 21, 22, 23, 24 and 25, respectively [3D10]; c) the HCDR1, the HCDR2, the HCDR3, the LCDR1, the LCDR2, and the LCDR3 include the amino acids sequences set forth as SEQ ID NOs: 20, 28, 22, 23, 24 and 25, respectively [9G11]; d) the HCDR1, the HCDR2, the HCDR3, the LCDR1, the LCDR2, and the LCDR3 include the amino acids sequences set forth as SEQ ID NOs: 33, 34, 35, 36, 37 and 38 respectively [1D9 and 4A4]; e) the HCDR1, the HCDR2, the HCDR3, the LCDR1, the LCDR2, and the LCDR3 include the amino acids sequences set forth as SEQ ID NOs: 47, 48, 49, 50, 51 and 52, respectively [11E11]; or f) the HCDR1, the HCDR2, the HCDR3, the LCDR1, the LCDR2, and the LCDR3 include the amino acids sequences set forth as SEQ ID NOs: 47, 57, 49, 58, 51 and 52 respectively [11G3]. In these embodiments, the monoclonal antibody or antigen binding fragment specifically binds EGFRvIII. In one non-limiting example, the HCDR1, the HCDR2, the HCDR3, the LCDR1, the LCDR2, and the LCDR3 include the amino acids sequences set forth as SEQ ID NOs: 5, 6, 7, 8, 9 and 10 [40H3] and the monoclonal antibody or antigen binding fragment also binds EGFR overexpressed on tumor cells.

In some embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 1 and 2, respectively [40H3]. In other embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 17 and 12, respectively [3D10]. In more embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 26 and 12, respectively [9G11]. In further embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 29 and 30, respectively [1D9]. In yet other embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 39 and 40, respectively [4A4]. In more embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 43 and 44, respectively [11E11]. In further embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 53 and 54, respectively [11G3]. In these embodiments, the monoclonal antibody or antigen binding fragment specifically binds EGFRvIII. In one non-limiting example, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 1 and 2, and the monoclonal antibody or antigen binding fragment also binds EGFR overexpressed on tumor cells.

In some embodiments, the $V_H$ and the $V_L$ include amino acid sequences 95%, 96%, 97%, 98%, or 99% to the amino acid sequences set forth as SEQ ID NOs: 1 and 2, respectively [40H3]. In other embodiments, the $V_H$ and the $V_L$ include amino acid sequences 95%, 96%, 97%, 98%, or 99% to the amino acid sequences set forth as SEQ ID NOs: 17 and 12, respectively [3D10]. In more embodiments, the $V_H$ and the $V_L$ include amino acid sequences 95%, 96%, 97%, 98%, or 99% to the amino acid sequences set forth as SEQ ID NOs: 26 and 12, respectively [9G11]. In further embodiments, the $V_H$ and the $V_L$ include amino acid sequences 95%, 96%, 97%, 98%, or 99% to the amino acid sequences set forth as SEQ ID NOs: 29 and 30, respectively [1D9]. In yet other embodiments, the $V_H$ and the $V_L$ include amino acid sequences 95%, 96%, 97%, 98%, or 99% to the amino acid sequences set forth as SEQ ID NOs: 39 and 40, respectively [4A4]. In more embodiments, the $V_H$ and the $V_L$ include amino acid sequences 95%, 96%, 97%, 98%, or 99% to the amino acid sequences set forth as SEQ ID NOs: 43 and 44, respectively [11E11]. In further embodiments, the $V_H$ and the include amino acid sequences 95%, 96%, 97%, 98%, or 99% to the amino acid sequences set forth as SEQ ID NOs: 53 and 54, respectively [11G3]. In these embodiments, the monoclonal antibody or antigen binding fragment specifically binds EGFRvIII. In one non-limiting example, the $V_H$ and the $V_L$ include amino acid sequences 95%, 96%, 97%, 98%, or 99% to the amino acid sequences set forth as SEQ ID NOs: 1 and 2, and the monoclonal antibody or antigen binding fragment also binds EGFR overexpressed on tumor cells.

In more embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 1 and 2, and the HCDR1, the HCDR2, the HCDR3, the LCDR1, the LCDR2, and the LCDR3 include the amino acids sequences set forth as SEQ ID NOs: 5, 6, 7, 8, 9 and 10, respectively [40H3]. In other embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 17 and 12, and the HCDR1, the HCDR2, the HCDR3, the LCDR1, the LCDR2, and the LCDR3 include the amino acids sequences set forth as SEQ ID NOs: 20, 21, 22, 23, 24 and 25, respectively [3D10]. In more embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 26 and 12, and the HCDR1, the HCDR2, the HCDR3, the LCDR1, the LCDR2, and the LCDR3 include the amino acids sequences set forth as SEQ ID NOs: 20, 28, 22, 23, 24 and 25, respectively [9G11]. In further embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 29 and 30, the HCDR1, the HCDR2, the HCDR3, the LCDR1, the LCDR2, and the LCDR3 include the amino acids sequences set forth as SEQ ID NOs: 33, 34, 35, 36, 37 and 38 respectively [1D9]. In yet other embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 39 and 40, the HCDR1, the HCDR2, the HCDR3, the LCDR1, the LCDR2, and the LCDR3 include the amino acids sequences set forth as SEQ ID NOs: 33, 34, 35, 36, 37 and 38 respectively [4A4]. In more embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 43 and 44, and the HCDR1, the HCDR2, the HCDR3, the LCDR1, the LCDR2, and the LCDR3 include the amino acids sequences set forth as SEQ ID NOs: 47, 48, 49, 50, 51 and 52, respectively [11E11]. In further embodiments, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 53 and 54, and the HCDR1, the HCDR2, the HCDR3, the LCDR1, the LCDR2, and the LCDR3 include the amino acids sequences set forth as SEQ ID NOs: 47, 57, 49, 58, 51 and 52, respectively [11G3]. In these embodiments, the monoclonal antibody or antigen binding fragment specifically binds EGFRvIII. In one non-limiting example, the $V_H$ and the $V_L$ include the amino acid sequences at least 90% identical (such as at least 95%, at least 96%, at least 97%, at least 98%, or at least 99%) to the amino acid sequences set forth as SEQ ID NOs: 1 and 2, the HCDR1, the HCDR2, the HCDR3, the LCDR1, the LCDR2, and the LCDR3 include the amino acids sequences set forth as SEQ ID NOs: 5, 6, 7, 8, 9 and 10, respectively, and the monoclonal antibody or antigen binding fragment also binds EGFR overexpressed on tumor cells.

In some embodiments, the monoclonal antibody or antigen binding fragment includes a $V_H$ and the $V_L$ that include the amino acid sequences set forth as SEQ ID NOs: 1 and 2, respectively. In other embodiments, the monoclonal antibody or antigen binding fragment includes a $V_H$ and the $V_L$ that include the amino acid sequences set forth as SEQ ID NOs: 17 and 12, respectively. In more embodiments, the monoclonal antibody or antigen binding fragment includes a $V_H$ and the $V_L$ that include the amino acid sequences set forth as SEQ ID NOs: 26 and 12, respectively. In additional embodiments, the monoclonal antibody or antigen binding fragment includes a $V_H$ and the $V_L$ that include the amino acid sequences set forth as SEQ ID NOs: 29 and 30, respectively. In further embodiments, the monoclonal antibody or antigen binding fragment includes a $V_H$ and the $V_L$ that include the amino acid sequences set forth as SEQ ID NOs: 39 and 40, respectively. In more embodiments, the monoclonal antibody or antigen binding fragment includes a $V_H$ and the $V_L$ that include the amino acid sequences set forth as SEQ ID NOs: 43 and 44, respectively. In other embodiments, the monoclonal antibody or antigen binding fragment includes a $V_H$ and the $V_L$ that include the amino acid sequences set forth as SEQ ID NOs: 53 and 54. In these embodiments, the monoclonal antibody or antigen binding fragment specifically binds EGFRvIII. In one non-limiting example, the $V_H$ and the $V_L$ include the amino acid sequences set forth as SEQ ID NO: 1 and SEQ ID NO: 2, respectively, and the monoclonal antibody or antigen binding fragment also binds EGFR overexpressed on tumor cells.

1. Additional Description of Antibodies and Antigen Binding Fragments

An antibody or antigen binding fragment can be a humanized antibody or antigen binding fragment thereof. The antibody or antigen binding fragment can include any suitable framework region, such as (but not limited to) one or more human framework region. Human framework regions, and mutations that can be made in a human antibody framework regions, are known in the art (see, for example, in U.S. Pat. No. 5,585,089, which is incorporated herein by reference). Chimeric antibodies are also provided. The heterologous framework region, such as, but not limited to a different mouse framework region, can be included in the heavy or light chain of the antibodies. (See, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., J. *Immunol.* 150:2844, 1993.)

The antibody can be of any isotype. The antibody can be, for example, an IgM or an IgG antibody, such as $IgG_1$, IgG2, IgG3, or IgG4. The class of an antibody that specifically binds EGFRvIII can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. A nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds EGFRvIII, that was originally IgG may be class switched. Class switching can be used to convert one IgG subclass to another, such as from $IgG_1$ to $IgG_2$, $IgG_3$, or $IgG_4$.

In some examples, the disclosed antibodies are oligomers of antibodies, such as dimers, trimers, tetramers, pentamers, hexamers, septamers, octomers and so on.

(a) Binding Affinity

In several embodiments, the antibody or antigen binding fragment can specifically bind EGFRvIII protein with an affinity (e.g., measured by $K_d$) of no more than $1.0\times10^{-8}$ M, no more than $5.0\times10^{-8}$ M, no more than $1.0\times10^{-9}$ M, no more than $5.0\times10^{-9}$ M, no more than $1.0\times10^{-10}$ M, no more than $5.0\times10^{-10}$ M, or no more than $1.0\times10^{-11}$ M. $K_d$ can be measured, for example, by a radiolabeled antigen binding assay (RIA) performed with the Fab version of an antibody of interest and its antigen using known methods. In one assay, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 μM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed, and the plate washed eight times with 0.1% polysorbate 20 (TWEEN-20@) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

In another assay, $K_d$ can be measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE®, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 l/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 l/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds 106 $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

(b) Multispecific Antibodies

In some embodiments, the antibody or antigen binding fragment is included on a multispecific antibody, such as a bi-specific antibody. Such multispecific antibodies can be produced by known methods, such as crosslinking two or more antibodies, antigen binding fragments (such as scFvs) of the same type or of different types. Exemplary methods of making multispecific antibodies include those described in PCT Pub. No. WO2013/163427, which is incorporated by reference herein in its entirety. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

In some embodiments, the antibody or antigen binding fragment is included on a bispecific antibody that that specifically binds to EGFRvIII and further specifically binds to a tumor antigen, such as Her-2, or a checkpoint inhibitor, such as programmed death (PD)-1 or PD ligand (PD-L1) or PD-L2.

Various types of multi-specific antibodies are known. Bispecific single chain antibodies can be encoded by a single nucleic acid molecule. Examples of bispecific single chain antibodies, as well as methods of constructing such antibodies are known in the art (see, e.g., U.S. Pat. Nos. 8,076,459, 8,017,748, 8,007,796, 7,919,089, 7,820,166, 7,635,472, 7,575,923, 7,435,549, 7,332,168, 7,323,440, 7,235,641, 7,229,760, 7,112,324, 6,723,538, incorporated by reference herein). Additional examples of bispecific single chain antibodies can be found in PCT application No. WO 99/54440; Mack, *J. Immunol.,* 158:3965-3970, 1997; Mack, *PNAS,* 92:7021-7025, 1995; Kufer, *Cancer Immunol. Immunother.,* 45:193-197, 1997; Loffler, *Blood,* 95:2098-2103, 2000; and Bruhl, *J. Immunol.,* 166:2420-2426, 2001. Production of bispecific Fab-scFv ("bibody") molecules are described, for example, in Schoonjans et al. (J. Immunol. 165:7050-57, 2000) and Willems et al. (J Chromatogr B Analyt Technol Biomed Life Sci. 786:161-76, 2003). For bibodies, a scFv molecule can be fused to one of the VL-CL (L) or VH-CH1 chains, e.g., to produce a bibody one scFv is fused to the C-term of a Fab chain.

(c) Antigen Binding Fragments

Antigen binding fragments are encompassed by the present disclosure, such as Fab, $F(ab')_2$, and Fv, which include a heavy chain and light chain variable region and specifically bind EGFRvIII. These antibody fragments retain the ability to selectively bind with the antigen and are "antigen-binding" fragments. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, a genetically engineered fragment containing the variable region of the light chain and the variable region of the heavy chain expressed as two chains and disulfide linked forms thereof (dsFV); and (5) Single chain antibody (such as scFv), defined as a genetically engineered molecule containing the variable region of the light chain, the variable region of the heavy chain, linked by a suitable polypeptide linker as a genetically fused single chain molecule. A scFv is a fusion protein in which a light chain variable region of an immunoglobulin and a heavy chain variable region of an immunoglobulin are bound by a linker (see, e.g., Ahmad et al., Clin. Dev. Immunol., 2012, doi:10.1155/2012/980250; Marbry, IDrugs, 13:543-549, 2010). The intramolecular orientation of the $V_H$-domain and the $V_L$-domain in a scFv, is not decisive for the provided antibodies (e.g., for the provided multispecific antibodies). Thus, scFvs with both possible arrangements ($V_H$-domain-linker domain-$V_L$-domain; $V_L$-domain-linker domain-$V_H$-domain) may be used. Other forms, such as ds-scFv are also of use.

(6) A dimer of a single chain antibody ($scFV_2$), defined as a dimer of a scFV. This has also been termed a "miniantibody."

Methods of making these fragments are known in the art (see for example, Harlow and Lane, *Antibodies: A Laboratory Manual,* 2nd, Cold Spring Harbor Laboratory, New York, 2013).

In a further group of embodiments, the antibody binding fragment can be an Fv antibody, which is typically about 25 kDa and contain a complete antigen-binding site with three CDRs per each heavy chain and each light chain. To produce Fv antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a nucleic acid molecule encoding the $V_H$ and $V_L$ domains connected by an oligonucleotide. The nucleic acid molecule is inserted into an expression vector, which is subsequently introduced into a host cell such as a mammalian cell. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; Ahmad et al., *Clin. Dev. Immunol.,* 2012, doi:10.1155/2012/980250; Marbry, IDrugs, 13:543-549, 2010). Dimers of a single chain antibody ($scFV_2$), are also contemplated.

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Antigen binding single $V_H$ domains, called domain antibodies (dAb), have also been identified from a library of murine $V_H$ genes amplified from genomic DNA of immunized mice (Ward et al. *Nature* 341:544-546, 1989). Human single immunoglobulin variable domain polypeptides capable of binding antigen with high affinity have also been described (see, for example, PCT Publication Nos. WO 2005/035572 and WO 2003/002609). The CDRs disclosed herein can also be included in a dAb.

In some embodiments, one or more of the heavy and/or light chain complementarity determining regions (CDRs) from a disclosed antibody is expressed on the surface of another protein, such as a scaffold protein. The expression of domains of antibodies on the surface of a scaffolding protein are known in the art (see e.g. Liu et al., *J. Virology* 85(17): 8467-8476, 2011). Such expression creates a chimeric protein that retains the binding for EGFRvIII. In some specific embodiments, one or more of the heavy chain CDRs is grafted onto a scaffold protein, such as one or more of heavy chain CDR1, CDR2, and/or CDR3. One or more CDRs can also be included in a diabody or another type of single chain antibody molecule.

(d) Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the CDRs and the framework regions. Amino acid substitutions may be introduced into an antibody of interest and the products screened for a desired activity, e.g., retained/improved antigen binding, decreased immunogenicity, or improved ADCC or CDC.

The variants typically retain amino acid residues necessary for correct folding and stabilizing between the $V_H$ and the $V_L$ regions and retain the charge characteristics of the residues in order to preserve the low pI and low toxicity of the molecules. Amino acid substitutions can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

In some embodiments, the heavy chain of the antibody includes up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NOs 1, 11, 13, 15, 17, 26, 29, 39, 43 or 53. In some embodiments, the light chain of the antibody includes up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NOs: 2, 12, 14, 16, 30, 40, 44 or 54.

In some embodiments, the antibody or antigen binding fragment can include up to 10 (such as up to 1, up to 2, up to 3, up to 4, up to 5, up to 6, up to 7, up to 8, or up to 9) amino acid substitutions (such as conservative amino acid substitutions) in the framework regions of the heavy chain of the antibody, and/or the light chain of the antibody, or the heavy and light chains of the antibody, compared to a known framework region, or compared to the framework regions of the antibodies as disclosed herein, and maintain the specific binding activity for EGFRvIII protein.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In certain embodiments of the variant $V_H$ and VL sequences provided above, each CDR either is unaltered, or contains no more than one, two or three amino acid substitutions.

To increase binding affinity of the antibody, the $V_L$ and $V_H$ segments can be randomly mutated, such as within H-CDR3 region or the L-CDR3 region, in a process analogous to the in vivo somatic mutation process responsible for affinity maturation of antibodies during a natural immune response. Thus in vitro affinity maturation can be accomplished by amplifying $V_H$ and $V_L$ regions using PCR primers complementary to the H-CDR3 or L-CDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity for EGFRvIII. Methods of in vitro affinity maturation are known (see, e.g., Chowdhury, *Methods Mol. Biol.* 207:179-196 (2008)), and Hoogenboom et al. in *Methods in Molecular Biology* 178:1-37 (O'Brien et al., ed., Human Press, Totowa, N.J., (2001).)

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

In certain embodiments, an antibody or antigen binding fragment is altered to increase or decrease the extent to which the antibody or antigen binding fragment is glycosylated. Addition or deletion of glycosylation sites may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region; however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/

084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lee 13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In several embodiments, the constant region of the antibody includes one or more amino acid substitutions to optimize in vivo half-life of the antibody. The serum half-life of IgG Abs is regulated by the neonatal Fc receptor (FcRn). Thus, in several embodiments, the antibody includes an amino acid substitution that increases binding to the FcRn. Several such substitutions are known to the person of ordinary skill in the art, such as substitutions at IgG constant regions T250Q and M428L (see, e.g., Hinton et al., *J Immunol.,* 176:346-356, 2006); M428L and N434S (the "LS" mutation, see, e.g., Zalevsky, et al., *Nature Biotechnology,* 28:157-159, 2010); N434A (see, e.g., Petkova et al., *Int. Immunol.,* 18:1759-1769, 2006); T307A, E380A, and N434A (see, e.g., Petkova et al., *Int. Immunol.,* 18:1759-1769, 2006); and M252Y, S254T, and T256E (see, e.g., Dall'Acqua et al., *J. Biol. Chem.,* 281:23514-23524, 2006).

In some embodiments, the constant region of the antibody includes one of more amino acid substitutions to optimize Antibody-dependent cell-mediated cytotoxicity (ADCC). ADCC is mediated primarily through a set of closely related Fcγ receptors. In some embodiments, the antibody includes one or more amino acid substitutions that increase binding to FcγRIIIa. Several such substitutions are known to the person of ordinary skill in the art, such as substitutions at IgG constant regions S239D and 1332E (see, e.g., Lazar et al., *Proc. Natl., Acad. Sci. U.S.A.,* 103:4005-4010, 2006); and S239D, A330L, and 1332E (see, e.g., Lazar et al., *Proc. Natl., Acad. Sci. U.S.A.,* 103:4005-4010, 2006).

Combinations of the above substitutions are also included, to generate an IgG constant region with increased binding to FcRn and FcγRIIIa. The combinations increase antibody half-life and ADCC. For example, such combination include antibodies with the following amino acid substitution in the Fc region: (1) S239D/1332E and T250Q/M428L; (2) S239D/1332E and M428L/N434S; (3) S239D/1332E and N434A; (4) S239D/1332E and T307A/E380A/N434A; (5) S239D/1332E and M252Y/S254T/T256E; (6) S239D/A330L/1332E and T250Q/M428L; (7) S239D/A330L/1332E and M428L/N434S; (8) S239D/A330L/1332E and N434A; (9) S239D/A330L/1332E and T307A/E380A/N434A; or (10) S239D/A330L/1332E and M252Y/S254T/T256E.

In some examples, the antibodies, or an antigen binding fragment thereof is modified such that it is directly cytotoxic to infected cells, or uses natural defenses such as complement, antibody dependent cellular cytotoxicity (ADCC), or phagocytosis by macrophages.

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

The antibody or antigen binding fragment can be derivatized or linked to another molecule (such as another peptide or protein). In general, the antibody or antigen binding fragment is derivatized such that the binding to EGFRvIII is not affected adversely by the derivatization or labeling. For example, the antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

Also included are antibodies that bind to the same epitope on EGFRvIII to which the disclosed antibodies provided herein bind. Antibodies that bind to such an epitope on the $EGFR_{287-302}$ loop can be identified based on their ability to cross-compete (for example, to competitively inhibit the binding of, in a statistically significant manner) with the specific antibodies provided herein in binding assays (such as those described in the Examples). An antibody "competes" for binding when the competing antibody inhibits $EGFR_{287-302}$ loop binding of an antibody of the present disclosure by more than 50%, in the presence of competing antibody concentrations higher than $106\times K_D$ of the competing antibody. In a certain embodiment, the antibody that binds to the same epitope on the $EGFR_{287-302}$ loop as the antibodies of the present disclosure is a human monoclonal antibody. Such human monoclonal antibodies can be prepared and isolated as described herein.

B. Conjugates

Human monoclonal antibodies specific for EGFRvIII, or antigen binding fragments thereof, can be conjugated to an agent, such as an effector molecule or detectable marker, using any number of means known to those of skill in the art. Both covalent and non-covalent attachment means may be used. Conjugates include, but are not limited to, molecules in which there is a covalent linkage of an effector molecule or a detectable marker to an antibody or antigen binding fragment that specifically binds EGFRvIII. One of skill in the art will appreciate that various effector molecules and detectable markers can be used, including (but not limited to) chemotherapeutic agents, anti-angiogenic agents, toxins, radioactive agents such as $^{125}I$, $^{32}P$, $^{14}C$, $^{3}H$ and $^{35}S$ and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

Effector molecules and detectable markers can be linked to an antibody or antigen binding fragment of interest using any number of means known to those of skill in the art. Both covalent and non-covalent attachment means may be used. The procedure for attaching an effector molecule or detectable marker to an antibody or antigen binding fragment varies according to the chemical structure of the effector. Polypeptides typically contain a variety of functional groups; such as carboxylic acid (COOH), free amine ($—NH_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, IL. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

Additionally, in several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference in its entirety.

Thus, in several embodiments, the conjugate includes a linker that connects the effector molecule or detectable marker to the EGFRvIII-specific antibody or antigen binding fragment thereof. In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15, amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med- Chem. 3(10):1299-1304), or a 3-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 2005/0238649, and U.S. Publication No. 2006/0024317, each of which is incorporated by reference herein in its entirety.

The antibodies or antigen binding fragments disclosed herein can be derivatized, for example, by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

In view of the large number of methods that have been reported for attaching a variety of radiodiagnostic compounds, radiotherapeutic compounds, labels (such as enzymes or fluorescent molecules), toxins, and other agents to antibodies one skilled in the art will be able to determine a suitable method for attaching a given agent to an antibody or antigen binding fragment or other polypeptide. For example, the antibody or antigen binding fragment can be conjugated with small molecular weight drugs such as Monomethyl Auristatin E (MMAE), Monomethyl Auristatin F (MMAF), maytansine, maytansine derivatives, including the derivative of maytansine known as DM1 (also known as mertansine), or other chemotherapeutic agents to make an antibody drug conjugate (ADC). In several embodiments, various chemotherapeutic agents described herein can be conjugated to the provided antibodies to generate a conjugate.

In several embodiments, conjugates of an antibody or antigen binding fragment and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are available and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

In one example, the conjugate includes a monoclonal antibody that specifically binds EGFRvIII (or antigen binding fragment thereof), a non-reducible thioester linker and the maytansinoid toxin DM1; for example the conjugate can include the structure set forth as (wherein "mAb" refers to the monoclonal antibody or antigen binding fragment thereof):

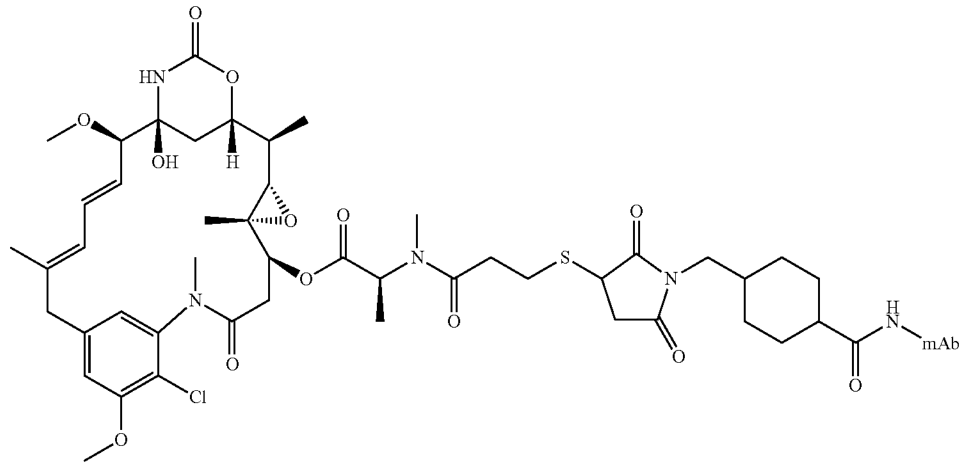

In some embodiments, the effector molecule is an auristatin, such as auristatin E (also known in the art as a derivative of dolastatin-10) or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other exemplary auristatins include AFP, MMAF, and MMAE. The synthesis and structure of exemplary auristatins are described in U.S. Patent Application Publication No. 2003/0083263; International Patent Publication No. WO 04/010957, International Patent Publication No. WO 02/088172, and U.S. Pat. Nos. 7,498,298, 6,884,869, 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein in its entirety. Additional description of antibody drug conjugates including the auristatin MMAE, and methods of making such conjugates, is provided in, e.g., U.S. Pub. Nos. 2011/0268751, 2008/0305044, 2007/0258987, each of which is incorporated by reference herein in its entirety). Auristatins have been shown to interfere with microtubule dynamics and nuclear and cellular division and have anticancer activity. Auristatins bind tubulin and can exert a cytotoxic or cytostatic effect on cells. There are a number of different assays, known in the art, which can be used for determining whether an auristatin or resultant conjugate exerts a cytostatic or cytotoxic effect on a desired cell line.

In one example, the conjugate includes a monoclonal antibody that specifically binds EGFRvIII (or antigen binding fragment thereof), a cleavable linker including a Valine-Citruline (Val-Cit) peptide cleavage site, a spacer, and the toxin MMAE; for example the conjugate can include the structure set forth as (wherein "mAb" refers to the monoclonal antibody or antigen binding fragment thereof):

I

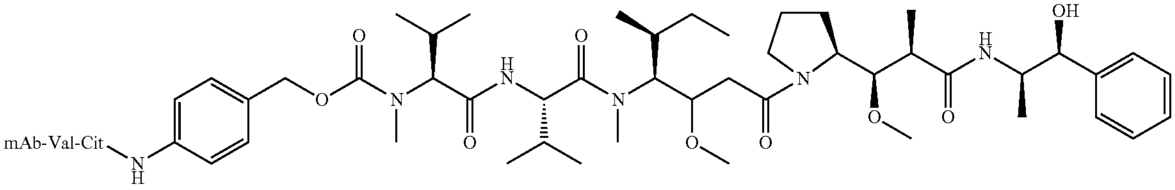

In one preferred embodiment, the conjugate may be

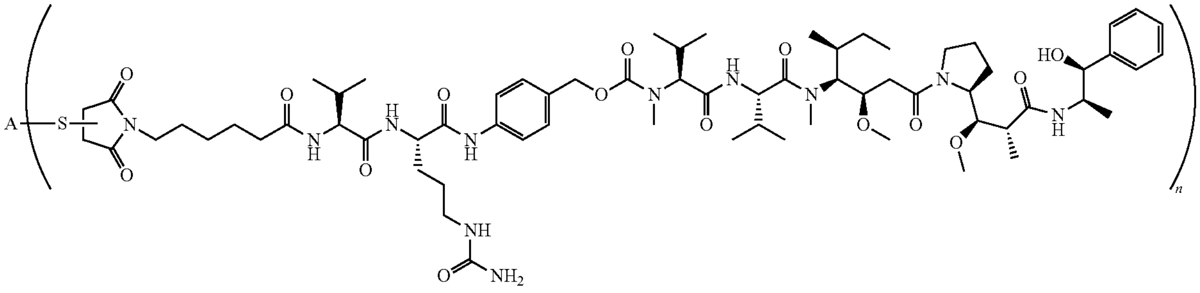

where n is an integer (such as an even integer) from 0 to 10 (such as 0 to 8, 0 to 4, 2 to 4, 2 to 8, 1 to 10, 1 to 8, or 1 to 4, or 2, 4, 6, or 8), A is a monoclonal antibody or antigen binding fragment thereof as disclosed herein, and S is a sulfur atom from the antibody. In one embodiment, preferably n is an even integer from 0 to 8, preferably from 0 to 4. The S moiety can be exposed by reduction or partial reduction of the inter-chain disulfides of the antibody (e.g., by treatment with a reducing agent such as DTT or TCEP).

In one non-limiting embodiment, the conjugate may be

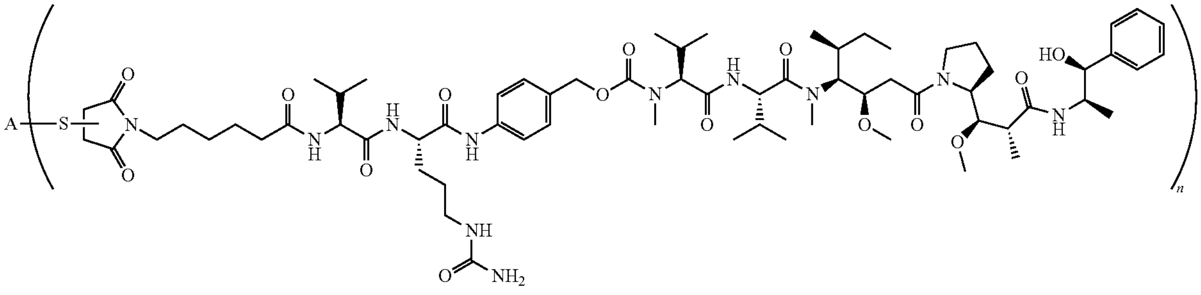

where n is 4, and A is a monoclonal antibody or antigen binding fragment thereof as disclosed herein.

Additional toxins can be employed with antibodies that specifically bind EGFRvIII, and antigen binding fragment of these antibodies. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, MO). Contemplated toxins also include variants of the toxins (see, for example, see, U.S. Pat. Nos. 5,079,163 and 4,689,401). In some embodiments, these conjugates are of use for the treatment of a carcinoma, for example a head and neck carcinoma, a breast carcinoma, or a bladder carcinoma.

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87,1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

In one embodiment, the toxin is *Pseudomonas* exotoxin (PE) (U.S. Pat. No. 5,602,095). As used herein, PE includes full-length native (naturally occurring) PE or a PE that has been modified. Such modifications can include, but are not limited to, elimination of domain Ia, various amino acid deletions in domains Tb, TI and ITT, single amino acid substitutions and the addition of one or more sequences at the carboxyl terminus (for example, see Siegall et al., J. Biol. Chem. 264:14256-14261, 1989). PE employed with the provided antibodies can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE25, PE40, PE38, and PE35. For additional description of PE and variants thereof, see for example, U.S. Pat. Nos. 4,892,827; 5,512,658; 5,602,095; 5,608,039; 5,821,238; and 5,854,044; PCT Publication No. WO 99/51643; Pai et al., Proc. Natl. Acad. Sci. USA, 88:3358-3362, 1991; Kondo et al., J. Biol. Chem., 263:9470-9475, 1988; Pastan et al., Biochim. Biophys. Acta, 1333:C1-C6, 1997.

Also contemplated herein are protease-resistant PE variants and PE variants with reduced immunogenicity, such as, but not limited to, PE-LR, PE-6X, PE-8X, PE-LR/6X and PE-LR/8X (see, for example, Weldon et al., Blood 113(16): 3792-3800, 2009; Onda et al., Proc. Natl. Acad. Sci. USA, 105(32):11311-11316, 2008; and PCT Publication Nos. WO 2007/016150, WO 2009/032954 and WO 2011/032022, which are herein incorporated by reference). The PE variant can be PE25, see Weldon et al., Blood 2009; 113:3792-3800, herein incorporated by reference.

In some examples, the PE is a variant that is resistant to lysosomal degradation, such as PE-LR (Weldon et al., Blood 113(16):3792-3800, 2009; PCT Publication No. WO 2009/032954). In other examples, the PE is a variant designated PE-LR/6X (PCT Publication No. WO 2011/032022). In other examples, the PE is a variant designated PE-LR/8M (PCT Publication No. WO 2011/032022).

A monoclonal antibody that specifically binds EGFRvIII (or antigen binding fragment thereof) can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody or antigen binding fragment may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

An antibody or antigen binding fragment can also be conjugated with a radiolabeled amino acid. The radiolabel may be used for both diagnostic and therapeutic purposes. For instance, the radiolabel may be used to detect EGFRvIII and EGFRvIII expressing cells by x-ray, emission spectra, or other diagnostic techniques. Further, the radiolabel may be used therapeutically as a toxin for treatment of tumors in a subject, for example for treatment of any tumor that expresses EGFRvIII, such as a carcinoma, for example a head and neck carcinoma, a breast carcinoma or a bladder carcinoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

An antibody or antigen binding fragment can also be derivatized with a chemical group such as polyethylene glycol (PEG), a methyl or ethyl group, or a carbohydrate group. These groups may be useful to improve the biological characteristics of the antibody or antigen binding fragment, such as to increase serum half-life or to increase tissue binding.

The average number of effector molecule or detectable marker moieties per antibody or antigen binding fragment in a conjugate can range, for example, from 1 to 20 moieties per antibody or antigen binding fragment. For some conjugates, the average number of effector molecule or detectable marker moieties per antibody or antigen binding fragment may be limited by the number of attachment sites on the antibody or antigen binding fragment. For example, where the attachment is a cysteine thiol, an antibody or antigen binding fragment may have only one or several cysteine thiol groups, or may have only one or several sufficiently reactive thiol groups through which a linker may be attached. In certain embodiments, the average number of effector molecule or detectable marker moieties per antibody or antigen binding fragment in a conjugate range from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. See, for example, U.S. Pat. No. 7,498,298, incorporated by reference herein in its entirety. The average number of effector molecule or detectable marker moieties per antibody or antigen binding fragment in preparations of conjugates may be characterized by conventional means such as mass spectroscopy and, ELISA assay. The loading (for example, effector molecule/antibody ratio) of an conjugate may be controlled in different ways, for example, by: (i) limiting the molar excess of effector molecule-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number or position of linker-effector molecule attachments (such as thioMab or thioFab prepared as disclosed in WO2006/03448, incorporated by reference herein in its entirety.

C. Chimeric Antigen Receptors (CARs)

Also disclosed herein are chimeric antigen receptor (CARs) that are artificially constructed chimeric proteins including an extracellular antigen binding domain (e.g., single chain variable fragment (scFv)) that specifically binds to EGFRvIII, linked to a transmembrane domain, linked to one or more intracellular T-cell signaling domains. Characteristics of the disclosed CARs include their ability to redirect T-cell specificity and reactivity towards EGFRVIII expressing cells in a non-MHC-restricted manner. The non-MHC-restricted EGFRVIII recognition gives T cells expressing a disclosed CAR the ability to recognize antigen independent of antigen processing.

The intracellular T cell signaling domains can include, for example, a T cell receptor signaling domain, a T cell costimulatory signaling domain, or both. The T cell receptor signaling domain refers to a portion of the CAR including the intracellular domain of a T cell receptor, such as the intracellular portion of the CD3 zeta protein. The costimulatory signaling domain refers to a portion of the CAR including the intracellular domain of a costimulatory molecule, which is a cell surface molecule other than an antigen receptor or their ligands that are required for an efficient response of lymphocytes to antigen.

1. Extracellular Region

Several embodiments provide a CAR including an antigen binding domain that specifically binds to EGFRVIII as disclosed herein. For example, the antigen binding domain can be a scFv including the heavy chain variable region and the light chain variable region of any of the antibodies or antigen binding fragments thereof disclosed above.

In some embodiment, the antigen binding domain can include a heavy chain variable region and a light chain variable region including the HCDR1, HCDR2, and HCDR3, and LCDR1, LCDR2, and LCDR3 of the of the heavy and light chain variable regions, respectively, of one of the 40H3, 1D9, 3D10, 4A4, 9G3, 11E11, or 11G3 antibodies (see above). For example, the antigen binding domain can include the HCDR1, HCDR2, and HCDR3, and LCDR1, LCDR2, and LCDR3 of SEQ ID NOs: 1 and 2, SEQ ID NOs: 11 and 12, SEQ ID NOs: 13 and 14, or SEQ ID NOs: 15 and 16. The antigen binding domain can include the HCDR1, HCDR2, and HCDR3, and LCDR1, LCDR2, and LCDR3 of SEQ ID NOs: 17 and 12, SEQ ID NOs: 26 and 12, SEQ ID NOs: 29 and 30, SEQ ID NOs: 39 and 40, SEQ ID NOs: 43 and 44, or SEQ ID NOs: 53 and 54. Any of the antibodies or antigen binding fragments disclosed herein can be used in the CAR. In one embodiment, the antibody or antigen binding fragment is humanized.

In several embodiments, the antigen binding domain can be a scFv. In some embodiments, the scFv includes a heavy chain variable region and a light chain variable region joined by a peptide linker, such as a linker including the amino acid sequence set forth as GGGGSGGGGSGGGGS (SEQ ID NO: 59).

The CAR can include a signal peptide sequence, e.g., N-terminal to the antigen binding domain. The signal peptide sequence may comprise any suitable signal peptide sequence. In an embodiment, the signal peptide sequence is a human granulocyte-macrophage colony-stimulating factor (GM-CSF) receptor sequence, such as an amino acid sequence including or consisting of LLVTSLLLCEL-PHPAFLLIPDT SEQ ID NO: 60. While the signal peptide sequence may facilitate expression of the CAR on the surface of the cell, the presence of the signal peptide sequence in an expressed CAR is not necessary in order for the CAR to function. Upon expression of the CAR on the cell surface, the signal peptide sequence may be cleaved off of the CAR. Accordingly, in some embodiments, the CAR lacks a signal peptide sequence.

Between the antigen binding domain and the transmembrane domain of the CAR, there may be a spacer domain, which includes a polypeptide sequence. The spacer domain may comprise up to 300 amino acids, preferably 10 to 100 amino acids and most preferably 25 to 50 amino acids. In some embodiments, the spacer domain can include an immunoglobulin domain, such as a human immunoglobulin sequence. In an embodiment, the immunoglobulin domain comprises an immunoglobulin CH2 and CH3 immunoglobulin G (IgG1) domain sequence (CH2CH3). In this regard, the spacer domain can include an immunoglobulin domain comprising or consisting of the amino acid sequence set forth as SEQ ID NO: 61: EPKSCDKTHTCPPCPA-PELLGGPSVFLFPPKPKDTLMISRTPE-VTCVVVDVSHEDPEVKFNWYVDGV EVHNAKTKPREEQYN-STYRVVSVLTVLHQDWLNGKEYKCKVSNKALPA-PIEKTISKAKGQPREPQ VYTLPPSRDELTKNQVSLT-CLVKGFYPSDIAVEWESNGQPENNYKTTPPVLDSDGSFF-LYSKLTVDK SRWQQGNVFSCSVMHEALHNHYTQKSLSL-SPGKKDPK Without being bound to a particular theory, it is believed that the CH2CH3 domain extends the antigen binding domain of the CAR away from the membrane of CAR-expressing cells and may more accurately mimic the size and domain structure of a native TCR.

2. Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used.

The transmembrane domain may be derived either from a natural or from a synthetic source. Where the source is natural, the domain may be derived from any membrane-bound or transmembrane protein. Exemplary transmembrane domains for use in the disclosed CARs can include at least the transmembrane region(s) of) the alpha, beta or zeta chain of the T-cell receptor, CD28, CD3 epsilon, CD45, CD4, CD5, CDS, CD9, CD 16, CD22, CD33, CD37, CD64, CD80, CD86, CD 134, CD137, CD154. Alternatively the transmembrane domain may be synthetic, in which case it will comprise predominantly hydrophobic residues such as leucine and valine. In several embodiments, a triplet of phenylalanine, tryptophan and valine will be found at each end of a synthetic transmembrane domain.

Optionally, a short oligo- or polypeptide linker, preferably between 2 and 10 amino acids in length may form the linkage between the transmembrane domain and the intracellular T cell signaling domain and/or T cell costimulatory domain of the CAR. A exemplary linker sequence includes one or more glycine-serine doublets.

In some embodiments, the transmembrane domain comprises the transmembrane domain of a T cell receptor, such as a CD8 transmembrane domain. Thus, the CAR can include a CD8 transmembrane domain including or consisting of SEQ ID NO: 62: TTTPAPRPPTPAPTIA-SQPLSLRPEACRPAAGGAVHTRGLDFACDIYI-WAPLAGTCGVLLLSLVITLY C In another embodiment, the transmembrane domain comprises the transmembrane domain of a T cell costimulatory molecule, such as CD137 or CD28. Thus, the CAR can include a CD28 transmembrane domain including or consisting of SEQ ID NO: 63: IEVMYPPPYLD-NEKSNGTIIHVKGKHLCPSPLFPGPSKPFWVLVVVGGV-LACYSLLVTVAFIIFWVR 3. Intracellular Region The intracellular region of the CAR includes one or more intracellular T cell signaling domains responsible for activation of at least one of the normal effector functions of a T cell in which the CAR is expressed or placed in. Exemplary T cell signaling domains are provided herein, and are known to the person of ordinary skill in the art.

While an entire intracellular T cell signaling domain can be employed in a CAR, in many cases it is not necessary to use the entire chain. To the extent that a truncated portion of the intracellular T cell signaling domain is used, such truncated portion may be used in place of the intact chain as long as it transduces the relevant T cell effector function signal.

Examples of intracellular T cell signaling domains for use in the CAR include the cytoplasmic sequences of the T cell receptor (TCR) and co-stimulatory molecules that act in concert to initiate signal transduction following antigen receptor engagement, as well as any derivative or variant of these sequences and any synthetic sequence that has the same functional capability.

T cell receptor signaling domains regulate primary activation of the T cell receptor complex either in a stimulatory way, or in an inhibitory way. The disclosed CARs can include primary cytoplasmic signaling sequences that act in a stimulatory manner, which may contain signaling motifs that are known as immunoreceptor tyrosine-based activation motifs or ITAMs. Examples of ITAM containing primary cytoplasmic signaling sequences that can be included in a disclosed CAR include those from CD3 zeta, FcR gamma, FcR beta, CD3 gamma, CD3 delta, CD3 epsilon, CDS, CD22, CD79a, CD79b, and CD66d proteins. In several embodiments, the cytoplasmic signaling molecule in the CAR includes an intracellular T cell signaling domain from CD3 zeta.

The intracellular region of the CAR can include the ITAM containing primary cytoplasmic signaling domain (such as CD3-zeta) by itself or combined with any other desired cytoplasmic domain(s) useful in the context of a CAR. For example, the cytoplasmic domain of the CAR can include a CD3 zeta chain portion and an intracellular costimulatory signaling domain. The costimulatory signaling domain refers to a portion of the CAR including the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40 (CD134), CD30, CD40, PD-1, ICOS, lymphocyte function-associated antigen 1 (LFA-1), CD2, CD7, LIGHT, NKG2C, and B7-H3. An additional example of a signaling domain that can be included in a disclosed CARs is a Tumor necrosis factor receptor superfamily member 18 (TNFRSF18; also known as glucocorticoid-induced TNFR-related protein, GITR) signaling domain.

In some embodiments, the CAR can include a CD3 zeta signaling domain, a CD8 signaling domain, a CD28 signaling domain, a CD137 signaling domain or a combination of two or more thereof. In one embodiment, the cytoplasmic domain includes the signaling domain of CD3-zeta and the signaling domain of CD28. In another embodiment, the cytoplasmic domain includes the signaling domain of CD3 zeta and the signaling domain of CD137. In yet another embodiment, the cytoplasmic domain includes the signaling domain of CD3-zeta and the signaling domain of CD28 and CD137. The order of the one or more T cell signaling domains on the CAR can be varied as needed by the person of ordinary skill in the art. Exemplary amino acid sequences for such T cell signaling domains are provided. For example, the CD3 zeta signaling domain can include or consist of the amino acid sequence set forth as SEQ ID NO: 64 (RVKFSR-SADAPAYQQGQNQLYNELNLGRREEYDVLDKRR-GRDPEMGGKPRRKNPQEGLYNELQ KDKMAEAYSEI-GMKGERRRGKGHDGLYQGLSTATKDTYDALHMQALPPR), the CD8 signaling domain can include or consist of the amino acid sequence set forth as SEQ ID NO: 65 (FVPVFL-PAKPTTTPAPRPPTPAPTIASQPLSLRPEACR-PAAGGAVHTRGLDFACDIYIWAPLAGTCG VLLLSLVITLYCNHRNR), the CD28 signaling domain can include or consist of the amino acid sequence set forth as SEQ ID NO: 66 (SKRSRLLHSDYMNMTPRRPGP-TRKHYQPYAPPRDFAAYRS), the CD137 signaling domain can include or consist of the amino acid sequences set forth as SEQ ID NO: 67 (KRGRKKLLY-IFKQPFMRPVQTTQEEDGCSCRFPEEEEGGCEL) or SEQ ID NO: 68 (RFSVVKRGRKKLLY-IFKQPFMRPVQTTQEEDGCSCRFPEEEEGGCEL).

The cytoplasmic signaling sequences within the cytoplasmic signaling portion of the CAR of the invention may be linked to each other in a random or specified order. Optionally, a short polypeptide linker, preferably between 2 and 10 amino acids in length may form the linkage. A glycine-serine doublet provides a particularly suitable linker. Further, between the signaling domain and the transmembrane domain of the CAR, there may be a spacer domain, which includes a polypeptide sequence. The spacer domain may comprise up to 300 amino acids, preferably 10 to 100 amino acids and most preferably 25 to 50 amino acids.

4. Additional Description of CARs

Also provided are functional portions of the CARs described herein. The term "functional portion" when used in reference to a CAR refers to any part or fragment of the CAR, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The CAR or functional portion thereof, can include additional amino acids at the amino or carboxy terminus, or at both termini, which additional amino acids are not found in the amino acid sequence of the parent CAR. Desirably, the additional amino acids do not interfere with the biological function of the CAR or functional portion, e.g., recognize target cells, detect cancer, treat or prevent cancer, etc. More desirably, the additional amino acids enhance the biological activity, as compared to the biological activity of the parent CAR.

Also provided are functional variants of the CARs described herein, which have substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, about 50%, about 75%, about 80%, about 85%, about 90%, about 91%, about 92%, about 93%, about 94%, about 95%, about 96%), about 97%, about 98%, about 99% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, a-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, oc-aminocycloheptane carboxylic acid, -(2-amino-2-norbornane)-carboxylic acid, γ-diaminobutyric acid, α,β-diaminopropionic acid, homophenylalanine, and α-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

Methods of generating chimeric antigen receptors, T cells including such receptors, and their use (e.g., for treatment of cancer) are known in the art and further described herein (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., *Trends Biotechnol.,* 29:550-557, 2011; Grupp et al., N Engl J Med., 368:1509-1518, 2013; Han et al., J. Hematol Oncol., 6:47, 2013; PCT Pub. WO2012/079000, WO2013/126726; and U.S. Pub. 2012/0213783, each of which is incorporated by reference herein in its entirety.) For example, a nucleic acid molecule encoding a disclosed chimeric antigen binding receptor can be included in an expression vector (such as a lentiviral vector) for expression in a host cell, such as a T cell, to make the disclosed CAR. In some embodiments, methods of using the chimeric antigen receptor include isolating T cells from a subject, transforming the T cells with an expression vector (such as a lentiviral vector) encoding the chimeric antigen receptor, and administering the engineered T cells expressing the chimeric antigen receptor to the subject for treatment, for example for treatment of a tumor in the subject.

D. Polynucleotides and Expression

Nucleic acids encoding the amino acid sequences of antibodies, antibody binding fragments, conjugates, and CARs that specifically bind EGFRvIII are provided. Nucleic acids encoding these molecules can readily be produced by one of skill in the art, using the amino acid sequences provided herein (such as the CDR sequences, heavy chain and light chain sequences), sequences available in the art (such as framework sequences), and the genetic code. One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence.

Nucleic acid sequences encoding the of antibodies, antibody binding fragments, conjugates, and CARs that specifically bind EGFRvIII can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids can be prepared by cloning techniques. Examples of appropriate cloning and sequencing techniques, and instructions sufficient to direct persons of skill through many cloning exercises are known (see, e.g, Sambrook et al. (Molecular Cloning: A Laboratory Manual, $4^{th}$ ed, Cold Spring Harbor, New York, 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, MO), R&D Systems (Minneapolis, MN), Pharmacia Amersham (Piscataway, NJ), CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersburg, MD), Fluka Chemica-Biochemika Analytika (Fluka Chemie AG, Buchs, Switzerland), Invitrogen (Carlsbad, CA), and Applied Biosystems (Foster City, CA), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In some embodiments, the nucleic acid molecule encodes a CAR as provided herein for expression in a T cell to generate a chimeric antigen receptor T cell. The nucleic acid molecule encoding the chimeric antigen binding receptor can be included in a vector (such as a lentiviral vector) for expression in a host cell, such as a T cell. Exemplary cells include a T cell a Natural Killer (NK) cell, a cytotoxic T lymphocyte (CTL), and a regulatory T cell. Methods of generating nucleic acid molecules encoding chimeric antigen receptors and T cells including such receptors are known in the art (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., *Trends Biotechnol.,* 29:550-557, 2011; Grupp et al., N Engl J Med., 368:1509-1518, 2013; Han et al., J. Hematol Oncol., 6:47, 2013; PCT Pub. WO2012/079000, WO2013/126726; and U.S. Pub. 2012/0213783, each of which is incorporated by reference herein in its entirety.)

The nucleic acid molecules can be expressed in a recombinantly engineered cell such as bacteria, plant, yeast, insect and mammalian cells. The antibodies, antigen binding fragments, and conjugates can be expressed as individual $V_H$ and/or $V_L$ chain (linked to an effector molecule or detectable marker as needed), or can be expressed as a fusion protein. Methods of expressing and purifying antibodies and antigen binding fragments are known and further described herein (see, e.g., Al-Rubeai (ed), *Antibody Expression and Production*, Springer Press, 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_L$ and $V_H$ domains joined by the flexible linker (see, e.g., Bird et al., *Science* 242:423-426, 1988; Huston et al., *Proc. Natl. Acad. Sci. USA* 85:5879-5883, 1988; McCafferty et al., *Nature* 348:552-554, 1990; Kontermann and Dubel (Ed), Antibody Engineering, Vols. 1-2, $2^{nd}$ Ed., Springer Press, 2010; Harlow and Lane, *Antibodies: A Laboratory Manual,* $2^{nd}$, Cold Spring Harbor Laboratory, New York, 2013). Optionally, a cleavage site can be included in a linker, such as a furin cleavage site.

The nucleic acid encoding a $V_H$ and/or the $V_L$ optionally can encode an Fc domain (immunoadhesin). The Fc domain can be an IgA, IgM or IgG Fc domain. The Fc domain can be an optimized Fc domain, as described in U.S. Published Patent Application No. 2010/093979, incorporated herein by reference. In one example, the immunoadhesin is an $IgG_1$ Fc.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to EGFRVIII and another antigen, such as, but not limited to, CD3. The encoded $V_H$ and $V_L$ optionally can include a furin cleavage site between the $V_H$ and $V_L$ domains.

Those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the antibodies, antibody binding fragments, conjugates, and CARs can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

Polynucleotide sequences encoding the antibody or antigen binding fragment or conjugate thereof, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

The polynucleotide sequences encoding the antibody, or antigen binding fragment or conjugate thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or antigen binding fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

For purposes of producing a recombinant CAR, the host cell may be a mammalian cell. The host cell may be a human cell. In some embodiments, the host cell may be a peripheral blood lymphocyte (PBL) or a peripheral blood mononuclear cell (PBMC), or a T cell. The T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells (e.g., cytotoxic T cells), tumor infiltrating cells, memory T cells, naive T cells, and the like. The T cell may be a $CD8^+$ T cell or a $CD4^+$ T cell.

Also provided is a population of cells including at least one host cell described herein. The population of cells can be a heterogeneous population including the host cell including any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) including the recombinant expression vector. The population also can be a clonal population of cells, in which all cells of the population are clones of a single host cell including a recombinant expression vector, such that all cells of the population comprise the recombinant expression vector. In one embodiment of the invention, the population of cells is a clonal population including host cells including a recombinant expression vector as described herein Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the antibodies, antigen binding fragments, and conjugates can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The antibodies, antigen binding fragment, and conjugates need not be 100% pure. Once purified, partially or to homogeneity as desired, if to be used therapeutically, the polypeptides should be substantially free of endotoxin.

Methods for expression of the antibodies, antigen binding fragments, and conjugates, and/or refolding to an appropriate active form, from mammalian cells, and bacteria such as *E. coli* have been described and are well-known and are applicable to the antibodies disclosed herein. See, e.g., Harlow and Lane, *Antibodies: A Laboratory Manual, 2nd*, Cold Spring Harbor Laboratory, New York, 2013, Simpson ed., Basic methods in Protein Purification and Analysis: A laboratory Manual, Cold Harbor Press, 2008, and Ward et al., *Nature* 341:544, 1989.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, and especially as described by Buchner et al., supra.

In addition to recombinant methods, the antibodies, antigen binding fragments, and/or conjugates can also be constructed in whole or in part using standard peptide synthesis. Solid phase synthesis of the polypeptides can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis,* 2nd ed., *Pierce Chem. Co*., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art.

E. Methods of Detection

Methods are provided for detecting the presence of a cell that expresses EGFRvIII in a subject, such as a tumor cells that expresses EGFRvIII. In some embodiments, the methods include contacting a cell from a subject with one or more of the antibodies that specifically bind EGFRvIII or conjugate thereof to form an immune complex. The presence (or absence) of the immune complex is then detected. The presence of the immune complex indicates the presence of a cell that expresses EGFRvIII in the subject. The detection methods can involve in vivo detection or in vitro detection of the immune complex. In several embodiments, detection of a cell that expresses EGFRvIII includes detecting cell-surface expression of EGFRvIII on the tumor cell. In several embodiments of the provided methods, detecting a cell that expresses EGFRvIII in a subject detects a tumor. In several non-limiting examples, the tumor is a carcinoma, such as a head and neck carcinoma, a breast carcinoma, or a bladder carcinoma. In some examples, the method can also detect a tumor cell that overexpresses EGFRvIII.

A variety of formats are of use for detecting a cell that expresses EGFRvIII, for example, a tumor cell that expresses EGFRvIII. In some embodiments, a subject is selected who has, is suspected of having, or is at risk of developing, a tumor, for example, a carcinoma. For example, the subject has, is suspected of having, or is at risk of developing head and neck carcinoma, breast carcinoma, or bladder carcinoma. In some examples the subject has, is suspected of having, or is at risk of developing, head and neck carcinoma, breast carcinoma, or bladder carcinoma. Thus, the presence of a cell expressing EGFRvIII can be detected in these subjects.

On some embodiments, R300 is required for the antibody or antigen binding fragment binds to the $EGRF_{287-302}$ loop, and the method can also detect overexpression of EGFR. Overexpression can be measured, such that any cell with more than about 50.00 receptors, more than about 60.00 receptors, more than about 70.00 receptors, more than about 80.00 receptors, more than about 90.00 receptors, or more than about more than about 100.00 receptors is detected. For example, such methods include contacting a tumor cell in a biological sample from the subject with one or more of the conjugates or antibodies provided herein or an antigen binding fragment thereof to form an immune complex. The presence (or absence) of the immune complex is then detected and/or quantified. The presence (or amount) of the immune complex on the cell from the subject indicates the presence of a tumor cell that overexpresses EGFR in the subject.

In one embodiment, a sample is obtained from a subject, and the presence of a tumor cell that expresses EGFRvIII is assessed in vitro. For example, such methods include contacting a tumor cell in a biological sample from the subject with one or more of the conjugates or antibodies provided herein that specifically bind EGFRvIII or an antigen binding fragment thereof to form an immune complex. The presence (or absence) of the immune complex is then detected. The presence of the immune complex on the cell from the subject indicates the presence of a tumor cell that expresses EGFRvIII in the subject. For example, an increase in the presence of the immune complex in the sample as compared to formation of the immune complex in a control sample indicates the presence of a tumor cell that expresses EGFRvIII in the subject. In some embodiments, a control can be utilized.

A biological sample is typically obtained from a mammalian subject of interest, such as human. The sample can be any sample, including, but not limited to, tissue from biopsies, autopsies and pathology specimens. Biological samples also include sections of tissues, for example, frozen sections taken for histological purposes.

In some examples of the disclosed methods, the antibody or antigen binding fragment is conjugated to a detectable marker. In some examples, the methods further include contacting a second antibody that specifically binds the EGFRvIII specific antibody, antigen binding fragment thereof, or a conjugate including these molecules, for a sufficient amount of time to form an immune complex and detecting this immune complex. An increase in the presence of this immune complex in a biological sample from a selected subject (as described above) compared to the presence of the immune complex in a control sample or other standard detects the presence of an endothelial cell that expresses EGFRvIII in the biological sample. In some examples, the second antibody is conjugated to a detectable marker.

Suitable detectable markers for the antibody or secondary antibody are described and known to the skilled artisan. For example, various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$.

The antibodies that specifically bind EGFRvIII and conjugates thereof can be used in immunohistochemical assays. These assays are well known to one of skill in the art (see Harlow & Lane, *Antibodies, A Laboratory Manual,* $2^{nd}$ ed., Cold Spring Harbor Publications, New York (2013), for a description of immunoassay formats The antibodies disclosed herein can also be used to detect tumor cells that express EGFRvIII in vivo. In some example, in vivo detection of diagnoses the presence of the tumor in the subject. Thus, methods are disclosed for detecting pathological conditions in a subject, such as a tumor, such as a carcinoma; for example, head and neck carcinoma, breast carcinoma, or bladder carcinoma. In one embodiment, an effective amount of an antibody that specifically binds to EGFRvIII (or antigen binding fragment thereof) or a conjugate thereof is administered to the subject for a sufficient amount of time for the antibody or antigen binding fragment to form an immune complex, which can then be detected. Detection of the immune complex in the subject determines the presence of a tumor cell that expresses EGFRvIII. In one specific, non-limiting example detection of an immune complex is performed by immunoscintography. Other specific, non-limiting examples of immune complex detection include radiolocalization, radioimaging, magnetic resonance imaging (such as using a biotinylated antibody and avidin-iron oxide), positron emission tomography (such as using an $m^1$ indium-labeled monoclonal antibody) or fluorescence imaging (such as using luciferase or green fluorescent protein labeled antibodies). See Paty et al., *Transplantation.,* 77:1133-1137, 2004, herein incorporated by reference. In several examples, the disclosed method detects, for example, head and neck carcinoma, breast carcinoma, or bladder carcinoma.

In the setting of magnetic resonance imaging, contrast agent detection can be greatly impacted by magnetic resonance scanner field strength. Increased field strengths provide improvements by orders of magnitude in the ability to detect contrast agents (Hu et al., *Ann. Rev. Biomed. Eng.,* 6:157-184, 2004; Wedeking et al., *Magn. Reson. Imaging.,* 17:569-575, 1999). For example, the limit of detection of gadolinium at 2 tesla (T) is ~30 μM. At 4T the limit of detection is reduced to ~1 μM. With newly available 7 to 12T scanners one would expect to detect low ($10^{-100}$) nM concentrations of this contrast agent. Similar sensitivity can also be identified using contrast agents such as iron oxide. Once detected the test results can be used to assist in or guide surgical or other excision of a tumor.

In one embodiment, an effective amount of an antibody or antigen binding fragment that specifically binds to EGFRvIII or a conjugate thereof is administered to a subject having a tumor following anti-cancer treatment. After a sufficient amount of time has elapsed to allow for the administered antibody or antigen binding fragment or conjugate to form an immune complex with EGFRvIII on a tumor cell, the immune complex is detected. For example, an antibody that specifically binds to EGFRvIII or conjugate thereof can be administered to a subject prior to, or following, treatment of a tumor. The tumor can be (but is not limited to) a carcinoma, such as a head and neck carcinoma, a breast carcinoma or a bladder carcinoma. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Methods of Treatment

A therapeutically effective amount of an antibody or antigen binding fragment that specifically binds EGFRvIII or conjugate thereof or CAR T cell expressing an antigen binding fragment that specifically binds EGFRvIII can be administered to a subject to treat a tumor that expresses EGFRvIII, for example a carcinoma, such as a head and neck carcinoma, a breast carcinoma or a bladder carcinoma. In some embodiments, administration of a therapeutically effective amount of an antibody or antigen binding fragment that specifically binds EGFRvIII or conjugate thereof or CAR T cell expressing an antigen binding fragment that specifically binds EGFRvIII decreases a sign or symptom of a tumor that expresses EGFRvIII, such as a carcinoma, for example, a head and neck carcinoma, breast carcinoma, or bladder carcinoma. Thus, a subject can be selected for treatment that has, is suspected of having or is at risk of developing the tumor that expresses EGFRvIII. A therapeutically effective amount of the nucleic acid molecules and vectors disclosed herein are also of use.

In other embodiments, the tumor can overexpress EGFR, and/or express misfolded EGFR. In some embodiments a subject is selected that has a tumor that overexpresses EGFR and/or expresses misfolded EGFR. The compositions disclosed herein are of use for treating these tumors in a subject.

In further embodiments, a therapeutically effective amount of an antibody or antigen binding fragment, as disclosed herein, can also be used in method of inhibiting a tumor over-expressing EGFR in a subject The method includes administering an effective amount of the antibody, antigen binding fragment, nucleic acid molecule, vector, T cell or pharmaceutical composition to the subject having the tumor overexpressing EGFR. In some non-limiting examples, the antibody or antigen binding fragment comprises the $V_H$ comprising the HCDR1, the HCDR2, and the HCDR3 of SEQ ID NO: 1, and the $V_H$ comprising the LCDR1, the LCDR2, and the LCDR3 of SEQ ID NO: 2. Nucleic acid molecules, vector, and CAR T cells including these antigen binding fragments are also of use. The tumor can be a carcinoma, for example, a head and neck carcinoma, breast carcinoma, or bladder carcinoma. Thus, a subject can be selected for treatment that has, is suspected of having or is at risk of developing the tumor that overexpresses EGFR.

In some examples, the antibodies, antigen binding fragments, CAR T cells, compositions and conjugates disclosed herein can be administered to a subject to slow or inhibit the growth or metastasis of a tumor, reduce tumor volume or reduce metastasis. In these applications, a therapeutically effective amount of an antibody or antigen binding fragment that specifically binds EGFRvIII or a conjugate or CAR T cells or composition is administered to a subject in an amount and under conditions sufficient to form an immune complex with EGFRvIII, thereby slowing or inhibiting the growth or the metastasis of a tumor, to reduce tumor volume, or to inhibit a sign or a symptom of a cancer. Examples of suitable subjects include those diagnosed with or suspecting of having a tumor that expresses EGFRvIII, for example subjects having a carcinoma, such as a breast carcinoma, lung carcinoma, colorectal carcinoma or melanoma.

The therapeutically effective amount will depend upon the severity of the disease and the general state of the patient's health. A therapeutically effective amount is that which provides either subjective relief of a symptom(s) or an objectively identifiable improvement as noted by the clinician or other qualified observer. In one embodiment, a therapeutically effective amount is the amount necessary to inhibit tumor growth (such as growth of a carcinoma, such as a head and neck carcinoma, breast carcinoma, bladder carcinoma), inhibit metastasis, reduce tumor volume, or the amount that is effective at reducing a sign or a symptom of the tumor. The therapeutically effective amount of the agents administered can vary depending upon the desired effects and the subject to be treated. In some examples, therapeutic amounts are amounts which eliminate or reduce the patient's tumor burden, or which prevent or reduce the proliferation of metastatic cells, or reduce a symptom of the tumor.

Subjects that can benefit from the disclosed methods include human and veterinary subjects. Subjects can be screened prior to initiating the disclosed therapies, for example to determine whether the subject has a tumor. The presence of a tumor that expresses EGFRvIII indicates that the can be treated using the methods provided herein.

Any method of administration can be used for the disclosed antibodies, antigen binding fragments, conjugates, CAR T cells, compositions and additional agents, including local and systemic administration. For example, topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the conjugates, antibodies, antigen binding fragments, CAR T cells, nucleic acid molecules, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment (or conjugate thereof) may be beneficial.

The compositions that include an antibody or antigen binding fragment or conjugate thereof or CAR T cells can be formulated in unit dosage form suitable for individual administration of precise dosages. In addition, the compositions may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies, conjugates, compositions or additional agents can range from about 0.01 to about 30 mg/kg, such as from about 0.1 to about 10 mg/kg. In some examples, the dosage is at least about 0.1 mg/kg, at least about 0.2 mg/kg, at least about 0.3 mg/kg, at least about 0.4 mg/kg, at least about 0.5 mg/kg, at least about 1 mg/kg, at least about 4 mg/kg, at least about 3 mg/kg, at least about 5 mg/kg, at least about 6 mg/kg, at least about 7 mg/kg, at least about 8 mg/kg is at least about 9 mg/kg, at least about 10 mg/kg, at least about 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, at least about 20 mg/kg, at least about 21 mg/kg, at least about 22 mg/kg, at least about 23 mg/kg, at least about 24 mg/kg at least about 25 mg/kg, at least about 26 mg/kg, at least about 27 mg/kg, at least about 28 mg/kg, at least about 29 mg/kg, or at least about 30 mg/kg.

In particular examples, the subject is administered a therapeutic composition that includes one or more of the conjugates, antibodies, compositions, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, a disclosed therapeutic agent is administered may be administered intravenously, subcutaneously or by another mode daily or multiple times per week for a period of time, followed by a period of no treatment, then the cycle is repeated. In some embodiments, the initial period of treatment (e.g., administration of the therapeutic agent daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the therapeutic agent is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

Administration of the antibodies, antigen binding fragments, conjugates, CAR T cells, or compositions can be accompanied by administration of other anti-cancer or anti-angiogenesis agents or therapeutic treatments (such as surgical resection of a tumor or radiation therapy). For example, prior to, during, or following administration of a therapeutic amount of the antibodies or conjugates, the subject can receive one or more additional therapies. In one example, the subject receives one or more treatments to remove or reduce the tumor prior to administration of a therapeutic amount of one or more agents for treatment of the tumor. For example, the additional agent may include, but is not limited to, a chemotherapeutic agent, an anti-angiogenic agent, or a combination thereof. In another example, at least part of the tumor is surgically or otherwise excised or reduced in size or volume prior to administering the therapeutically effective amount of the antibody or antigen binding fragment or conjugate.

Particular examples of additional therapeutic agents that can be used include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the antibodies, conjugates disclosed herein. Methods and therapeutic dosages of such agents are known to those skilled in the art, and can be determined by a skilled clinician. In one example the chemotherapeutic agent includes 5-FU or IRT or both.

Microtubule binding agent refers to an agent that interacts with tubulin to stabilize or destabilize microtubule formation thereby inhibiting cell division. Examples of microtubule binding agents that can be used in conjunction with the disclosed therapy include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264, can be used.

Suitable DNA and RNA transcription regulators, including, without limitation, actinomycin D, daunorubicin, doxorubicin and derivatives and analogs thereof also are suitable for use in combination with the disclosed therapies. DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use as therapeutic agents include, without limitation, methotrexate, 5-fluoro-5'-deoxyuridine, 5-FU and analogs thereof. Examples of suitable enzyme inhibitors include, without limitation, camptothecin, etoposide, formestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof.

Examples of the commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, IRT (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Thus, non-limiting examples of chemotherapeutic agents for use in combination with the disclosed EGFRvIII specific antibodies, antigen binding fragments, or conjugates thereof, CAT T cells, and nucleic acid molecules include chemotherapeutic agents such as erlotinib (TARCEVA®, Genentech/OSI Pharm.), bortezomib (VELCADE®, Millenium Pharm.), fulvestrant (FASLODEX®, AstraZeneca), sutent (SU11248, Pfizer), letrozole (FEMARA®, Novartis), imatinib mesylate (GLEEVEC®, Novartis), PTK787/ZK 222584 (Novartis), oxaliplatin (Eloxatin®, Sanofi), 5-FU (5-fluorouracil), leucovorin, Rapamycin (Sirolimus, RAPAMUNE®, Wyeth), lapatinib (TYKERB®, GSK572016, GlaxoSmithKline), lonafarnib (SCH 66336), sorafenib (BAY43-9006, Bayer Labs.), and gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; antifolate antineoplastic such as pemetrexed (ALIMTA® Eli Lilly), aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics, calicheamicin, calicheamicin gamma1I and calicheamicin omegaI1; dynemicin, including dynemicin A; bisphosphonates, such as clodronate; an esperamicin; as well as neocarzinostatin chromophore and related chromoprotein enediyne antibiotic chromophores, aclacinomysins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, for example, paclitaxel (TAXOL®, Bristol-Myers Squibb Oncology, Princeton, N.J.), ABRAXANE™ Cremophor-free, albumin, nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluorometlhylornithine (DMFO); retinoids such as retinoic acid; capecitabine; and pharmaceutically acceptable salts, acids or derivatives of any of the above.

Non-limiting examples of anti-angiogenic agents include molecules, such as proteins, enzymes, polysaccharides, oligonucleotides, DNA, RNA, and recombinant vectors, and small molecules that function to reduce or even inhibit blood vessel growth. Examples of suitable angiogenesis inhibitors include, without limitation, angiostatin K1-3, staurosporine, genistein, fumagillin, medroxyprogesterone, suramin, interferon-alpha, metalloproteinase inhibitors, platelet factor 4, somatostatin, thromobospondin, endostatin, thalidomide, and derivatives and analogs thereof. For example, in some embodiments the anti-angiogenesis agent is an antibody that specifically binds to VEGF (for example, AVASTIN®, Roche) or a VEGF receptor (for example, a VEGFR2 antibody). In one example the anti-angiogenic agent includes a VEGFR2 antibody, or DMXAA (also known as Vadimezan or ASA404; available commercially, for example, from Sigma Corp., St. Louis, MO) or both. Exemplary kinase inhibitors include GLEEVAC®, IRESSA®, and TARCEVA® that prevent phosphorylation and activation of growth factors. Antibodies that can be used include HERCEPTIN® and AVASTIN® that block growth factors and the angiogenic pathway.

In some examples, the additional agent is a monoclonal antibody, for example, 3F8, Abagovomab, Adecatumumab, Afutuzumab, Alacizumab, Alemtuzumab, Altumomab pentetate, Anatumomab mafenatox, Apolizumab, Arcitumomab, Bavituximab, Bectumomab, Belimumab, Besilesomab, Bevacizumab, Bivatuzumab mertansine, Blinatumomab, Brentuximab vedotin, Cantuzumab mertansine, Capromab pendetide, Catumaxomab, CC49, Cetuximab, Citatuzumab bogatox, Cixutumumab, Clivatuzumab tetraxetan, Conatumumab, Dacetuzumab, Detumomab, Ecromeximab, Eculizumab, Edrecolomab, Epratuzumab, Ertumaxomab, Etaracizumab, Farletuzumab, Figitumumab, Galiximab, Gemtuzumab ozogamicin, Girentuximab, Glembatumumab vedotin, Ibritumomab tiuxetan, Igovomab, Imciromab, Intetumumab, Inotuzumab ozogamicin, Ipilimumab, Iratumumab, Labetuzumab, Lexatumumab, Lintuzumab, Lorvotuzumab mertansine, Lucatumumab, Lumiliximab, Mapatumumab, Matuzumab, Mepolizumab, Metelimumab, Milatuzumab, Mitumomab, Morolimumab, Nacolomab tafenatox, Naptumomab estafenatox, Necitumumab, Nimotuzumab, Nofetumomab merpentan, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Satumomab pendetide, Sibrotuzumab, Sonepcizumab, sorafenib, sunitinib, Tacatuzumab tetraxetan, Taplitumomab paptox, Tenatumomab, TGN1412, Ticilimumab (=tremelimumab), Tigatuzumab, TNX-650, Trastuzumab, Tremelimumab, Tucotuzumab celmoleukin, Veltuzumab, Volociximab, Votumumab, Zalutumumab.

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

Other therapeutic agents, for example anti-tumor agents, that may or may not fall under one or more of the classifications above, also are suitable for administration in combination with the disclosed therapies. By way of example, such agents include adriamycin, apigenin, rapamycin, zebularine, cimetidine, and derivatives and analogs thereof.

Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

G. Compositions

Compositions are provided that include one or more of the disclosed conjugates, antibodies, or antigen binding fragments that specifically bind EGFRvIII, or nucleic acid molecules or CAR T cells, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, the antibody that specifically binds EGFRvIII or an antigen binding fragment thereof, or conjugate including such an antibody or antigen binding fragment, or CAR T cells, is/are formulated for parenteral administration, such as intravenous administration. Compositions including a conjugate, antibody or antigen binding fragment, or CAR T cells, as disclosed herein are of use, for example, for the treatment and/or detection of a tumor, for example a tumor occurring in breast, colorectal, lung or skin cancer. In some examples, the compositions are useful for the treatment or detection of a carcinoma.

The compositions for administration can include a solution of the conjugate, antibody or antigen binding fragment dissolved in (or CAR T cells suspended in) a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody or antigen binding fragment, conjugate, or CAR T cells in these formulations can vary widely, and will be selected primarily based on fluid volumes, viscosities, body weight and the like in accordance with the particular mode of administration selected and the subject's needs. Actual methods of preparing such dosage forms are known, or will be apparent, to those skilled in the art.

A typical composition for intravenous administration includes about 0.01 to about 30 mg/kg of antibody or antigen binding fragment or conjugate per subject per day (or the corresponding dose of a conjugate including the antibody or antigen binding fragment). Actual methods for preparing administrable compositions will be known or apparent to those skilled in the art and are described in more detail in such publications as *Remington's Pharmaceutical Science,* 19th ed., Mack Publishing Company, Easton, PA (1995). In some embodiments, the composition can be a liquid formulation including one or more antibodies, antigen binding fragments (such as an antibody or antigen binding fragment that specifically binds to EGFRvIII), in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

Antibodies, antigen binding fragments, or conjugates may be provided in lyophilized form and rehydrated with sterile water before administration, although they are also provided in sterile solutions of known concentration. The antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. Antibodies, antigen binding fragments and conjugates can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, PA, (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, NY, pp. 219-342 (1994); and Tice & Tabibi, *Treatise on Controlled Drug Delivery*, A. Kydonieus, ed., Marcel Dekker, Inc. New York, NY, pp. 315-339, (1992).

Polymers can be used for ion-controlled release of the antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, PA (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

In some examples, a subject is administered the DNA encoding the antibody, antigen binding fragments thereof, or conjugate (such as with a toxin) to provide in vivo antibody production, for example using the cellular machinery of the subject. Immunization by nucleic acid constructs is well known in the art and taught, for example, in U.S. Pat. Nos. 5,643,578, and 5,593,972 and 5,817,637. U.S. Pat. No. 5,880,103 describes several methods of delivery of nucleic acids encoding to an organism. The methods include liposomal delivery of the nucleic acids. Such methods can be applied to the production of an antibody, or antibody binding fragments thereof, by one of ordinary skill in the art.

One approach to administration of nucleic acids is direct administration with plasmid DNA, such as with a mammalian expression plasmid. The nucleotide sequence encoding the disclosed antibody, or antibody binding fragments thereof, can be placed under the control of a promoter to increase expression.

In another approach to using nucleic acids, a disclosed antibody, or antibody binding fragments thereof can also be expressed by attenuated viral hosts or vectors or bacterial vectors. Recombinant vaccinia virus, adeno-associated virus (AAV), herpes virus, retrovirus, cytomegalovirus or other viral vectors can be used to express the antibody. For example, vaccinia vectors and methods useful protocols are described in U.S. Pat. No. 4,722,848. BCG (*Bacillus* Calmette Guerin) provides another vector for expression of the disclosed antibodies (see Stover, *Nature* 351:456-460, 1991).

In one embodiment, a nucleic acid encoding a disclosed antibody, or antibody binding fragments thereof, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

H. Kits

Kits are also provided. For example, kits for detecting a tumor cell that expresses EGFRvIII in a subject, treating a tumor in a subject. The kits will typically include an antibody or antigen binding fragment that specifically binds EGFRvIII and/or a conjugate thereof.

More than one of the conjugates or antibodies or antigen binding fragments that specifically bind EGFRvIII can be included in the kit. Thus, the kit can include two or more antibodies that specifically bind EGFRvIII, or an antibody or antigen binding fragment that specifically binds EGFRvIII and a conjugate thereof, or a combination thereof. In some embodiments, an antigen binding fragment or conjugate including an antigen binding fragment, such as an Fv fragment, is included in the kit. In one example, such as for in vivo uses, the antibody can be a scFv fragment.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed EGFRvIII specific antibodies, antigen binding fragments, or conjugates. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed EGFRvIII specific antibodies or fragments thereof, or conjugates thereof, for example, in a method of treating or preventing a tumor. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

In the experimental work disclosed herein, the $EGFR_{287-302}$ loop was produced as a disulfide-limited peptide and coupled with a carrier protein, Keyhole Limpet Hemocyanin (KLH). The KLH-coupled peptide was injected into Balb/c mice. Sera from these mice were monitored for reactivity to the loop peptide and when high titers were achieved, spleens were removed for hybridoma formation. Candidate hybridoma supernatants were then assayed for reactivity with wtEGFR and EGFRvIII. Antibodies with high reactivity for EGFRvIII and low reactivity for wtEGFR were isolated and characterized, as disclosed below.

Example 1

Selection of Hybridomas Reactive for EGFRvIII

Figure 1B:
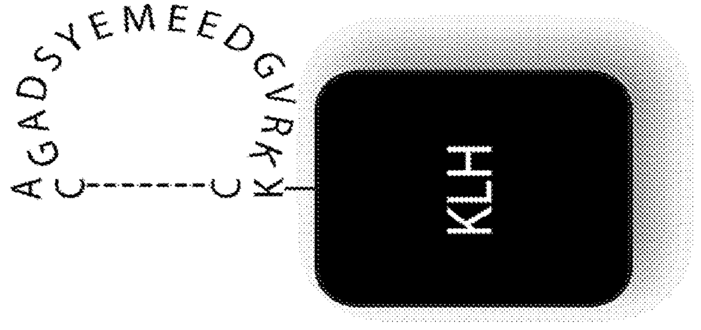
FIGS. 1A-1B. Schematic diagram of (1A) EGFR, (1B) EGFRvIII peptide antigen (aa 286-303) conjugated to KLH. Also, shown is the location of the loop and the approximate binding site of ma528 on domain III of EGFR. SEQ ID NO: 69 is shown in both FIGS. 1A and 1B.
Figure 1A:
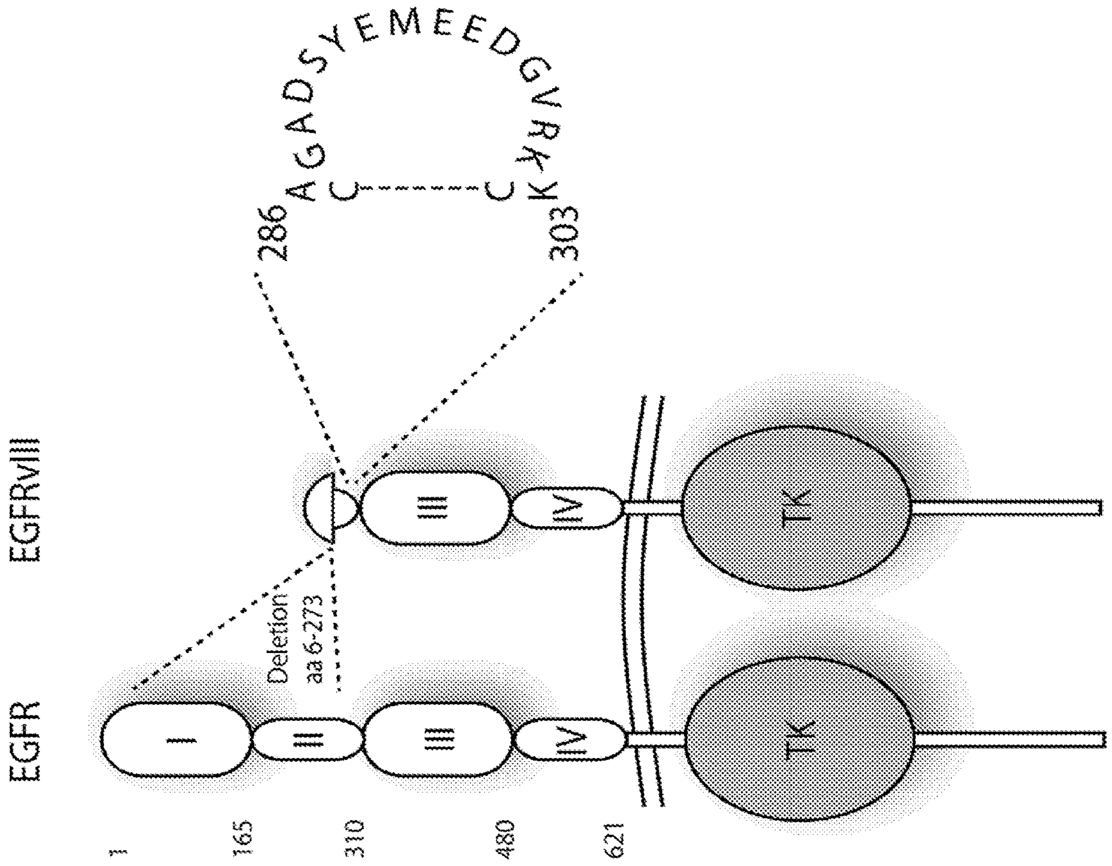

As a target for antibody-based therapy, amplified EGFR or mutant versions, including EGFRvIII, are expressed on the surface of epithelial cancers and malignant gliomas. To generate antibodies to the disulfide-limited loop 287-302 (numbering is for mature human EGFR and represented in FIG. 1A) of the extracellular domain (ECD) of EGFR, five Balb/c mice were immunized repeatedly with a KLH-conjugated peptide that included residues 286-303 (FIG. 1B). When titers to the injected peptide were above background at a 1:128,000 dilution (Table 1), spleens were harvested and candidate hybridomas produced through fusion with myeloma cell line Sp2/0.

TABLE 1

| Absorbance values for indirect ELISA assays measuring mouse antibody titers to loop peptide. | | | | | | |
|---|---|---|---|---|---|---|
| Dilution | 1:16000 | 1:32000 | 1:64000 | 1:128000 | 1:256000 | Blank |
| Mouse #371 | 0.966 | 0.545 | 0.338 | 0.194 | 0.112 | 0.060 |
| Mouse #9174 | 0.915 | 0.589 | 0.329 | 0.188 | 0.139 | 0.057 |

Hybridomas, initially uncloned, were established from two mice that exhibited particularly high titers to the immunogen (Table 1). Approximately 40 hybridoma supernatants were generated from each fusion and evaluated in ELISA format for binding to the ECD of EGFRvIII-His and for cells expressing EGFRvIII. Follow up experiments were undertaken to characterize seven promising hybridomas.

Figure 2:
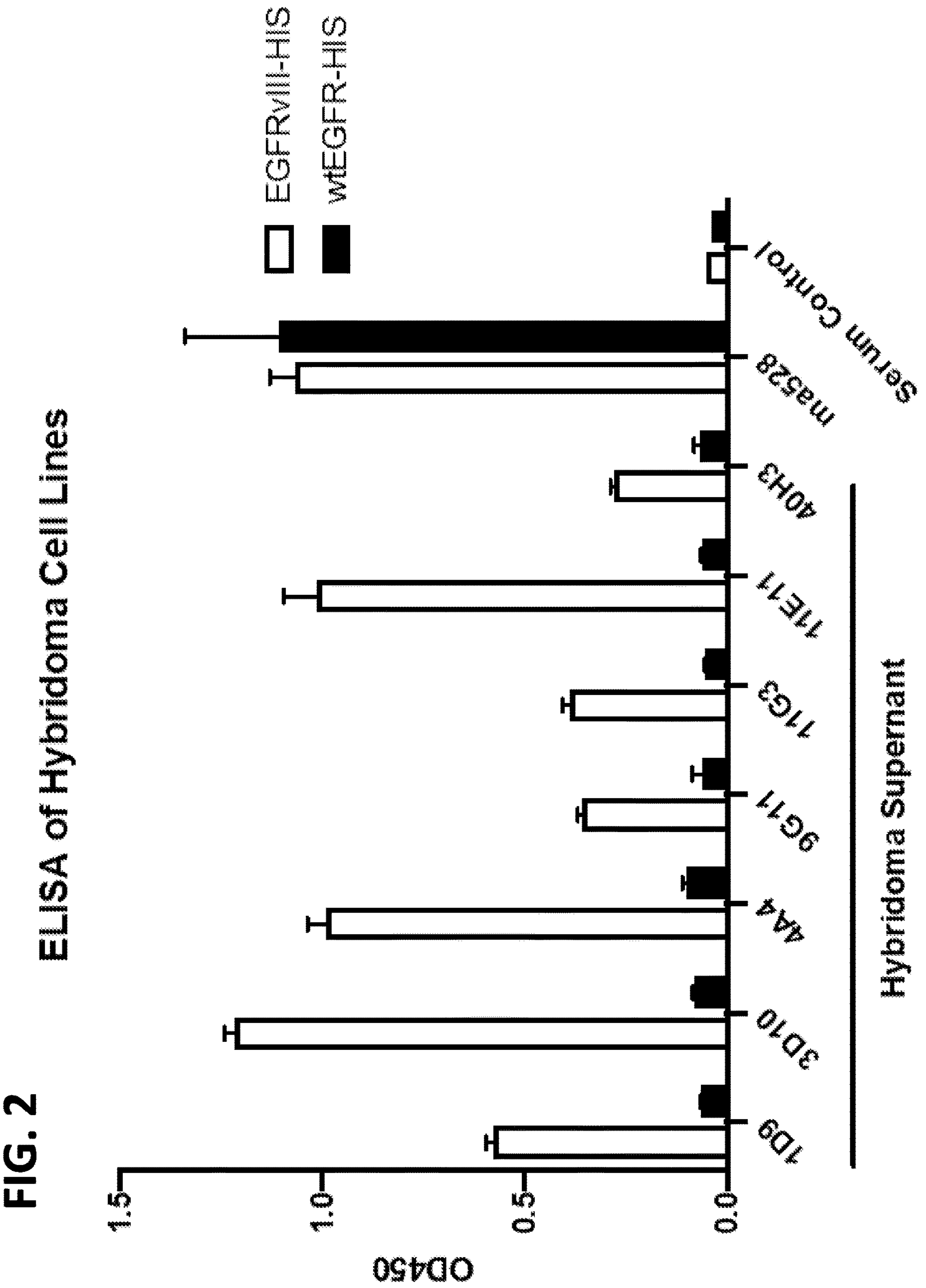
FIG. 2. Bar graph of results of individual hybridomas supernatants with enzyme linked immunosorbent assay (ELISA) reactivity for wtEGFR-His and EGFRvIII-His (ELISA) including 528 as a positive control.
Figure 3:
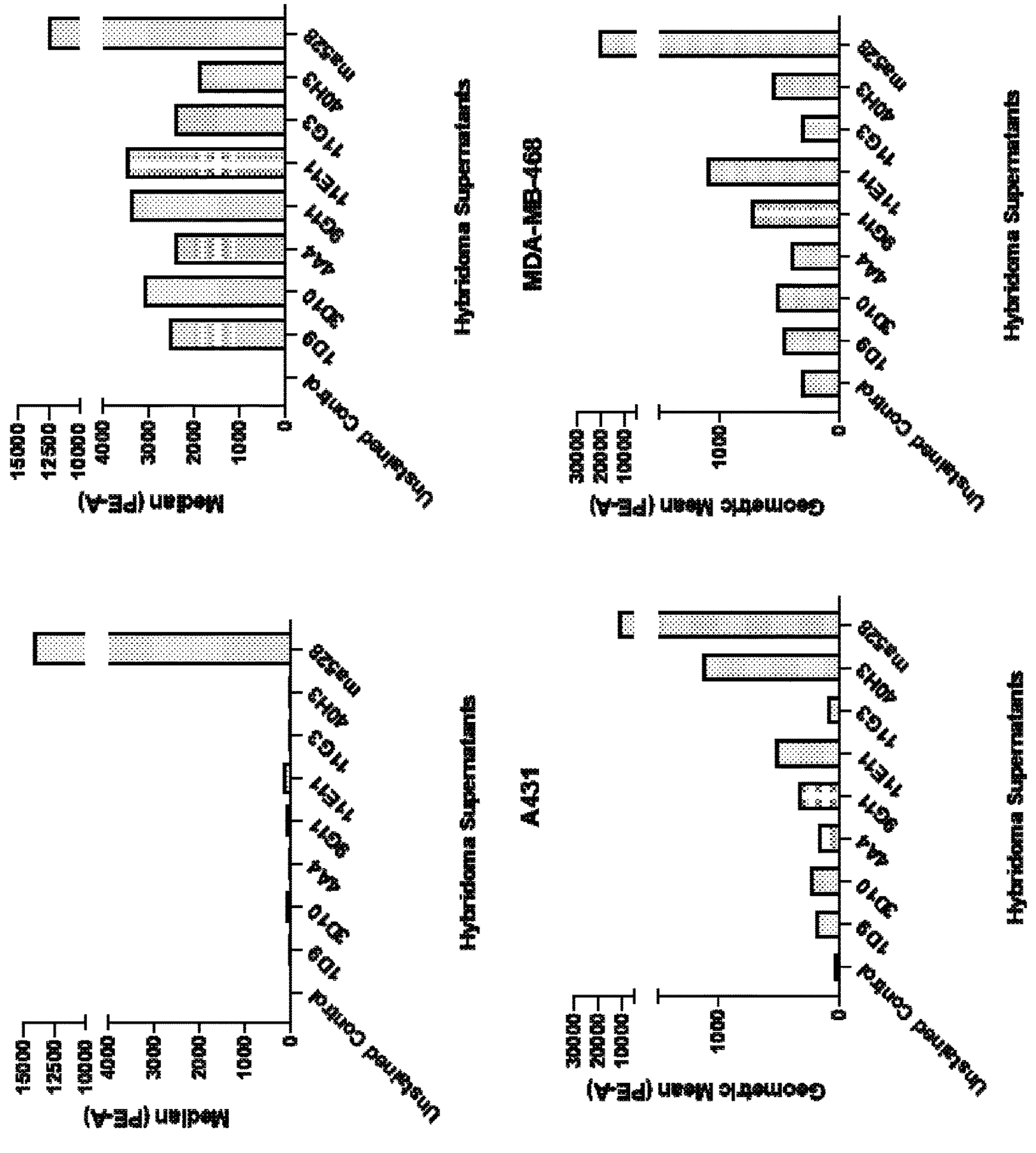
FIG. 3. Bar graphs of the reactivity of hybridoma supernatants with cells: MDA-MB-468, A431, $F98_{EGFR}$ and $F98_{npEGFRvIII}$ cells. The results show that the antibodies bind specifically. ma528 is the control.

Individual supernatants from selected hybridomas with good cell-binding activity were assayed by ELISA for binding to the ECDs of either wtEGFR-His or EGFRvIII-His. Nickel-coated 96-well plates were used to display His-tagged EGFR proteins. Results indicated a strong preference for binding to EGFRvIII-His over wtEGFR-His, confirming that 287-302 loop is displayed on EGFRvIII but poorly accessible on wtEGFR (FIG. 2). Next, the same hybridoma supernatants (diluted 1:10) were assayed for binding to rat glioma F98 cells that had been transfected with either EGFRvIII or wtEGFR. Again, binding reflected a strong interaction of supernatants with the ECD of EGFRvIII (FIG. 3) and poor reactivity for wtEGFR (FIG. 3). The monoclonal antibody ma528 that reacts with domain III of EGFR (see FIG. 1A) was used as a positive control and was shown to bind equally well to the surface of either transfected cell line (FIG. 3).

The gene encoding EGFR is amplified and/or overexpressed in certain epithelial cancers. To assay binding to cells with overexpressed EGFR, supernatants (at 1:10 dilution) were added to either the triple negative breast cancer cell line, MDA-MB-468 or the epidermoid cancer line, A431. Again, binding was noted for most supernatants over preimmunized sera as a negative control. At this juncture, antibody concentrations of supernatants were not determined. Rather, cells were cloned by limiting dilution and then grown as true 'clonal' hybridomas.

Example 2

Characterization of Purified Antibodies

Figure 4:
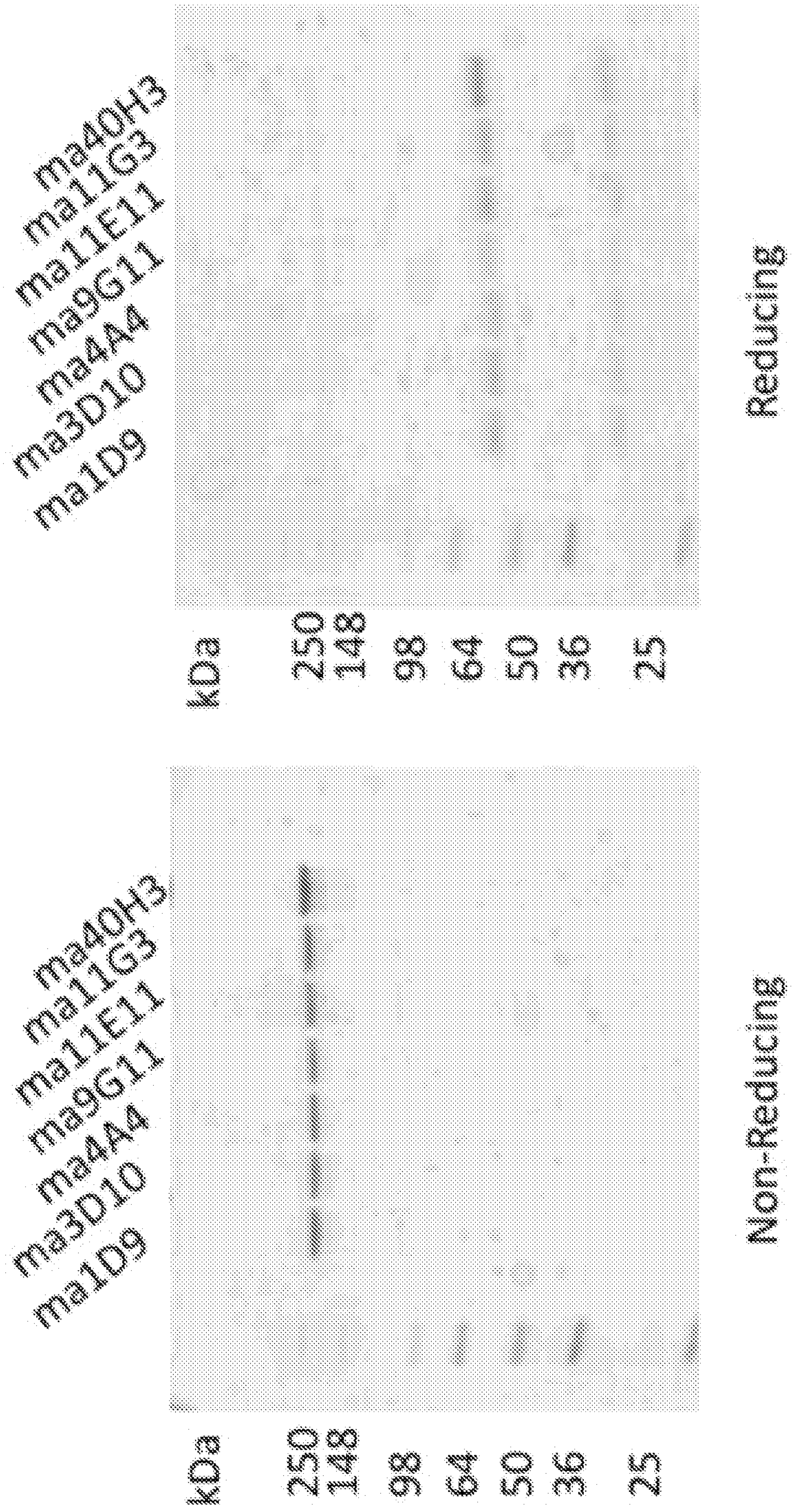
FIG. 4. SDS-PAGE gels showing purity of seven monoclonal antibodies as eluted from A/G columns.
Figure 5:
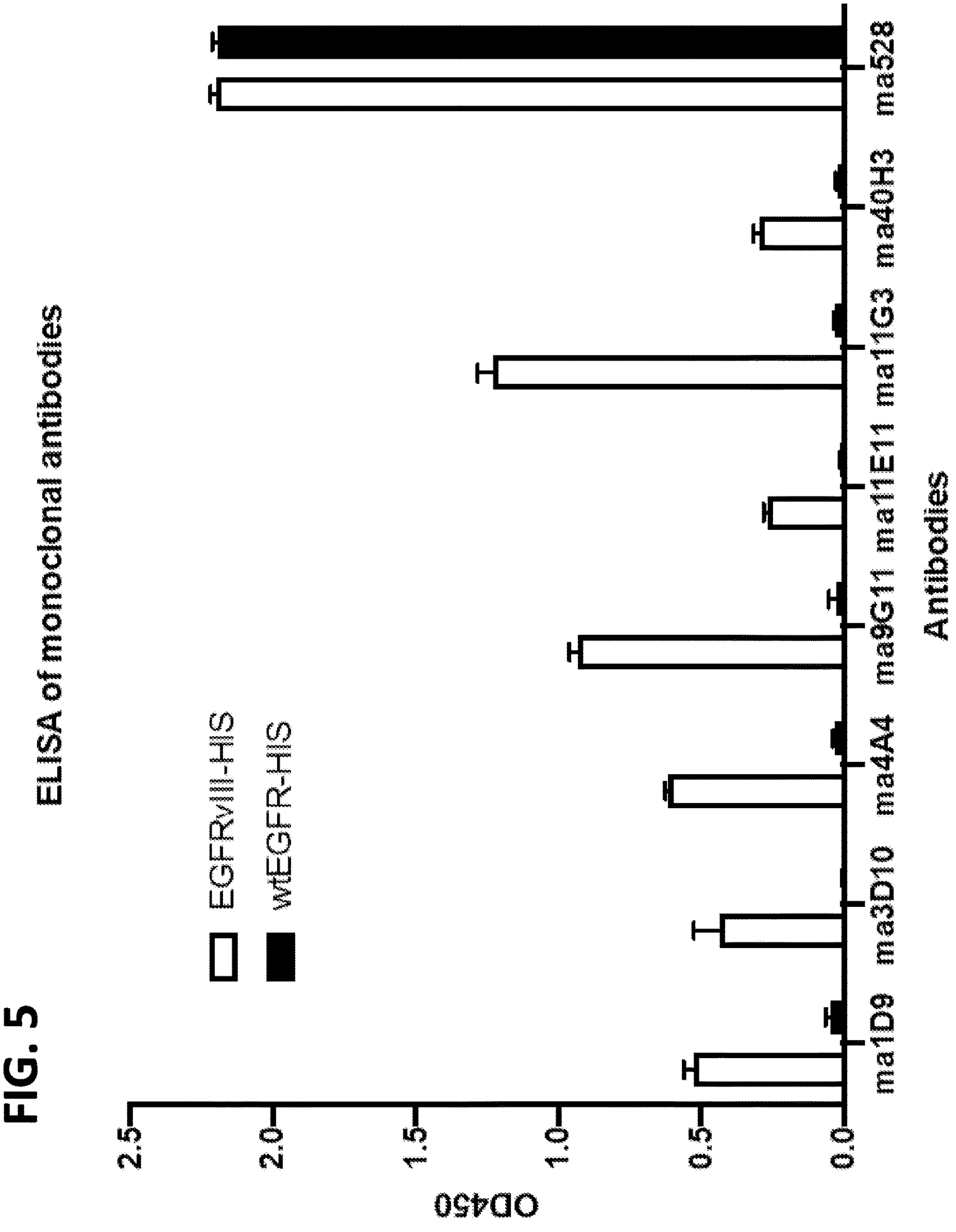
FIG. 5. Reactivity of purified monoclonal antibodies in ELISA format with wtEGFR-His and EGFRvIII-His.
Figure 6C:
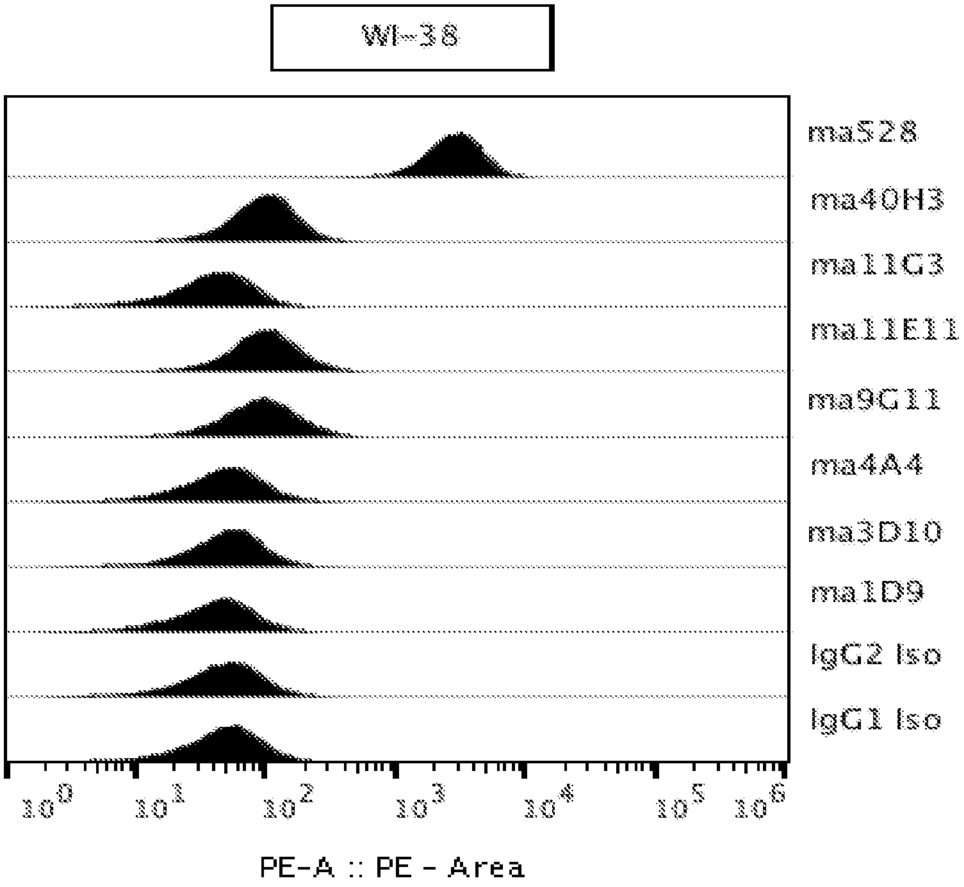

Using immobilized protein A/G, seven antibodies from cloned hybridoma supernatants were purified for further characterization. Two SDS-PAGE gels (one of reduced and one of non-reduced samples) of purified antibodies are supplied (FIG. 4). When compared with the original hybridoma supernatants, purified antibodies reacted in ELISA assays with qualitatively similar results. In fact, relatively low concentrations of antibodies (at 5 ng/ml) produced a robust signal with EGFRvIII-His and showed little or no binding to wtEGFR-His (FIG. 5). In cell-binding assays, flow cytometry was used to characterize the binding of each of the seven monoclonal antibodies. Antibodies were added at 2 ug/ml. Again, ma528 was used a positive control and matched isotype antibodies were used as non-binding negative controls. When characterizing antibody binding to $F98_{EGFR}$ cells, histograms showed strong binding of ma528 (GeoMean of 3705) weak binding of 40H3 (GeoMean of 191) and no binding by the remaining six monoclonal antibodies or the isotype controls (FIG. 6B). When binding was assessed on F98-EGFRvIII, again ma528 showed highest reactivity but was closely followed by substantial binding from all seven monoclonal antibodies with (GeoMeans ranging from ~1000-1300) (FIG. 6B). Isotype controls did not bind. Next, binding was assayed on the cancer lines MDA-MB-468 (FIG. 6A), A431 (FIG. 6A) and on WI-38 (FIG. 6C), a non-cancerous 'normal' human cell line. On MDA-MB-468 cells, ma528 followed by 40H3 showed substantial binding, while the other six antibodies showed minimal reactivity over the isotype controls (FIG. 6A). On A431 cells, a substantially similar result was achieved (FIG. 6A). However, on WI-38, which express wtEGFR at physiological levels, only ma528 showed substantial binding with a GeoMean of 2454 (FIG. 6C). On WI-38, all other antibodies had a GeoMean of less than 100 (FIG. 6C). It was concluded that functionally only antibodies 40H3 and ma528 exhibited binding for cancer-expressed EGFRF. EGFR can be overexpressed either by gene amplification or loss of transcriptional control. High level expression leads to either misfolding of the receptor or mutations in one of more of the gene copies.

However, 40H3 displayed no reactivity for the normal cells, WI-38, while ma528 reacted strongly to both cancer and normal cells. Of interest, when antibody binding to EGFRvIII transfected F98 cells was assess, the seven antibodies showed similar and substantial reactivity.

Example 3

Location of the Binding Site within the $EGFR_{28}$6-303

Figure 7:
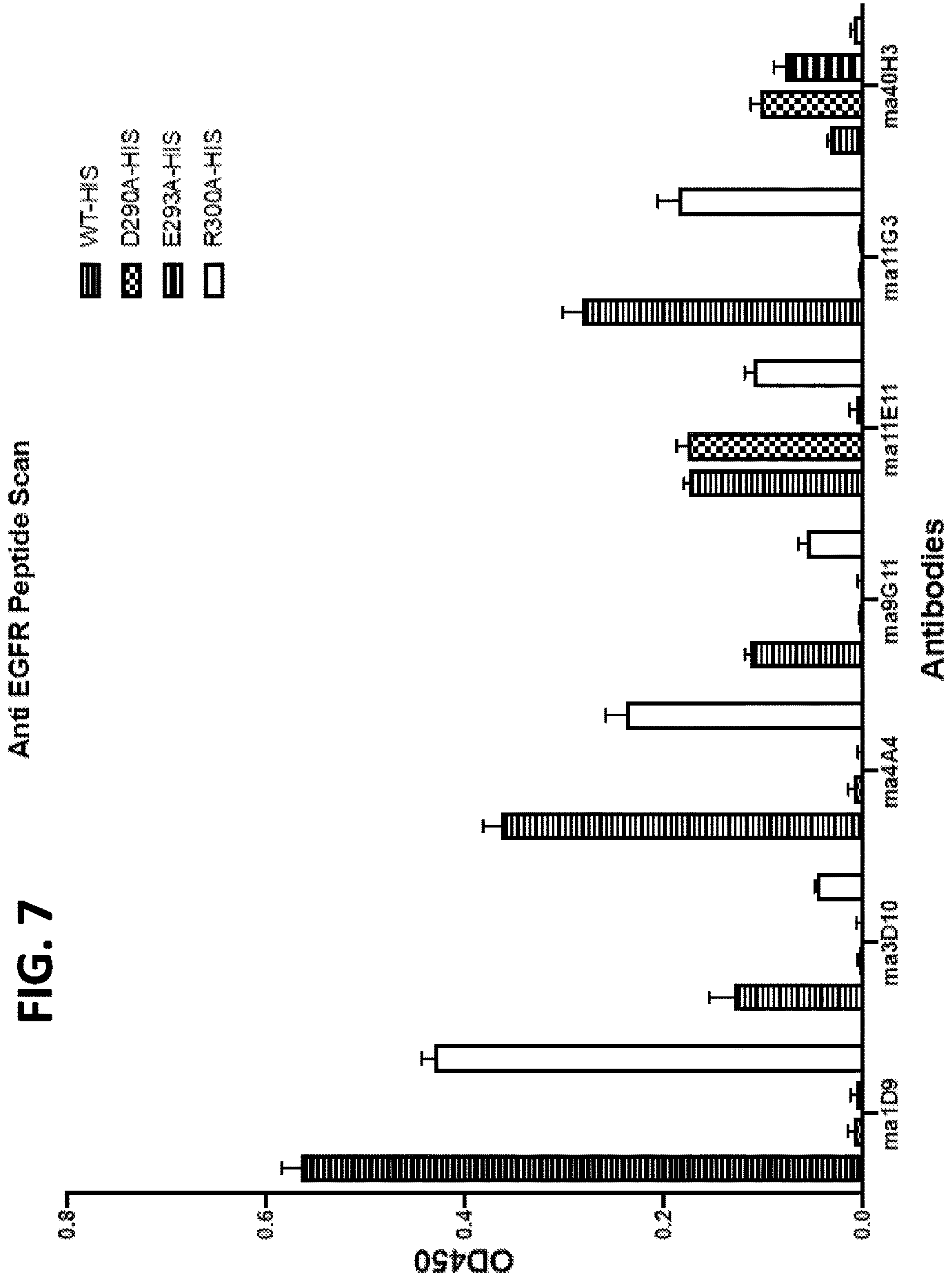
FIG. 7. Reactivity of individual antibodies with the wild-type (wt) and selected mutants of the 287-302-His peptide.

To aid in mapping the binding site of each antibody, three charged residues within the $EGFR_{28}$7-302 loop, D290, E293 and R300, were each changed to alanine and produced as his-tagged peptides (FIG. 7). The wt sequence of the 287-302 loop was produced similarly. Because the charge residues were spread out across the loop, relative antibody binding activity could provide information about the location of critical residues involved in interaction of each antibody. Results indicated that antibodies fell into one of three groups: 1) binding was lost when residues D290 and E293 were changed to alanine: 2) binding was lost only with a change of E293 to alanine: and 3) reactivity was lost when R300 was changed to alanine. In sum, the seven EGFRvIII-reactive antibodies segregated into at least three groups based on binding characteristics toward his-tagged peptides. Group 1 contained five of the seven antibodies: 1D9, 3D10, 4A4, 9G11 and 11E3. Group 2 had 11E11 while Group 3 included 40H3 (Table 2).

TABLE 2

| Isotype determination and peptide reactivity of each monoclonal antibody.] | | | | | |
|---|---|---|---|---|---|
| | | Reactivity to: | | | |
| Antibodies | Isotype | Wildtype | D290A | E293A | R300A |
| 1D9 | IgG2b, K | ✓ | | | ✓ |
| 3D10 | IgG2b, K | ✓ | | | ✓ |
| 4A4 | IgG2b, K | ✓ | | | ✓ |
| 9G3 | IgG2b, K | ✓ | | | ✓ |
| 11E11 | IgG2b, K | ✓ | | | ✓ |
| 11G3 | IgG2b, K | ✓ | ✓ | | ✓ |
| 40H3 | IgG1, K | ✓ | ✓ | ✓ | |

THE $EGFR_{287-302}$ loop: CGADSYEMEEDGVRKC (SEQ ID NO: 69).

Example 4

Sequence Analysis of the Antibodies

The variable regions of both the heavy chains and lights of the seven antibodies were sequenced and the deduced amino acids were determined (FIG. 8). Sequences analysis of the cell-binding antibodies suggest that the seven antibodies can be cluster into four groups. 3D10 and 9G11 (Group 1) share similar sequences with 2 amino acids in the $V_H$ chain and 1 amino acids difference in the $V_L$ chain. There are 3 amino differences in the $V_H$ chain and 1 difference in the $V_L$ chain in between 1D9 and 4A4 (Group 2) and lastly when 11E 11 and 11G3 (Group 3) were compared, there were 4 amino acid differences in the $V_H$ chain and 2 differences in the $V_L$ chain. None of the amino acid differences within a particular group were located in CDR3 of either $V_H$ or $V_L$ region. Sequence analysis suggests that 40H3 appears to cluster separately with the most diverse sequence in comparison to the other three groups. It has 75% to 80% sequence similarity in the $V_H$ chain and 50% to 60% sequence similarity in the $V_L$ when in comparison with the other six antibodies. In contrast, the other six have a sequence similarity of 88% to 98% in the $V_H$ chain and 85% to 98% in the $V_L$ when comparing amongst themselves. Also, amino acid sequences differences between 40H3 and the other three groups were seen in all 3 CDR regions in both $V_H$ and $V_L$ chains.

TABLE 3

| Amino acid sequence with highest similarity, pair-wise comparison of the CDRs and framework (FR) regions. | | | | | |
|---|---|---|---|---|---|
| PAIR | ANTIBODY | HEAVY CHAIN CDR DIFFERENCE | HEAVY CHAIN FR DIFFERENCE | LIGHT CHAIN CDR DIFFERNCE | LIGHT CHAIN FR DIFFERENCE |
| A | 3D10 | CDR2 | YES | NONE | NO |
| A | 9G11 | CDR2 | YES | NONE | NO |
| B | 1D9 | NONE | YES | NONE | YES |
| B | 4A4 | NONE | YES | NONE | YES |
| C | 11E11 | CDR2 | YES | CDRI | YES |
| C | 11G3 | CDR2 | YES | CDRI | YES |

Example 5

Antibody cDNA Sequences from Cloned Hybridomas

The DNA sequences for the heavy and light chains for each cloned antibody were determined and are provided herein.

Example 6

Exemplary Therapeutic Antibody-based Agents

Antibodies, with a few exceptions, are rarely cytotoxic for tumor cells, even when they bind with good affinities. This prompts the addition of a toxic payload to the antibody or a strategy to modify the parent antibody to attract immune cells to the tumor. The fusion of the Fv portion of the heavy and light chains (cDNAs) with PE38 provides recombinant immunotoxins. 40H3 can be used to deliver a toxic payload, and the other antibodies can also be used. The parent antibody of 40H3 is non-toxic for human tumor cells while the immunotoxin is toxic in the nanomolar range (FIG. 9). Another exemplary construct is shown in FIG. 19, wherein an antibody binding fragment (sch as an scFv), or monoclonal antibody is modified to include a cysteine residue, and a drug is conjugated to the antibody or antigen binding fragment.

Example 7

Binding Affinity of 40H3 Against EGFR Loop, EGFRwt ECD and EGFRvIII ECD

The binding affinity of 40H3 for the eighteen amino acid peptide loop (286-302 of the EGFR ECD; referred to below to as "EGFR loop") as described by the equilibrium dissociation constant, $K_d$, was ~1 nM (FIG. 11 and Table 4). The binding affinity of 40H3 against EGFRvIII ECD had a $K_d$ value of ~270 pM (FIG. 11 and Table 4). This dissociation constant indicated that the 40H3 antibody exhibited a high affinity towards the exposed EGFR loop. In contrast, the binding of 40H3 against the EGFRwt ECD did not produce a significant $K_d$ value given its low association rate (FIG. 11).

TABLE 4

| $K_d$ values of 40H3 antibodies against EGFRwt ECD, EGFRvIII ECD or EGER loop | | | | |
|---|---|---|---|---|
| Sample ID | Loading Sample ID | KD (M) | Kon(1/Ms) | Koff(1/s) |
| ma40H3 GS | EGFRvIII-HIS | 2.70E−10 | 1.67E+05 | 4.51E−05 |
| ma40H3 GS | EGFRlp-HIS | 1.11E−09 | 5.49E+04 | 6.07E−05 |

Example 8

Cytotoxicity of 40H3-PE38 Against EGFR and EGFRvIII Expressing Cell Lines

40H3-PE38 immunotoxin was produced by fusing the scFV region of 40H3 with a 38 kDa C-terminal fragment of *Pseudomonas aeruginosa* Exotoxin A (PE). The binding affinity, $K_d$, of 40H3 PE38 against the EGFR loop was 2.3 nM (FIG. 12, Table 5).

TABLE 5

| $K_d$ values of 40H3 DM1, 40H3 MMAE or 40H3 PE38 against EGFR loop | | | | |
|---|---|---|---|---|
| Sample ID | Loading Sample ID | KD (M) | Kon(1/Ms) | Koff(1/s) |
| 40H3 PE38 | EGFRlp-HIS | 2.30E−09 | 1.97E+05 | 4.54E−04 |
| 40H3 MMAE | EGFRlp-HIS | 8.46E−11 | 2.65E+05 | 2.24E−05 |
| 40H3 DM1 | EGFRlp-HIS | 4.42E−10 | 2.02E+05 | 8.95E−05 |

The cytotoxic potential of 40H3-PE38 was evaluated against cells that expressed either EGFRvIII or EGFR ($F98_{npEGFRvIII}$ and $F98_{EGFR}$ respectively) (FIG. 10). 40H3-PE38 exhibited cytotoxic activity against $F98_{npEGFRvIII}$ cells with an $IC_{50}$ of less than 1 nM (~0.4 nM) and was 10-fold more potent relative to the same cells expressing wild type EGFR, $F98_{EGFR}$, which had an $IC_{50}$ of ~4 nM (Table 6).

TABLE 6

| $IC_{50}$ values of 40H3 PE38 or PE64 against MDA-MB-468, MDA-MB-468 or WI-38 | | |
|---|---|---|
| Sample ID | 40H3PE38 $IC_{50}$ (nM) | PE64 $IC_{50}$ (nM) |
| WI-38 | >100 | 0.065 |
| $F98_{EGFR}$ | 4 | 0.02 |
| $F98_{npEGFRvIII}$ | 0.4 | 0.02 |

This result confirms the antibody's preferred binding specificity for EGFRvIII over wild type EGFR. WI-38 cells which are derived from lung fibroblasts and have normal EGFR expression did not show any loss of viability when incubated with 40H3-PE38 ($IC_{50}$>10 nM) (FIG. 10 and Table 6).

Example 9

Cytotoxicity of 40H3 MMAE Against EGFRvIII Expressing or EGFR Overexpressing Cell Lines The 40H3 monoclonal antibody was conjugated with monomethyl auristatin E (MMAE) with a cleavable linker mc-vc-PAB. The resulting antibody drug conjugate, 40H3 MMAE, shows strong binding towards the EGFR loop indicating that the conjugation process did not interfere with its binding ability (FIG. 12, Table 5). The cytotoxic potential of 40H3 MMAE was evaluated against cells that expressed either EGFRvIII ($F98_{npEGFRvIII}$) or EGFR overexpressing cancer cell line (MDA-MB-468 and A431) (FIG. 15, Table 7).

TABLE 7

| $IC_{50}$ summary table for ADC and IT | | | | |
|---|---|---|---|---|
| | $IC_{50}$ (nM) | | | |
| Cell Line Sample | A431 | MDA-MB-468 | $F98_{npEGFRvIII}$ | DKMG EGFRvIII |
| 40H3 MMAE | ~8.4 | ~8.1 | — | 1.9 |
| 40H3 DM1 | 75 | 30 | — | 0.56 |
| 40H3 | — | — | — | — |
| 40H3 PE38 | ~2.3 | ~7 | ~3 | 0.25 |

*The values are an average of all the available data of 72 hrs (excluding the experiment with only 1K cell/well)

The 40H3 MMAE exhibited cytotoxic activity against both MDA-MB-468 and A431 an $IC_{50}$ of around 8 nM for both cell line (Table 7). $F98_{npEGFRvIII}$ cells which are derived from a rat glioblastoma did not display any loss of viability when incubated with 40H3 MMAE ($IC_{50}$~100 nM) (FIG. 16 and Table 7).

Example 10

Cytotoxicity of 40H3 DM1 Against EGFRvIII Expressing or EGFR Overexpressing Cell Lines The 40H3 monoclonal antibody was conjugated with maytansine (DM1) with a non-cleavable linker. The resulting antibody drug conjugated, 40H3 DM1, shows strong binding towards the EGFR loop indicating that the conjugation process did not interfere with its binding ability (FIG. 12, Table 5). The cytotoxic potential of 40H3 DM1 was evaluated against cells that expressed either EGFRvIII ($F98_{npEGFRvIII}$) or EGFR overexpressing cancer cell line (MDA-MB-468 and A431) (FIG. 15, Table 7). The 40H3 MMAE exhibited cytotoxic activity against both MDA-MB-468 and A431 an $IC_{50}$ of around 75 nM and 30 nM respectively (Table 7). $F98_{npEGFRvIII}$ cells which is derived from rat glioblastoma did not display any significant cell death when incubated with 40H3 DM1 ($IC_{50}$>100 nM) (FIG. 15 and Table 7).

Example 11

Cytotoxicity of 40H3-PE38 Against Patient Derived Xenograft (PDX) Glioblastoma Cell Line The patient derived xenograft (PDX) glioblastoma cell line, GBM39, was obtained. This PDX cell line was shown to have both EGFR and EGFRvIII expression. Flow cytometry analysis illustrates the EGFR expression of the PDX via binding by the pan EGFR monoclonal antibody 528 (FIG. 13, Table 8).

TABLE 8

| Flow cytometry data of 528 monoclonal antibodies against GBM39 presented in terms of median fluorescent intensity as well as the total number of cells (count) | | | |
|---|---|---|---|
| GBM39 | Sample Name | Median | Count |
| | aMouse | 309 | 11150 |
| | 528 (0.2 μg/ml) | 12677 | 11293 |
| | 528 (2 μg/ml) | 29760 | 12375 |

TABLE 8-continued

Flow cytometry data of 528 monoclonal antibodies against GBM39 presented in terms of median fluorescent intensity as well as the total number of cells (count)

| GBM39 | Sample Name | Median | Count |
|---|---|---|---|
| | 528 (20 μg/ml) | 30266 | 11255 |
| | Unstained | 112 | 10731 |

Both 40H3 and 40H3 PE38 showed binding to PDX suggesting the presence of EGFRvIII and/or misfolded overexpressed EGFR (FIG. 13, Tables 9 and 10). The sensitivity of GBM39 to 40H3 based antibody therapeutics was examined by treatment with 40H3 PE38 (FIG. 14).

TABLE 9

Flow cytometry data of 40H3 monoclonal antibodies against GBM39 presented in terms of median fluorescent intensity as well as the total number of cells (count)

| GBM39 | Sample Name | Median | Count |
|---|---|---|---|
| | aMouse | 309 | 11150 |
| | 40H3 (0.2 μg/ml) | 9453 | 11001 |
| | 40H3 (2 μg/ml) | 10710 | 10963 |
| | 40H3 (20 μg/ml) | 8601 | 12014 |
| | Unstained | 112 | 10731 |

TABLE 10

Flow cytometry data of 40H3 PE38 immunotoxins against GBM39 presented in terms of median fluorescent intensity as well as the total number of cells (count)

| GBM39 | Sample Name | Median | Count |
|---|---|---|---|
| | aMouse | 309 | 11150 |
| | m40-1 | 304 | 11420 |
| | 40H3 PE38 (0.2 μg/ml) | 460 | 12247 |
| | 40H3 PE38 (2 μg/ml) | 1625 | 12350 |
| | 40H3 PE38 (20 μg/ml) | 3907 | 12094 |
| | Unstained | 112 | 10731 |

Example 12

Cytotoxicity of 40H3 Derived Immunotoxins and Antibody Drug Conjugate Against Human Glioblastoma Cell Line with EGFRvIII Expression The efficacy of 40H3 based antibody therapeutics was examined on human glioblastoma cell line, DKMG, that was transfected with EGRvIIII. Flow cytometry analysis indicates binding of 40H3 as well as the pan EGFR antibody 528 (FIG. 17, Tables 11 and 12).

TABLE 11

Flow cytometry data of 40H3 antibodies against DKMG-EGFRvIII presented in terms of median fluorescent intensity as well as the total number of cells (count)

| DKMG-EGFRvIII | Sample Name | Median | Count |
|---|---|---|---|
| | aMouse | 513 | 9863 |
| | 40H3 (0.1 μg/ml) | 3212 | 9965 |
| | 40H3 (1 μg/ml) | 7316 | 9760 |
| | 40H3 (10 μg/ml) | 6036 | 9784 |
| | Unstained | 71 | 9613 |

TABLE 12

Flow cytometry data of 528 antibodies against DKMG-EGFRvIII presented in terms of median fluorescent intensity as well as the total number of cells (count)

| DKMG-EGFRvIII | Sample Name | Median | Count |
|---|---|---|---|
| | aMouse | 513 | 9863 |
| | 528 (0.1 μg/ml) | 12893 | 9769 |
| | 528 (1 μg/ml) | 14314 | 9889 |
| | 528 (10 μg/ml) | 13471 | 9712 |
| | Unstained | 71 | 9613 |

EGFR directed cell killing of DKMG-EGFRvIII was demonstrated by treatment with antibody drug conjugates 40H3 MMAE or 40H3 DM1 and immunotoxins 40H3 PE38. All three 40H3 antibody derived variants induced cytotoxicity in DKMG-EGFRvIII cell line (FIG. 18, Table 7). Unconjugated, naked 40H3 antibodies did not induce cytotoxicity activity.

Example 13

Materials and Method for Examples 7-12

Cytotoxicity assays (FIGS. 10, 13, 15, 16 and 9; Tables 6 and 7): Ten thousand cells per well in a volume of 100 μl were plated in 96-well plate. After 24 hours, antibody drug conjugates (ADCs; 40H3 MMAE or 40H3 DM1), antibody (40H3), immunotoxin (40H3 PE38) or *Pseudomonas* exotoxin A (PE64) were added at the indicated concentrations (100, 10, 1 and 0.1 nM for ADCs and monoclonal antibodies; 10, 1, 0.1 and 0.01 nM for immunotoxins; 1, 0.1, 0.01, 0.001 nM for PE64). After 72 hours (48 hours for GBM39; FIG. 3), viability was determined using the CellTiter-Glo Luminescent Cell Viability Assay kit (Promega, Madison WI). This assay quantifies the amount of ATP present, signaling the presence of metabolically active cells. ATP was measured as luminescence produced by the mono-oxygenation of luciferin catalyzed by the Ultra-Glo-luciferase. The luminescence of each well was measured and the values were presented as a percentage relative to untreated cells (control). Data were from at least two independent experiments with triplicate wells for each immunotoxin concentration.

Binding affinity assays (FIGS. 11 and 12; Tables 4 and 5): The binding affinity constant, '$K_d$', of antibody drug conjugates (ADCs; 40H3 MMAE or 40H3 Dml), antibody (40H3) or immunotoxin (40H3-PE38) against the C-terminal His tagged EGFRvIII ECD (Acrobiosystem, DE, USA) were measured using the Octet Red96 analyzer (Pall Life Sciences, New York, USA). The EGFRvIII ECD-HIS was captured on Ni-NTA biosensors and used as the 'antigen'. Briefly, all ligand and antibodies were diluted in buffer composed of 1×PBS, 1% BSA and 0.05% Tween. 40H3-PE38 was diluted to 250 nM, 125 nM, 62.5 nM, 31.25 nM, 15.625 nM and 7.813 nM. 2 ug/ml (at 200 ul) of EGFR1p-HIS, EGFRwt ECD-HIS or EGFRvIII-HIS was used as 'antigen'. The condition of the $K_d$ determination was as follows: 10 min presoak, 60 sec baseline establishment, 120 sec antigen loading, 120 sec baseline re-establishment after antigen loading, 120 sec for 40H3 PE38 10 association, and finally 20 min for dissociation. The baseline and association buffer and the dissociation buffers were at pH 7.4. All of the procedures were done at 30 C. Binding kinetics were analyzed using the ForteBio Data Analysis 11.1 Software. The $K_d$ values were determined using the Global Fit option where all the $K_d$ was determined based on all the difference concentration combine.

Flow Cytometry assays (FIGS. 14 and 17; Table 8-12): Antibodies or immunotoxins were incubated with suspended cells (1×105 cells per well) in a 96-well plate at 4° C. for 1 hour in FACS buffer consisting of PBS (K D Medical, MD, USA), 2 mM EDTA (K D Medical, MD, USA), 1% BSA (Sigma-Aldrich, MO, USA) and 0.1% sodium azide (Sigma-Aldrich, MO, USA). M40-1, a mouse anti-PE antibody, was used to detect immunotoxin binding. Bound antibodies were detected with R-phycoerythrin conjugated F(ab')2 goat anti-mouse IgG Fcγ (Cat #115-116-071; Jackson ImmunoResearch, ME, USA) at 1:250 dilution for 45-60 min at 4° C. Antibody binding was characterized with the SA3800 Spectral Analyzer (Sony Biotechnology, San Jose, CA, USA) and the data were analyzed with FlowJo (Tree Star, Inc., Ashland, OR, USA) and displayed in histogram format with the median fluorescence intensity plotted.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. An isolated monoclonal antibody or antigen binding fragment thereof, comprising:

a) a heavy chain variable region ($V_H$) and a light chain variable region ($V_L$) comprising a heavy chain complementarity determining region (HCDR)1, a HCDR2, and a HCDR3, and a light chain complementarity determining region (LCDR)1, a LCDR2, and a LCDR3 of the $V_H$ and $V_L$ set forth as SEQ ID NOs: 1 and 2, respectively;

b) a $V_H$ and an $V_L$ comprising a HCDR1, a HCDR2, and a HCDR3, and a LCDR1, a LCDR2, and a LCDR3 of the $V_H$ and $V_L$ set forth as SEQ ID NOs: 11 and 12, respectively;

c) a $V_H$ and a $V_L$ comprising a HCDR1, a HCDR2, and a HCDR3, and a LCDR1, a LCDR2, and a LCDR3 of the $V_H$ and $V_L$ set forth as SEQ ID NOs: 13 and 14, respectively; or d) a $V_H$ and a $V_L$ comprising a HCDR1, a HCDR2, and a HCDR3, and a LCDR1, a LCDR2, and a LCDR3 of the $V_H$ and $V_L$ set forth as SEQ ID NOs: 15 and 16, respectively, wherein the monoclonal antibody specifically binds to epidermal growth factor receptor (EGFR) variant III (vIII).

2. The isolated monoclonal antibody or antigen binding fragment thereof of claim 1, comprising a) a $V_H$ and a $V_L$ comprising a HCDR1, a HCDR2, and a HCDR3, and a LCDR1, a LCDR2, and a LCDR3 of the $V_H$ and $V_L$ set forth as SEQ ID NOs: 17 and 12, respectively;

b) a $V_H$ and a $V_L$ comprising a HCDR1, a HCDR2, and a HCDR3, and a LCDR1, a LCDR2, and a LCDR3 of the $V_H$ and $V_L$ set forth as SEQ ID NOs: 26 and 12, respectively;

c) a $V_H$ and a $V_L$ comprising a HCDR1, a HCDR2, and a HCDR3, and a LCDR1, a LCDR2, and a LCDR3 of the $V_H$ and $V_L$ set forth as SEQ ID NOs: 29 and 30, respectively;

d) a $V_H$ and an $V_L$ comprising a HCDR1, a HCDR2, and a HCDR3, and a LCDR1, a LCDR2, and a LCDR3 of the $V_H$ and $V_L$ set forth as set forth as SEQ ID NOs: 39 and 40, respectively;

e) a $V_H$ and an $V_L$ comprising a HCDR1, a HCDR2, and a HCDR3, and a LCDR1, a LCDR2, and a LCDR3 of the $V_H$ and $V_L$ set forth as SEQ ID NOs: 43 and 44, respectively; or f) a $V_H$ and an $V_L$ comprising a HCDR1, a HCDR2, and a HCDR3, and a LCDR1, a LCDR2, and a LCDR3 of the $V_H$ and $V_L$ set forth as SEQ ID NOs: 53 and 54, respectively.

3. The antibody or antigen binding fragment of claim 1, wherein a) the HCDR1, the HCDR2, the HCDR3, the LCDR1, the LCDR2, and the LCDR3 comprise the amino acids sequences set forth as SEQ ID NOs: 5, 6, 7, 8, 9 and 10, respectively;

b) the HCDR1, the HCDR2, the HCDR3, the LCDR1, the LCDR2, and the LCDR3 comprise the amino acids sequences set forth as SEQ ID NOs: 20, 21, 22, 23, 24 and 25, respectively;

c) the HCDR1, the HCDR2, the HCDR3, the LCDR1, the LCDR2, and the LCDR3 comprise the amino acids sequences set forth as SEQ ID NOs: 20, 28, 22, 23, 24 and 25, respectively;

d) the HCDR1, the HCDR2, the HCDR3, the LCDR1, the LCDR2, and the LCDR3 comprise the amino acids sequences set forth as SEQ ID NOs: 33, 34, 35, 36, 37 and 38 respectively;

e) the HCDR1, the HCDR2, the HCDR3, the LCDR1, the LCDR2, and the LCDR3 comprise the amino acids sequences set forth as SEQ ID NOs: 47, 48, 49, 50, 51 and 52, respectively; or f) the HCDR1, the HCDR2, the HCDR3, the LCDR1, the LCDR2, and the LCDR3 comprise the amino acids sequences set forth as SEQ ID NOs: 47, 57, 49, 58, 51 and 52, respectively.

4. The antibody or antigen binding fragment of claim 3, wherein a) the $V_H$ and the $V_L$ comprise the amino acid sequences at least 90% identical to the amino acid sequences set forth as SEQ ID NOs: 1 and 2, respectively;

b) the $V_H$ and the $V_L$ comprise the amino acid sequences at least 90% identical to the amino acid sequences set forth as SEQ ID NOs: 17 and 12, respectively;

c) the $V_H$ and the $V_L$ comprise the amino acid sequences at least 90% identical to the amino acid sequences set forth as SEQ ID NOs: 26 and 12, respectively;

d) the $V_H$ and the $V_L$ comprise the amino acid sequences at least 90% identical to the amino acid sequences set forth as SEQ ID NOs: 29 and 30, respectively;

e) the $V_H$ and the $V_L$ comprise the amino acid sequences at least 90% identical to the amino acid sequences set forth as SEQ ID NOs: 39 and 40, respectively;

f) the $V_H$ and the $V_L$ comprise the amino acid sequences at least 90% identical to the amino acid sequences set forth as SEQ ID NOs: 43 and 44, respectively; or g) the $V_H$ and the $V_L$ comprise the amino acid sequences at least 90% identical to the amino acid sequences set forth as SEQ ID NOs: 53 and 54, respectively.

5. The antibody or antigen binding fragment of claim 1, comprising a human framework region.

6. The antibody or antigen binding fragment of claim 1, wherein:

a) the $V_H$ and the $V_L$ comprise the amino acid sequences set forth as SEQ ID NOs: 1 and 2, respectively;

b) the $V_H$ and the $V_L$ comprise the amino acid sequences set forth as SEQ ID NOs: 17 and 12, respectively;

c) the $V_H$ and the $V_L$ comprise the amino acid sequences set forth as SEQ ID NOs: 26 and 12, respectively;

d) the $V_H$ and the $V_L$ comprise the amino acid sequences set forth as SEQ ID NOs: 29 and 30, respectively;

e) the $V_H$ and the $V_L$ comprise the amino acid sequences set forth as SEQ ID NOs: 39 and 40, respectively;

f) the $V_H$ and the $V_L$ comprise the amino acid sequences set forth as SEQ ID NOs: 43 and 44, respectively; or g) the $V_H$ and the $V_L$ comprise the amino acid sequences set forth as SEQ ID NOs: 53 and 54, respectively.

7. The antibody of claim 1, wherein the antibody comprises a human constant domain.

8. The antibody of claim 1, wherein the antibody is an IgG.

9. The antibody of claim 1, comprising a recombinant constant domain comprising a modification that increases the half-life of the antibody.

10. The antibody or antigen binding fragment of claim 1, conjugated to a toxin or a chemotherapeutic agent.

11. The antibody or antigen binding fragment of claim 10, wherein the toxin is a *Pseudomonas* exotoxin (PE), ricin, abrin, diphtheria toxin, ribotoxin, ribonuclease, saporin, calicheamicin, or a botulinum toxin.

12. The antibody of antigen binding fragment of claim 11, wherein the toxin is the PE, and wherein the PE is PE25, PE38 or PE40.

13. The antibody of antigen binding fragment of claim 10, wherein the chemotherapeutic agent is Monomethyl Auristatin E or a maytansinoid.

14. The antigen binding fragment of claim 1.

15. The antigen binding fragment of claim 14, wherein the antigen binding fragment is a Fv, dsFV, ds-scvFV, Fab, $F(ab')_2$, scFV or a $scFV_2$ fragment.

16. The antibody or antigen binding fragment of claim 14, conjugated to a detectable marker.

17. A chimeric antigen T cell receptor comprising the antigen binding fragment of claim 14.

18. A bispecific antibody comprising the antibody or antigen binding fragment of claim 1.

19. An isolated nucleic acid molecule encoding the antibody or antigen binding fragment of claim 1, or a chimeric antigen T cell receptor comprising the antigen binding fragment.

20. The nucleic acid molecule of claim 19, comprising a) the $V_H$ and/or the $V_L$ nucleotide sequences set forth as SEQ ID NOs: 3 and 4, respectively;

b) the $V_H$ and/or the $V_L$ nucleotide sequences set forth as SEQ ID NOs: 18 and 19, respectively;

c) the $V_H$ and/or the $V_L$ nucleotide sequences set forth as SEQ ID NOs: 27 and 19, respectively;

d) the $V_H$ and/or the $V_L$ nucleotide sequences set forth as SEQ ID NOs: 31 and 32, respectively;

e) the $V_H$ and/or the $V_L$ nucleotide sequences set forth as SEQ ID NOs: 41 and 42, respectively;

f) the $V_H$ and/or the $V_L$ nucleotide sequences set forth as SEQ ID NOs: 45 and 46, respectively; or g) the $V_H$ and/or the $V_L$ nucleotide sequences set forth as SEQ ID NOs: 55 and 56, respectively.

21. The nucleic acid molecule of claim 19, wherein the nucleic acid molecule is a cDNA sequence.

22. The nucleic acid molecule of claim 19, operably linked to a promoter.

23. A vector comprising the nucleic acid molecule of claim 19.

24. An isolated host cell comprising the vector claim 23.

25. An isolated T cell expressing the chimeric antigen T cell receptor of claim 17.

26. A pharmaceutical composition comprising an effective amount of a) the antibody or antigen binding fragment of claim 1, b) a nucleic acid molecule encoding the antibody, antigen binding fragment, or a chimeric antigen receptor comprising the antibody or antigen binding fragment, or c) a vector comprising the nucleic acid molecule; and a pharmaceutically acceptable carrier.

27. A method of producing an antibody or antigen binding fragment that specifically binds to EGFRvIII, or a bispecific antibody comprising the monoclonal antibody or antigen binding fragment, the method comprising:

expressing one or more nucleic acid molecules encoding the antibody, antigen binding fragment, or bispecific antibody of claim 1 in a host cell; and purifying the antibody, antigen binding fragment, or the bispecific antibody.

28. A method of detecting the presence of EGFRVIII in a biological sample from a human subject, comprising:

contacting the biological sample with an effective amount of the antibody or antigen binding fragment of claim 1 under conditions sufficient to form an immune complex; and detecting the presence of the immune complex in the biological sample, wherein the presence of the immune complex in the biological sample indicates the presence of EGFRVIII in the sample.

29. The method of claim 28, wherein the subject has a glioma, a head and neck cancer, a breast cancer or a bladder cancer.

30. The method of claim 29, wherein the biological sample is a biopsy from the glioma, the head and neck cancer, the breast cancer or the bladder cancer, respectively.

31. A method of inhibiting a tumor expressing EGFRvIII in a subject, comprising administering an effective amount of the pharmaceutical composition of claim 26 to the subject, wherein the subject has a tumor expressing EGFRvIII.

32. The method of claim 31, wherein the tumor is a glioma, a head and neck cancer, a breast cancer or a bladder cancer.

33. The method of claim 31, wherein the subject is human.

34. The method of claim 31, wherein inhibiting the tumor comprises reducing the growth, size, or metastasis of the tumor.

35. A method of inhibiting a tumor over-expressing EGFR in a subject, comprising:

administering an effective amount of the pharmaceutical composition of claim 26 to the subject having the tumor overexpressing EGFR, wherein the antibody or antigen binding fragment comprises the $V_H$ comprising the HCDR1, the HCDR2, and the HCDR3 of SEQ ID NO: 1, and the $V_H$ comprising the LCDR1, the LCDR2, and the LCDR3 of SEQ ID NO: 2, thereby inhibiting the tumor in the subject.

36. The method of claim 35, wherein the tumor is a glioma, a head and neck cancer, a breast cancer or a bladder cancer.

37. The method of claim 35, wherein the subject is human.

38. The method of claim 35, wherein inhibiting the tumor comprises reducing the growth, size, or metastasis of the tumor.

* * * * *